(12) United States Patent
Xin

(10) Patent No.: US 11,707,511 B2
(45) Date of Patent: Jul. 25, 2023

(54) VACCINE COMPOSITIONS AND METHODS OF USING THE SAME

(71) Applicant: The Board of Supervisors of Louisiana State University and Agricultural and Mechanical College, Baton Rouge, LA (US)

(72) Inventor: Hong Xin, New Orleans, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

(*) Notice: Subject to any disclaimer, the term of this patent is extended or adjusted under 35 U.S.C. 154(b) by 59 days.

(21) Appl. No.: 16/722,846

(22) Filed: Dec. 20, 2019

(65) Prior Publication Data

US 2020/0222518 A1    Jul. 16, 2020

Related U.S. Application Data

(63) Continuation-in-part of application No. PCT/US2018/038512, filed on Jun. 20, 2018.

(60) Provisional application No. 62/522,217, filed on Jun. 20, 2017.

(51) Int. Cl.
*A61K 39/00* (2006.01)
*C07K 14/40* (2006.01)
*A61K 39/395* (2006.01)

(52) U.S. Cl.
CPC .... *A61K 39/0002* (2013.01); *A61K 39/39575* (2013.01); *C07K 14/40* (2013.01); *A61K 2039/505* (2013.01); *A61K 2039/55505* (2013.01); *A61K 2039/575* (2013.01); *C07K 2317/24* (2013.01); *C07K 2319/40* (2013.01)

(58) Field of Classification Search
CPC ........ A61K 39/00; A61K 39/02; A61K 45/00; A61K 2039/55505
USPC ...................... 424/184.1, 185.1, 234.1, 278.1
See application file for complete search history.

(56) References Cited

U.S. PATENT DOCUMENTS

| 4,816,567 A | 3/1989 | Cabilly et al. |
| 5,939,598 A | 8/1999 | Kucherlapati et al. |
| 6,075,181 A | 6/2000 | Kucherlapati et al. |
| 6,150,584 A | 11/2000 | Kucherlapati et al. |
| 7,241,613 B1 | 7/2007 | Willins et al. |
| 7,968,297 B2 | 6/2011 | Meinke et al. |
| 9,062,093 B2 | 6/2015 | Chen et al. |
| 9,220,244 B2 | 12/2015 | Tanamachi et al. |
| 9,290,786 B2 | 3/2016 | Lanzavecchia |
| 9,416,173 B2 | 8/2016 | Xin et al. |
| 9,649,375 B2 | 5/2017 | Garry et al. |
| 10,590,178 B2 | 3/2020 | Xin |
| 10,706,955 B2 | 7/2020 | Bremel et al. |
| 2002/0016681 A1 | 2/2002 | Ekins et al. |
| 2005/0037444 A1* | 2/2005 | Meinke ................... C07K 14/31 435/7.23 |
| 2007/0027309 A1* | 2/2007 | Weinstock ........... C12Q 1/6895 536/23.7 |
| 2007/0196378 A1 | 8/2007 | Lotz et al. |
| 2009/0104218 A1* | 4/2009 | Tettelin .................... A61P 29/00 424/190.1 |
| 2009/0264620 A1 | 10/2009 | Moss et al. |
| 2012/0093761 A1* | 4/2012 | Daftarian ................. A61P 37/02 424/78.17 |
| 2013/0330335 A1* | 12/2013 | Bremel .................. G16B 20/00 424/134.1 |
| 2017/0137476 A1 | 5/2017 | Xin |

FOREIGN PATENT DOCUMENTS

| CN | 101942434 A | * | 1/2011 | |
| EP | 2003960 | | 6/2015 | |
| WO | 02061113 | | 8/2002 | |
| WO | 2002/061113 | | 5/2004 | |
| WO | 2006/076594 | | 7/2006 | |
| WO | 2006076594 | | 7/2006 | |
| WO | WO-2008109833 A2 | * | 9/2008 | ............. C07K 14/38 |
| WO | 2015/187779 | | 12/2015 | |
| WO | 2015187779 | | 12/2015 | |

OTHER PUBLICATIONS

Gen Bank Accession # KGQ83901 Nov. 5, 2014.*
Gen Bank Accession # EAO74548 Oct. 6, 2005.*
Genbank Accession No. AOW28947.1, fructose-bisphosphate aldolase [Candida albicans Sc5314].
International Search Report dated Dec. 11, 2018.
Written Opinion dated Dec. 11, 2018.
5-Methyltetrahydropteroyltriglutamate-HomocysteineS-Methyltransferase_GenBank_Accession_No_AOW30921 (Met6 ; GenBank Access No. AOW30921; Protein Accession No. XP_718219.
Al-Lazikani, Bissan, Arthur M. Lesk, and Cyrus Chothia. "Standard conformations for the canonical structures of immunoglobulins." Journal of molecular biology 273.4 (1997): 927-948.
Alexander, Jeff, et al. "Linear PADRE T helper epitope and carbohydrate B cell epitope conjugates induce specific high titer IgG antibody responses." The Journal of Immunology 164.3 (2000): 1625-1633.
Arendrup, M., T. Horn, and N. Frimodt-Møller. "In vivo pathogenicity of eight medically relevant *Candida* species in an animal model." Infection 30.5 (2002): 286-291.
Arnesen, Thomas. "Towards a functional understanding of protein N-terminal acetylation." PLoS Biol 9.5 (2011): e1001074.
Bedford, Mark T., et al. "Arginine methylation inhibits the binding of proline-rich ligands to Src homology 3, but not WW, domains." Journal of Biological Chemistry 275.21 (2000): 16030-16036.
Brüggemann, Marianne, et al. "Human antibody production in transgenic animals." Archivum immunologiae et therapiae experimentalis 63.2 (2015): 101-108.

(Continued)

*Primary Examiner* — Oluwatosin A Ogunbiyi

(74) *Attorney, Agent, or Firm* — Baker Donelson

(57) ABSTRACT

This invention is directed to vaccine compositions and methods of using the same to prevent infection.

20 Claims, 28 Drawing Sheets

Specification includes a Sequence Listing.

(56) References Cited

OTHER PUBLICATIONS

Cassone, Antonio. Development of vaccines for Candida albicans: fighting a skilled transformer. Nature Reviews Microbiology 11.12 (2013): 884 891.
Cenci E, et al. T cell vaccination in mice with invasive pulmonary aspergillosis. J. Immunol. 2000; 165:381-8.
Cerovsky, Vaclav, and Maria-Regina Kula. Peptide amidase-catalyzed C-terminal peptide amidation in a mixture of organic solvents. Peptides for the New Millennium (2002): 142-143.
Chung, J. W., et al. 2006. Risk factors and outcome for breakthrough candidemia in patients with cancer. Mycoses 49: 114-118.
Clancy CJ, et al. Immunoglobulin G responses to a panel of Candida albicans antigens as accurate and early markers for the presence of systemic candidiasis. J Clin Microbiol. May 2008;46(5):1647-54.
Cottingham, Ian R., et al. A method for the amidation of recombinant peptides expressed as intein fusion proteins in Escherichia coli. Nature biotechnology 19.10 (2001): 974-944.
Debernardis, F. et al. A virosomal vaccine against candida vaginitis: immunogenicity, efficacy and safety profile in animal models. Vaccine 30, 4490-4498 (2012).
Di Gioia ML, et al. N-Methylated a-Amino Acids And Peptides: Synthesis And Biological Activity. Mini Rev Med Chem. 2016;16(9):683-90.
Dockrell, David H., et al. Immunogenicity of three Haemophilus influenzae type b protein conjugate vaccines in HIV seropositive adults and analysis of predictors of vaccine response. Vaccine 17.22 (1999): 2779-2785.
Dos Santos, Sigrid De Sousa, et al. Haemophilus influenzae type b immunization in adults infected with the human immunodeficiency virus. AIDS research and human retroviruses 20.5 (2004): 493-496.
Enolase_GenBank_Accession_No_AAA71939 Enolase ( Enol; GenBank Accession No. AAA71939 ).
Fishwild DM, et al. High-avidity human IgG kappa monoclonal antibodies from a novel strain of minilocus transgenic mice. Nat Biotechnol. Jul. 1996;14(7):845-51.
Fructose-BisphosphateAldolase_GenBank_Accession_No_AOW28947l (Fba) ; GenBank Accession No. AOW28947 ; Protein Accession No. XP_722690).
Fujita, Yoshio, and Hiroaki Taguchi. Current status of multiple antigen-presenting peptide vaccine systems: Application of organic and inorganic nanoparticles. Chemistry Central Journal 5.1 (2011): 48.
Gap1_GenBank_Accession_No_AOW29704 glyceraldehyde-3-phosphate dehydrogenase (Gap1 ; GenBank Accession No. AOW29704).
Gonzales, Noreen R., et al. "SDR grafting of a murine antibody using multiple human germline templates to minimize its immunogenicity." Molecular immunology 41.9 (2004): 863-872.
Green, L. L., et al. "Antigen-specific human monoclonal antibodies from mice engineered with human Ig heavy and light chain YACs." Nature genetics 7.1 (1994): 13-21.
Green, Larry L. "Antibody engineering via genetic engineering of the mouse: XenoMouse strains are a vehicle for the facile generation of therapeutic human monoclonal antibodies." Journal of immunological methods 231.1-2 (1999): 11-23.
Guinea, J. "Global trends in the distribution of Candida species causing candidemia." Clinical Microbiology and Infection 20 (2014): 5-10.
Han, Yongmoon, and Jim E. Cutler. "Antibody response that protects against disseminated candidiasis." Infection and Immunity 63.7 (1995): 2714-2719.
Han, Yongmoon, Marcia H. Riesselman, and Jim E. Cutler. "Protection against candidiasis by an immunoglobulin G3 (IgG3) monoclonal antibody specific for the same mannotriose as an IgM protective antibody." Infection and immunity 68.3 (2000): 1649-1654.
Huston, James S., et al. "Protein engineering of antibody binding sites: recovery of specific activity in an anti-digoxin single-chain Fv analogue produced in Escherichia coli." Proceedings of the National Academy of Sciences 85.16 (1988): 5879-5883.
HyphalWallProtein1_GenBank_Accession_No_ACN63125 Hwp1 ; GenBank Access No. ACN63125 ).
International Search Report for PCT/US2018/038512, dated Dec. 11, 2018.
Ito, James I., and Joseph M. Lyons. "Vaccination of corticosteroid immunosuppressed mice against invasive pulmonary aspergillosis." The Journal of infectious diseases 186.6 (2002): 869-871.
Ito, James I., et al. "Vaccinations with recombinant variants of Aspergillus fumigatus allergen Asp f 3 protect mice against invasive aspergillosis" Infection and immunity 74.9 (2006): 5075-5084.
Jones, Peter T., et al. "Replacing the complementarity-determining regions in a human antibody with those from a mouse." Nature 321.6069 (1986): 522-525.
Kabat et al. Sequences of Proteins of Immunological Interest, (5th Ed., 1991), National Institutes of Health, Bethesda Md.
Kashmiri, Syed VS, et al. "SDR grafting—a new approach to antibody humanization." Methods 36.1 (2005): 25-34.
Klugman, Keith P., et al. "A trial of a 9-valent pneumococcal conjugate vaccine in children with and those without HIV infection." New England Journal of Medicine 349.14 (2003): 1341-1348.
Köhler G, Milstein C. Continuous cultures of fused cells secreting antibody of predefined specificity. Nature. Aug. 7, 1975;256(5517):495-7.
Kowalczyk, Wioleta, et al. "Synthesis of multiple antigenic peptides (MAPs)—strategies and limitations." Journal of Peptide Science 17.4 (2011): 247-251.
Lee, Young-Ho, and Michael R. Stallcup. "Minireview: protein arginine methylation of nonhistone proteins in transcriptional regulation." Molecular endocrinology 23.4 (2009): 425-433.
Leung, Ting-Fan, et al. "Immunogenicity of a two-dose regime of varicella vaccine in children with cancers." European journal of haematology 72.5 (2004): 353-357.
Levin, Myron J., et al. "Immunization of HIV-infected children with varicella vaccine." The Journal of pediatrics 139.2 (2001): 305-310.
Maccallum, D. M., 2012. Hosting Infection: ExperimentalModels to Assay Candida Virulence. International Journal of Microbiology 2012: 1-12.
Madhi, Shabir A., et al. The impact of a 9-valent pneumococcal conjugate vaccine on the public health burden of pneumonia in HIV-infected and uninfected children. Clinical infectious diseases 40.10 (2005): 1511-1518.
Mccafferty, John, et al. "Phage antibodies: filamentous phage displaying antibody variable domains." nature 348.6301 (1990): 552-554.
Mura, Manuela, et al. "The effect of amidation on the behaviour of antimicrobial peptides." European Biophysics Journal 45.3 (2016): 195-207.
Nordøy, Tone, et al. "Cancer patients undergoing chemotherapy show adequate serological response to vaccinations against influenza virus and Streptococcus pneumoniae." Medical Oncology 19.2 (2002): 71-78.
Osbourn, Jane, Maria Groves, and Tristan Vaughan. "From rodent reagents to human therapeutics using antibody guided selection." Methods 36.1 (2005): 61-68.
Pappas, P. G., et al. 2003. A prospective observational study of candidiemia: epidemiology, therapy, and influences on mortality in hospitalized adult and pediatric patients. Clin. Infect. Dis. 37: 634-643.
Pappas, P. G., et al. 2009. Clinical practice guidelines for the management of candidiasis: 2009 update by the Infectious Diseases Society of America. Clin. Infect. Dis. 48: 503-535.
Burdon, R. H. and P. H. van Knippenberg, Laboratory Techniques in Biochemistry and Molecular Biology; vol. 19, 1988, Chapter 3 Peptide-carrier conjugation: pp. 95-130.
Filler, S. G., and J. E. Edwards Jr. "When and how to treat serious candidal infections: concepts and controversies." Current clinical topics in infectious diseases 15. (1995): 1-18.
Hermanson, GT, Bioconjugate Techniques, Academic Press, 2nd ed, 2008, 20 pages.
Paul, William E. Fundamental Immunology, 3rd Ed., Raven Press, N.Y. (1993), 7 pages.

(56) References Cited

OTHER PUBLICATIONS

PeptideSyn_Technology_LifeTein The PeptideSyn technology used by LifeTein (https://www.lifetein.com/multiple-antigenic-peptides.html).

Petrovsky, Nikolai, and Julio Cesar Aguilar. Vaccine adjuvants: current state and future trends. Immunology and cell biology 82.5 (2004): 488-496.

PhosphoglycerateKinase_GenBank_Accession_No_AAA66523 phosphoglyceratekinase ( Pgk1; GenBank Accession No. AAA66523.

Pichichero, Michael E. "Protein carriers of conjugate vaccines: characteristics, development, and clinical trials." Human vaccines & immunotherapeutics 9.12 (2013): 2505-2523.

Pitarch, Aida, Cesar Nombela, and Concha Gil. "Prediction of the clinical outcome in invasive candidiasis patients based on molecular fingerprints of five anti-Candida antibodies in serum." Molecular & Cellular Proteomics 10.1 (2011): M110-004010.

Pitarch, Aida, et al. "Proteomics-based identification of novel Candida albicans antigens for diagnosis of systemic candidiasis in patients with underlying hematological malignancies." Proteomics 4.10 (2004): 3084-3106.

Poornima, Gopalakrishna, et al. "Arginine methylation promotes translation repression activity of eIF4G-binding protein, Scd6." Nucleic acids research 44.19 (2016): 9358-9368.

Ramírez-Gualito, Karla, et al. "Structural Characterization by NMR of a Double Phosphorylated Chimeric Peptide Vaccine for Treatment of Alzheimer's Disease." Molecules 18.5 (2013): 4929-4941.

Reche PA, et al. Peptide-based immunotherapeutics and vaccines. J Immunol Res. 2014;2014:256784.

Remington's Pharmaceutical Sciences, 15th Ed., Eason ed Mack Publishing Co., pp. 1405-1412 and 1461-1487 (1975).

Riechmann, Lutz, et al. "Reshaping human antibodies for therapy." Nature 332.6162 (1988): 323-327.

Roberts, M. J., M. D. Bentley, and J. M. Harris. "Chemistry for peptide and protein PEGylation." Advanced drug delivery reviews 54.4 (2002): 459-476.

Sambrook et al., Molecular Cloning: A Laboratory Manual, Cold Spring Harbor Laboratory, Cold Spring Harbor, 1989, 23 Pages.

Saylor, Carolyn, Ekaterina Dadachova, and Arturo Casadevall. "Monoclonal antibody-based therapies for microbial diseases." Vaccine 27 (2009): G38-G46.

Schedl, Andreas, et al. "A method for the generation of YAC transgenic mice by pronuclear microinjection." Nucleic acids research 21.20 (1993): 4783-4787.

Schedl, Andreas, et al. "A yeast artificial chromosome covering the tyrosinase gene confers copy number-dependent expression in transgenic mice." Nature 362.6417 (1993): 258-261.

Schedl, Andreas, et al. "Transgenic mice generated by pronuclear injection of a yeast artificial chromosome." Nucleic acids research 20.12 (1992): 3073-3077.

Schmidt, Clint S., et al. NDV-3, a recombinant alum-adjuvanted vaccine for Candida and *Staphylococcus aureus*, is safe and immunogenic in healthy adults. Vaccine 30.52 (2012): 7594-7600.

Sinisalo, Mariana, et al Haemophilus influenzae typeb (Hib) antibody concentrations and vaccination responses in patients with chronic lymphocytic leukaemia: predicting factors for response. Leukemia & lymphoma 43.10 (2002): 1967-1969.

Skwarczynski, Mariusz, and Istvan Toth. Peptide-based synthetic vaccines. Chemical Science 7.2 (2016): 842-854.

Son, Young-Ik, et al. "A novel bulk-culture method for generating mature dendritic cells from mouse bone marrow cells." Journal of immunological methods 262.1-2 (2002): 145-157.

Spampinato, Claudia, and Darío Leonardi. "Candida infections, causes, targets, and resistance mechanisms: traditional and alternative antifungal agents." BioMed research international 2013 (2013).

Spellberg, Brad. "Vaccines for invasive fungal infections." F1000 medicine reports 3 (2011).

Tam, James P. "Synthetic peptide vaccine design: synthesis and properties of a high-density multiple antigenic peptide system." Proceedings of the National Academy of Sciences 85.15 (1988): 5409-5413.

Tedaldi, Ellen M., et al. "Hepatitis A and B vaccination practices for ambulatory patients infected with HIV." Clinical Infectious Diseases 38.10 (2004): 1478-1484.

Tomljenivoc, L., and C. A. Shaw. Aluminum vaccine adjuvants: are they safe? Current medicinal chemistry 18.17 (2011): 2630-2637.

Wallace, R. John. "Acetylation of peptides inhibits their degradation by rumen micro-organisms." British journal of nutrition 68.2 (1992): 365-372.

Wegmann F, et al. The Carbomer-Lecithin Adjuvant Adjuplex Has Potent Immunoactivating Properties and Elicits Protective Adaptive Immunity against Influenza Virus Challenge in Mice. Clin Vaccine Immunol. Sep. 2015;22(9):1004-12.

Weiner, Louis M. "Fully human therapeutic monoclonal antibodies." Journal of immunotherapy 29.1 (2006): 1-9.

Wilson, Leslie S., et al. "The direct cost and incidence of systemic fungal infections." Value in Health 5.1 (2002): 26-34.

Winter, Greg, and Cesar Milstein. "Man-made antibodies." Nature 349.6307 (1991): 293-299.

Written Opinion of the ISA for PCT/US2018/038512, dated Dec. 11, 2018.

Xin, H. "Double chimeric peptide vaccine and monoclonal antibodies that protect against disseminated candidiasis." J Vaccines Vaccin 5.4 (2014).

Xin, H., et al. 2007. Antigen-pulsed dendritic cells used for identification of carrier peptides and eventual glycopeptide conjugate vaccines against candidiasis. ASM Proc. (Abst).

Xin, Hong, and Jim E. Cutler. "Vaccine and monoclonal antibody that enhance mouse resistance to candidiasis." Clinical and Vaccine Immunology 18.10 (2011): 1656-1667.

Xin, Hong, et al. "Self-adjuvanting glycopeptide conjugate vaccine against disseminated candidiasis." PloS one 7.4 (2012): e35106.

Xin, Hong, et al. "Synthetic glycopeptide vaccines combining β-mannan and peptide epitopes induce protection against candidiasis." Proceedings of the National Academy of Sciences 105.36 (2008): 13526-13531.

Xin, Hong. "Active immunizations with peptide-DC vaccines and passive transfer with antibodies protect neutropenic mice against disseminated candidiasis." Vaccine 34.2 (2016): 245-251.

Yano, Akira, et al. "RGD motif enhances immunogenicity and adjuvanticity of peptide antigens following intranasal immunization." Vaccine 22.2 (2003): 237-243.

\* cited by examiner

C
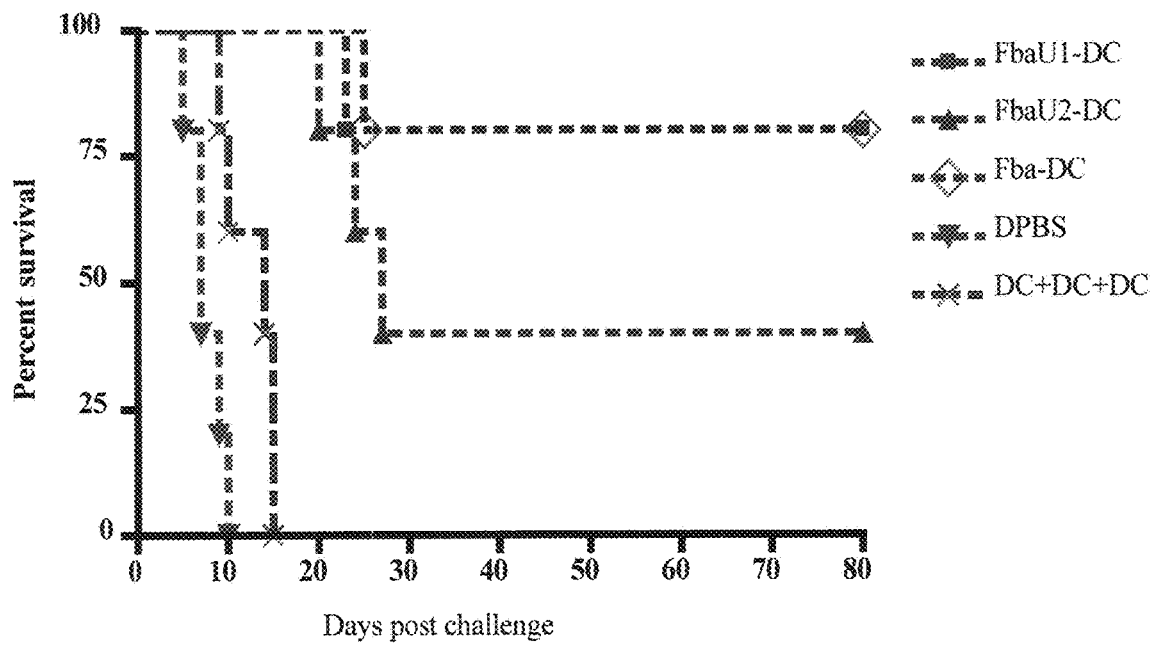
D
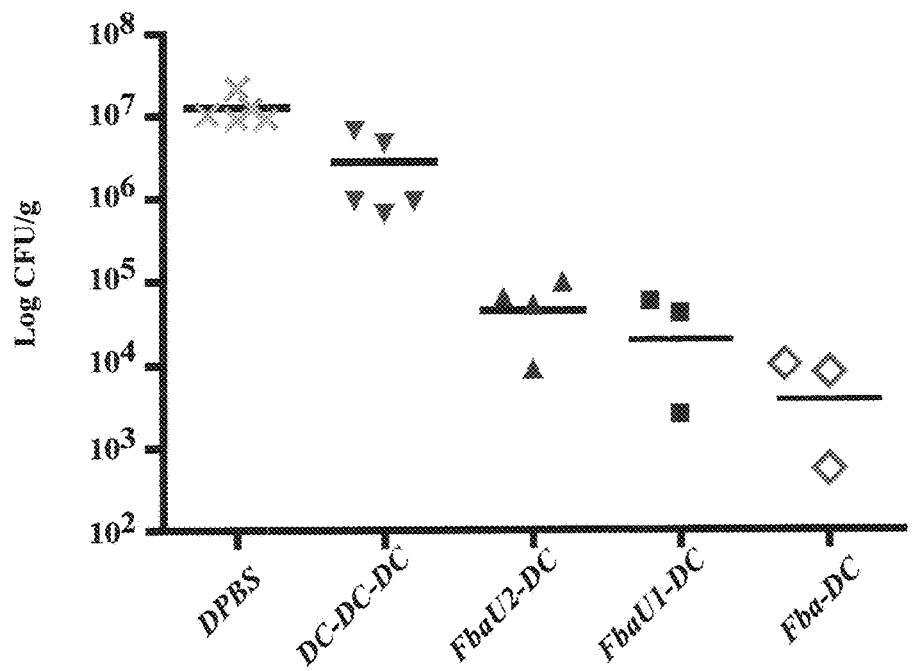
*FIG. 2 CON'T*

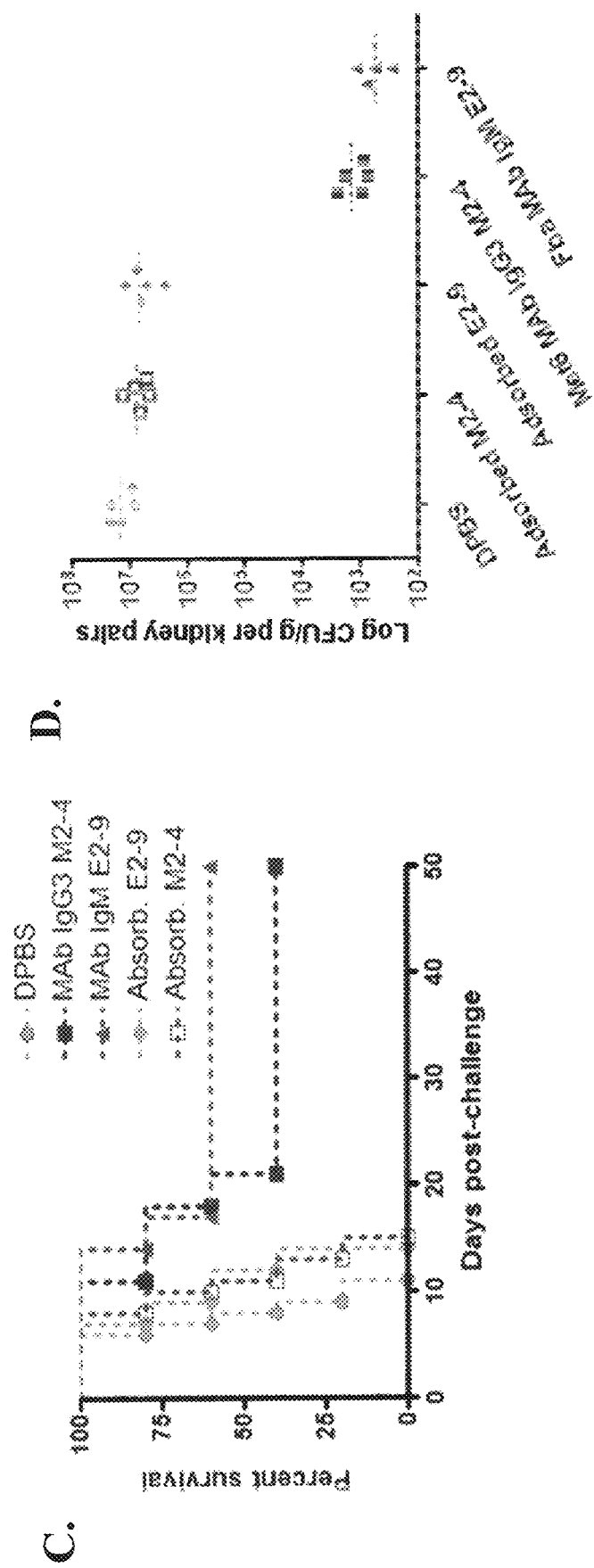
FIG. 6 CON'T

FIG. 8

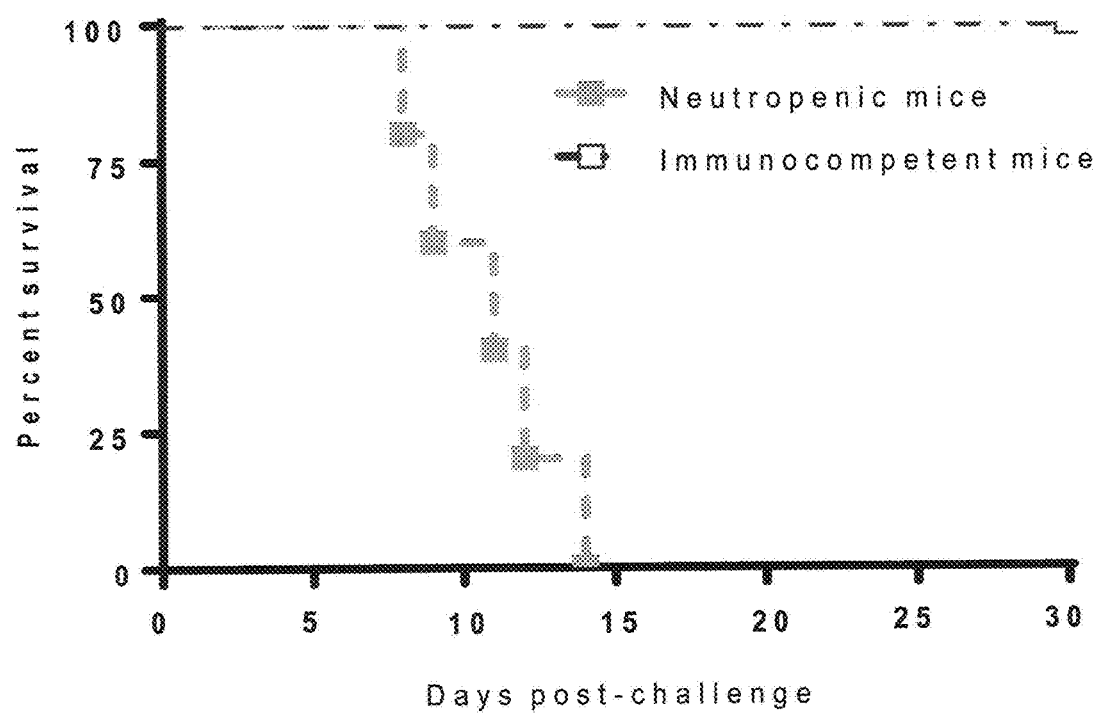
*FIG. 12 CON'T*

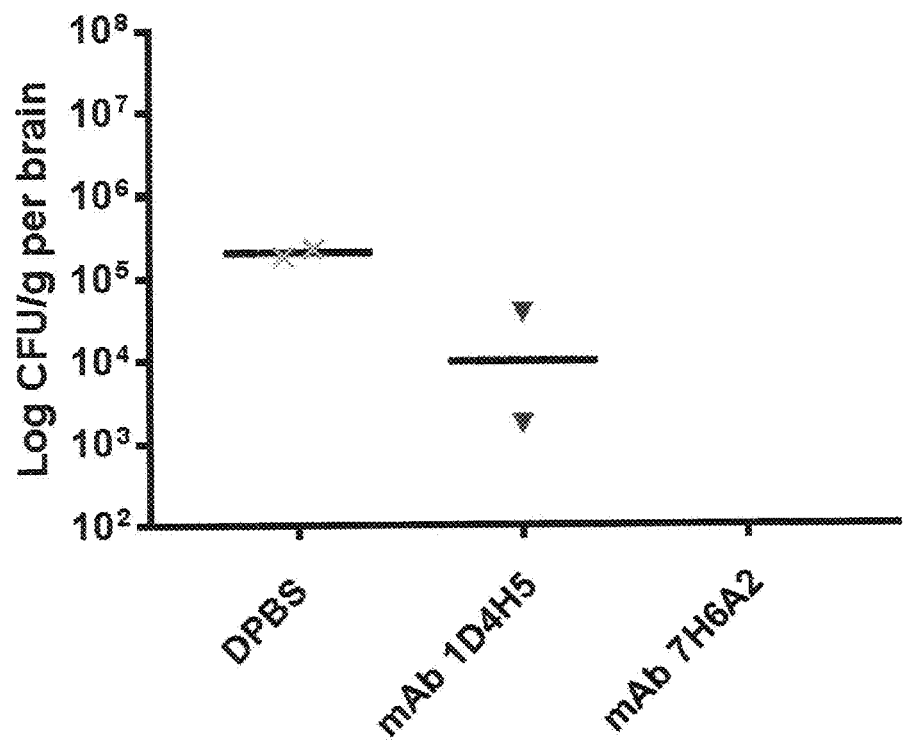
FIG. 14 CON'T

B.
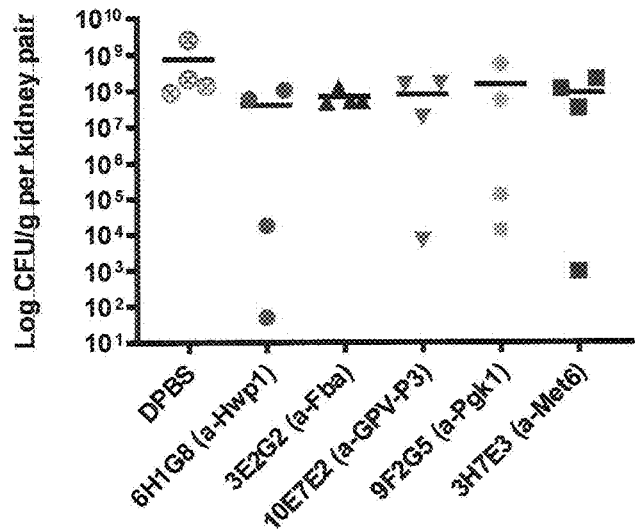
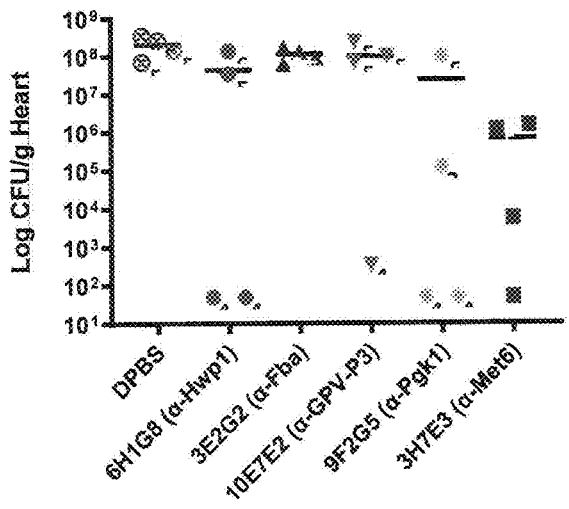
FIG. 15 CON'T
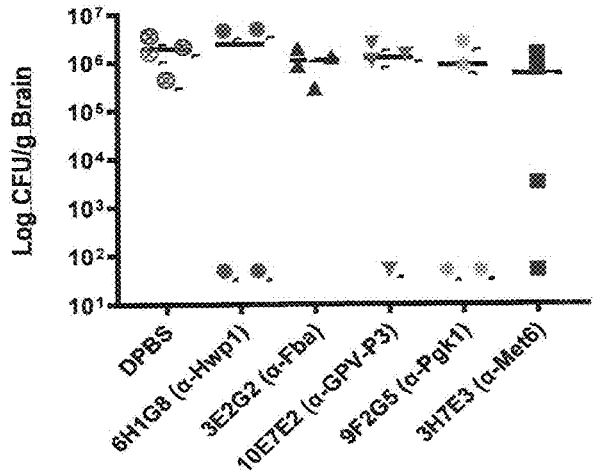

A.

B.

The homology of cell surface epitopes targeted by protective mAbs among medically significant *Candida* species

| *Candida* species | Fba* | Met6* | PGK1* | Hwp1* |
|---|---|---|---|---|
| *Candida albicans* | 100% | 100% | 100% | 100% |
| *Candida glabrata* | 79% | 85% | 86% | N/A |
| *Candida parapsilosis* | 100% | 100% | 100% | N/A |
| *Candida tropicalis* | 91% | 100% | 93% | N/A |
| *Candida dubliniensis* | 100% | 100% | 100% | N/A |
| *Candida krusei* | 100% | 100% | Not known | N/A |
| *Candida auris* | 78% | 100% | 93% | ?-100% |

*FIG. 19*

VACCINE COMPOSITIONS AND METHODS OF USING THE SAME

This application is a Continuation-In-Part of International Patent Application No. PCT/US2018/038512, filed on Jun. 20, 2018, which claims priority from U.S. Provisional Patent Application No. 62/522,217, filed on Jun. 20, 2017, the contents of each of which are incorporated herein by reference in its entirety.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

GOVERNMENT INTERESTS

This invention was made with government support under Grant No. R03AI107536 awarded by the National Institutes of Health. The government has certain rights in the invention.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to vaccine compositions and methods of using the same to prevent infection.

BACKGROUND OF THE INVENTION

Morbidity and mortality from invasive fungal infections remain unacceptably high despite availability of antifungal agents, underscoring the need for more effective preventative strategies. Invasive fungal diseases often take hold when a person's natural defenses are weakened. These infections frequently occur in hospital settings. Vaccination of high-risk groups is a promising strategy to prevent invasive fungal infections because identifiable risk factors are defined for many such infections. Development of these risk factors can precede infection, affording a window of opportunity to vaccinate acutely at-risk patients before the onset of infection.

SUMMARY OF THE INVENTION

The present invention provides an antigenic universal peptide comprising a peptide that is at least 70% identical in two or more different microorganisms. In embodiments, the peptide is at least 60% identical in two or more different microorganisms. In embodiments, the peptide is 60%, 61%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% identical in two or more different microorganisms.

In embodiments, the microorganism is not *Candida*.

In embodiments, the peptide comprises at least nine consecutive amino acid residues. In embodiments, the peptide comprises at least 7, 8, 9, 10, 11, 12, 13, 14, 15, 16, 17, 18, 19, 20, 21, 22, 23, 24, 25 consecutive amino acid residues. In embodiments, the peptide is modified for use as a vaccine in a mammal. For example, the modification can comprise methylation, amidation, acetylation, PEGylation, incorporation of a cysteine residue, conjugation to at least one macromolecule, or a combination thereof.

Non-limiting examples of such mammals that can benefit from embodiments of the invention comprise a human, dog, cat, pig, cow, or horse. In embodiments, the subject comprises a chicken or bird.

In embodiments, the antigenic universal peptide elicits an immune response in the subject, such as a mammal.

In embodiments, the antigenic peptide, such as the antigenic universal peptide or chimeric peptide, is resistant to proteolytic cleavage.

In embodiments, the peptide comprises a cell wall peptide, such as a fungal cell wall peptide or a bacterial cell wall peptide. Non-limiting examples of fungal cell wall peptides comprise those of fructose-bisphosphate aldolase (Fba), methyltetrahydropteroyltriglutamate homocysteine methyltransferase (Met6), hyphal wall protein-1 (Hwp1), enolase (Eno1), glyceraldehyde-3-phosphate dehydrogenase (Gap1), and phosphoglycerate kinase (Pgk1).

In embodiments, the amino acid sequence of the antigenic universal peptide comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82.

The invention also provides a nucleic acid encoding an antigenic universal peptide. For example, the nucleic acid can encode for an antigenic universal peptide that is at least 70% identical in two or more different microorganisms, such as two or more different fungal species.

Further, the invention provides for a vaccine composition comprising an antigenic universal peptide and a pharmaceutically acceptable carrier. In such embodiments, the amino acid sequence of the antigenic universal peptide is at least 70% identical in two or more different microorganisms.

The invention also provides a vaccine composition comprising a nucleic acid encoding an amino acid sequence of an antigenic universal peptide and a pharmaceutically acceptable carrier. For example, the pharmaceutically acceptable carrier can be a solid, liquid, solution, suspension, gel, ointment, lotion, or combinations thereof, including aqueous solutions, non-toxic excipients, including salts, preservatives, and buffers.

In embodiments, the vaccine composition can comprise two or more antigenic universal peptides. For example, the two or more antigenic universal peptides can be mixed, or the two or more antigenic peptides can be covalently linked. In other embodiments, the vaccine composition can comprise at least one universal antigenic peptide, and at least one additional antigenic peptide, wherein the additional antigenic peptide is not a universal antigenic peptide. For example, the vaccine composition can comprise the amino acid sequence of SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93.

In still other embodiments, the vaccine composition can comprise two or more nucleic acid sequences, each encoding an amino acid sequence of an antigenic peptide, for example an antigenic universal peptide.

The invention also provides a chimeric peptide comprising two or more antigenic peptides, at least one of which comprises an antigenic universal peptide. In embodiments, the additional peptide, such as an additional antigenic universal peptide or an antigenic peptide that is not a universal peptide, is covalently linked to the antigenic universal peptide by a linker. For example, the linker comprises a peptide linker, such as the amino acid sequence KK (SEQ ID NO: 49), GPSL (SEQ ID NO: 50), PADRE (SEQ ID NO: 51).

In embodiments, the amino acid sequence of the additional antigenic peptide(s), such as an additional antigenic universal peptide, comprises a peptide that is at least 70% identical in two or more different microorganisms. In embodiments, the additional antigenic peptide is 60%, 61%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% identical in two or more different microorganisms.

In embodiments, the additional antigenic peptide comprises at least nine consecutive amino acid residues. In embodiments, the peptide comprises at least 7, 8, 9, 10, 11, 12, 13, 14, 15, 16, 17, 18, 19, 20, 21, 22, 23, 24, 25 consecutive amino acid residues.

In embodiments, the chimeric peptide comprises one, two, or more than two antigenic peptides of fructose-bisphosphate aldolase (Fb a), methyltetrahydropteroyltriglutamate homocysteine methyltransferase (Met6), hyphal wall protein-1 (Hwp1), enolase (Eno1), glyceraldehyde-3-phosphate dehydrogenase (Gap1), and phosphoglycerate kinase (Pgk1), such as antigenic universal peptides of the same.

In embodiments, the chimeric peptide comprises one, two, or more than two antigenic universal peptide, such as those of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, SEQ ID NO: 82, or any combination thereof.

In embodiments, the chimeric peptide comprises one, two, or more than two antigenic peptides, such as those of the amino acid sequence of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, or SEQ ID NO: 48, or any combination thereof.

Embodiments can further comprise comprises the addition of one or more additional amino acid residues, for example cysteine residues, and/or other modifications, non-limiting examples of which comprise methylation, amidation, acetylation, PEGylation, conjugation to at least one macromolecule, or a combination thereof.

In embodiments, the antigenic peptide, such as the antigenic universal peptide, is a T-cell epitope.

Embodiments of the invention further provide for a vaccine composition comprising at least two antigenic peptides, such as at least two antigenic universal peptides, and a pharmaceutically acceptable carrier. The amino acid sequence of the first antigenic universal peptide can be at least 70% identical in two or more different microorganisms, and optionally, wherein the amino acid sequence of the additional antigenic peptide(s) is at least 70% identical in two or more different microorganisms. In embodiments, each peptide comprises at least nine consecutive amino acid residues. In embodiments, the two or more antigenic universal peptides are covalently linked by a linker.

In embodiments, at least one of the antigenic universal peptides comprise a peptide at least 70% identical to the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, SEQ ID NO: 82, or any combination thereof.

In embodiments, at least one of the antigenic universal peptides comprise that of a cell wall protein, such as fructose-bisphosphate aldolase (Fba), methyltetrahydropteroyltriglutamate homocysteine methyltransferase (Met6), hyphal wall protein-1 (Hwp1), enolase (Eno1), glyceraldehyde-3-phosphate dehydrogenase (Gap1), and phosphoglycerate kinase (Pgk1).

Embodiments can further comprise an adjuvant, such as MPL, alum, Freund's adjuvant, Ribi-R730 or Adjuplex; a protein carrier, such as diphtheria toxoid, tetanus toxoid, TH epitope of tetanus toxoid, BSA, or KLH; a T helper epitope, such as pan DR-binding epitope (PADRE; SEQ ID NO: 51), RGD (SEQ ID NO: 52); a stabilizing peptide; a Multiple Antigen Peptide (MAP); or any combination thereof. Alternatively, embodiments do not require nor comprise an adjuvant, a protein carrier, or either.

The invention further provides for an isolated antibody or binding fragment thereof that specifically binds to a peptide with an amino acid sequence that is at least 70% identical in two or more different microorganisms, for example the antibody or binding fragment thereof comprises the product expressed by the clone 2C9G3, 5A9D1, 5A11B1, 6E3D9, 1D4H5, 7A3C4, 10E7E2, 1A11H8, 10B6H8, 5G5G3, or 9F2G5. In embodiments, the amino acid sequence of the peptide bound by the antigen is 60%, 61%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% identical in two or more different microorganisms.

In embodiments, the peptide that is bound by the antibody comprises at least nine consecutive amino acid residues. In embodiments, the peptide that is bound by the antibody comprises at least 7, 8, 9, 10, 11, 12, 13, 14, 15, 16, 17, 18, 19, 20, 21, 22, 23, 24, 25 consecutive amino acid residues.

In embodiments, the peptide that is bound by the antibody comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, or SEQ ID NO: 28, SEQ ID NO: 81, SEQ ID NO: 82, or any combination thereof.

The invention also provides for an isolated antibody or binding fragment thereof that specifically binds to at least one synthetic cell wall peptide with an amino acid sequence that is at least 70% identical in two or more different microorganisms, for example the antibody or binding fragment thereof comprises the product expressed by the clone 2C9G3, 5A9D1, 5A11B1, 6E3D9, 1D4H5, 7A3C4, 10E7E2, 1A11H8, 10B6H8, 5G5G3, or 9F2G5.

In embodiments, the antibody or binding fragment thereof binds to the peptide with a $K_D$ of about $10^{-12}$M or less. For example, the antibody or binding fragment thereof binds to the peptide with a $K_D$ of about $10^{-4}$ to about $10^{-12}$M.

In embodiments, the antibody or binding fragment thereof comprises a variable domain having a variable light chain ($V_L$) amino acid sequence at least 80%, 81%, 82%, 83%, 84%, 85%, 86%, 87%, 88%, 89%, 90%, 91%, 92%, 93%, 94%, 95%, 96%, 97%, 98%, 99%, 100% identical to SEQ ID NO: 62, 66, 70, 74, or having a variable heavy chain ($V_H$) amino acid sequence at least 80%, 81%, 82%, 83%, 84%, 85%, 86%, 87%, 88%, 89%, 90%, 91%, 92%, 93%, 94%, 95%, 96%, 97%, 98%, 99%, 100% identical to SEQ ID NO: 60, 64, 68, 72.

In embodiments, the antibody or binding fragment thereof comprises the product expressed by the clone 2C9G3, 5A9D1, 5A11B1, 6E3D9, 1D4H5, 7A3C4, 10E7E2, 1A11H8, 10B6H8, 5G5G3, 9F2G5.

In embodiments, the antibody is a monoclonal antibody.

In embodiments, the antibody is fully human, humanized or chimeric. In embodiments, the variable light chain ($V_L$) and/or variable heavy chain comprises fully human framework region(s).

For example, the antibody fragment comprises an Fv fragment, a Fab fragment, a F(ab') fragment, a F(ab)$_2$ fragment, a disulfide stabilized Fv protein (dsFv) fragment, a scFv fragment, a minibody fragment, or a diabody fragment.

The invention also provides for an engineered cell that secretes the antibody, such the antibody or binding fragment thereof comprises the product expressed by the clone 2C9G3, 5A9D1, 5A11B1, 6E3D9, 1D4H5, 7A3C4, 10E7E2, 1A11H8, 10B6H8, 5G5G3, or 9F2G5.

Further, the invention provides for an isolated nucleic acid encoding the antibody of such the antibody or binding fragment thereof comprises the product expressed by the clone 2C9G3, 5A9D1, 5A11B1, 6E3D9, 1D4H5, 7A3C4, 10E7E2, 1A11H8, 10B6H8, 5G5G3, or 9F2G5.

Still further, the invention provides for a recombinant expression vector comprising the isolated nucleic acid. In embodiments, the nucleic acid and/or recombinant expression vector are or can be transformed into a host cell.

The invention also provides a composition for passive protection against an infection, such as a fungal or bacterial infection, comprising an immunologically effective amount of at least one recombinant antibody or binding fragment thereof that specifically binds to a peptide with an amino acid sequence that is at least 70% identical in two or more microorganisms, and a pharmaceutically acceptable carrier. For example, the antibody of the vaccine composition specifically binds to a peptide comprising at least one of fructose-bisphosphate aldolase (Fb a), methyltetrahydropteroyltriglutamate homocysteine methyltransferase (Met6), hyphal wall protein-1 (Hwp1), enolase (Enol), glyceraldehyde phosphate dehydrogenase (Gap1), and phosphoglycerate kinase (Pgk1). In another example, the antibody of the vaccine composition specifically binds to a peptide comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, SEQ ID NO: 82, or any combination thereof.

In embodiments, the vaccine composition comprises at least one protective monoclonal antibody, such as the antibody expressed by the clone 2C9G3, 5A9D1, 5A11B1, 6E3D9, 1D4H5, 7A3C4, 10E7E2, 1A11H8, 10B6H8, 5G5G3, or 9F2G5. Antibodies of the vaccine composition, for example, can specifically bind to peptides or epitopes of SEQ ID NO.: 53, SEQ ID NO.:54, SEQ ID NO.: 55; SEQ ID NO.: 56; SEQ ID NO.: 57; SEQ ID NO.: 58.

In still other embodiments, the vaccine composition can further comprises at least one additional protective antibody, such as at least one antibody selected from the group consisting of 2C9G3, 5A9D1, 5A11B1, 6E3D9, 1D4H5, 7A3C4, 10E7E2, 1A11H8, 10B6H8, 5G5G3, or 9F2G5.

The invention also is directed towards protecting against or treating infections caused by microorganisms, such as fungal infections, bacterial infections, viral infections, and protozoal infections.

In embodiments, the fungi comprise species of *Candida, Aspergillus, Cryptococcus, Trichophyton, Microsporum, Epidermophyton, Rhizopus, Mucor, Cunninghamella, Apophysomyces, Lichtheimia, Exserohilum, Cladosporium, Blastomyces, Coccidioides, Histoplasma, Pneumocystis,* and *Sporothrix.*

In embodiments, the bacteria comprise species of *Eschericia, Salmonella, Helicobacter, Neisseria, Staphylococcus, Streptococcus, Campylobecter, Clostridium, Listeria, Vibrio Chlamydia,* and *Treponema.*

In embodiments, the virus comprises a varicella zoster virus, human immunodeficiency virus, influenza virus, herpes virus, human papillomavirus, Epstein-Barr virus, mumps virus, rubeola virus, rotavirus, norovirus, West nile virus, Ebola virus, Respiratory syncytial virus, coronavirus, rhinovirus, parainfluenza virus, adenovirus In embodiments, the protozoa comprises Giardia, *Plasmodium, Trichomonas,* and *Toxoplasma.*

Embodiments, such as compositions comprising antigenic universal peptides or isolated antibodies to such peptides, can further comprise at least one antimicrobial agent, such as an anti-fungal agent, an anti-viral agent, an anti-bacterial agent, or an anti-protozoal agent.

In embodiments, the anti-fungal agent comprises a polyene, an azole, an allylamine, an echinocardin, or a combination thereof.

In embodiments, the anti-viral agent comprises TFT, Acyclovir, gancyclovir, penciclovir, cidofovir; ribavirin, interferon, phosphonoacetate, Foscarnet, amantadine, Rimatidine, oseltamivir, Valacyclovir, Valgancydovir, Peramivir, Zanamivir, or a combination thereof.

In embodiments, the anti-bacterial agent comprises aminoglycosides, fluoroquinolones, beta-lactams, macrolide, and tetracyclines.

In embodiments, the anti-protozoal agent comprises chloroquine, pyrimethamine, mefloquine, hydroxychloroquine, metronidazole, atovaquone, or a combination thereof.

The invention further provides a method for active immunization and/or active protection against a microbial infection. In embodiments, the method comprising administering a composition that induces an immune response, for example a composition comprising at least one antigenic universal peptide or chimeric peptide, to a subject in need thereof.

Further, the invention provides for a method for passive immunization and/or passive protection against a microbial infection comprising administering a protective composition, for example a composition comprising a monoclonal antibody or humanized antibody to an antigenic universal peptide, to a subject in need thereof.

Embodiments can further comprise administering at least one antimicrobial agent, such as an anti-fungal agent, an anti-viral agent, an anti-bacterial agent, or an anti-protozoal agent, in conjunction with administering compositions as described herein.

Still further, the invention is directed towards a method for selecting a peptide vaccine. For example, the method for selecting a peptide vaccine comprises aligning the amino acid sequences of a cell wall protein in two or more different microorganisms, and selecting a peptide vaccine, wherein the amino acid sequence of the peptide vaccine is at least 70% identical in the two or more different microorganisms. Further embodiments comprise aligning the amino acid sequences and selecting a peptide vaccine, wherein the amino acid sequence of the peptide vaccine is at least 60%, 61%, 62%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% identical in two or more different microorganisms.

Embodiments can further comprise modifying the peptide vaccine to be suitable for human use or veterinary use, and/or administering the peptide vaccine to a subject in need thereof.

In embodiments, the peptide vaccine comprises a peptide having a length of 10, 11, 12, 13, 14, 15, 16, 17, 18, 19, or 20 amino acids.

Embodiments can further comprise determining the hydrophobicity value, determining the immunogenicity score, or a combination thereof.

The invention is also directed towards a therapeutic composition comprising an antibody or antibody mixture, a peptide or peptide mixture, or a combination thereof, and, optionally, an antimicrobial agent.

In embodiments, the therapeutic composition is effective to stimulate an immune response in a patient against a pathogenic/microbial infection.

In embodiments, the composition is administered over a period of at least two weeks, wherein the interval between each administration is every other day. In embodiments, the period comprises 3 weeks, 4 weeks, 6 weeks, 8 weeks, 12 weeks, or longer.

Embodiments comprise the antigenic peptides of SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93.

Other objects and advantages of this invention will become readily apparent from the ensuing description.

BRIEF DESCRIPTION OF THE FIGURES

FIG. 8 shows main prevention strategies.

FIG. 19 shows the homology of cell surface epitopes targeted by protective mAbs among medically significant *Candida* species. *Peptides found in *C. albicans* cell wall proteins and conjugated each peptide, originally intended to act as a carrier to the fungal cell wall β-1,2-trisaccharide [β-(Man)$_3$] to create glycopeptide conjugate vaccines. Four peptides (Fba, Met6, PGK1 and Hwp1) served well as effective carriers for the protective glycan epitope, turned out to be excellent vaccines by themselves in that they also induced protection against invasive candidiasis in mice. We further demonstrated that antibodies specific for the peptides are each protective. Uniquely, the protective mAbs targeting each of four peptide epitopes were also expressed 85%-100% by other medically important *Candida* species in addition to *C. albicans* (see FIG. 19). Without wishing to be bound by theory, these "universal" mAbs can protect broadly against other *Candida* species.

DETAILED DESCRIPTION OF THE INVENTION

Abbreviations and Definitions

Figure 1:
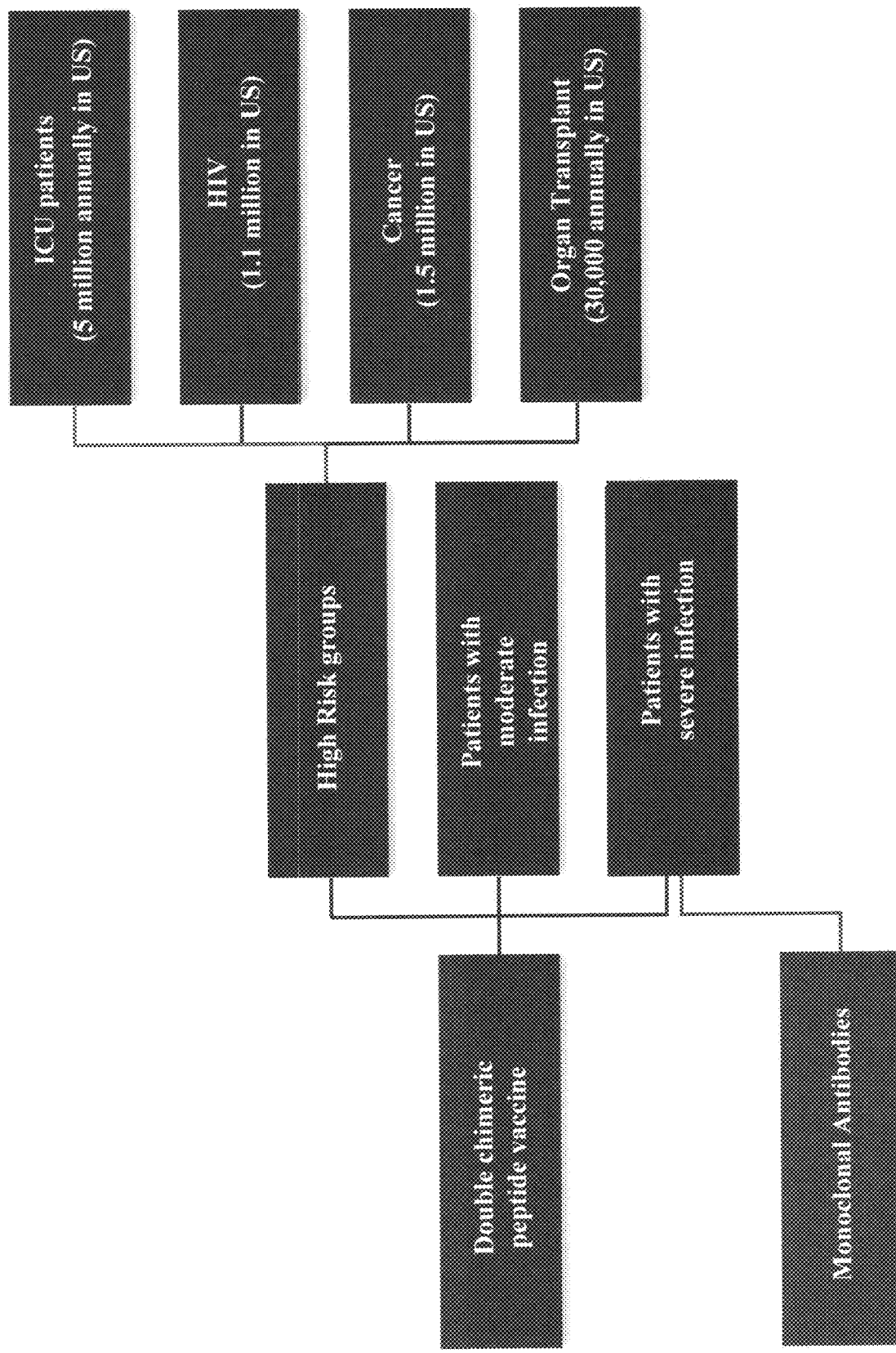
FIG. 1 shows the examples of target populations for anti-fungal vaccines and monoclonal antibodies.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly, "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the term "universal," for example "universal peptide" or "antigenic universal peptide" or "universal peptide vaccine," can refer to the ability to protect against, prevent, delay the onset of or treat infection, or symptoms thereof, caused by different microorganisms. For example, a universal peptide as described herein can protect against infections caused by various species of fungi, bacteria, viruses, and/or protozoa. Non-limiting examples of species of fungi which can cause infections comprise *Candida, Aspergillus, Cryptococcus, Trichophyton, Microsporum, Epidermophyton, Rhizopus, Mucor, Cunninghamella, Apophysomyces, Lichtheimia, Exserohilum, Cladosporium, Blastomyces, Coccidioides, Histoplasma, Pneumocystis,* and/or *Sporothrix*.

Non-limiting examples of species of bacteria which can cause infections comprise, such as *Eschericia, Salmonella, Helicobacter, Neisseria, Staphylococcus, Streptococcus, Campylobecter, Clostridium, Listeria, Vibrio Chlamydia,* and/or *Treponema*.

Non-limiting examples of viruses which can cause infections comprise varicella zoster virus, human immunodeficiency virus, influenza virus, herpes virus, human papillomavirus, Epstein-Barr virus, mumps virus, rubeola virus, rotavirus, norovirus, West nile virus, Ebola virus, Respiratory syncytial virus, coronavirus, rhinovirus, parainfluenza virus, and/or adenovirus.

Non-limiting examples of species of protozoa which can cause infections comprise *plasmodium*, trypanosome, amoeba, giardia, a species of *Acanthamoeba*. Non-limiting examples of disease caused by protozoal infections comprise *Acanthamoeba keratitis*, malaria, protozoal pneumonia.

Microbial Infections

The term "microbial infection" can refer to the invasion of the host mammal by pathogenic microbes or microorganisms capable of causing an infection. This includes the excessive growth of microbes which are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal.

Non-limiting examples of microorganisms capable of causing an infection comprise fungi, bacteria, virus, and protozoa.

For example, microbial infections can be caused by species of fungi such as *Candida, Aspergillus, Cryptococcus, Trichophyton, Microsporum, Epidermophyton, Rhizopus, Mucor, Cunninghamella, Apophysomyces, Lichtheimia, Exserohilum, Cladosporium, Blastomyces, Coccidioides, Histoplasma, Pneumocystis,* and/or *Sporothrix.*

In some embodiments, microbial infections can be caused by species of bacteria, such as *Eschericia, Salmonella, Helicobacter, Neisseria, Staphylococcus, Streptococcus, Campylobecter, Clostridium, Listeria, Vibrio Chlamydia,* and/or *Treponema.*

For example, microbial infections can be caused by viruses, such as varicella zoster virus, human immunodeficiency virus, influenza virus, herpes virus, human papillomavirus, Epstein-Barr virus, mumps virus, rubeola virus, rotavirus, norovirus, West nile virus, Ebola virus, Respiratory syncytial virus, coronavirus, rhinovirus, parainfluenza virus, and/or adenovirus.

In some embodiments, the protozoan that can cause microbial infection comprises *plasmodium,* trypanosome, amoeba, giardia, a species of *Acanthamoeba.* Non-limiting examples of disease caused by protozoal infections comprise *Acanthamoeba keratitis,* malaria, protozoal pneumonia.

Invasive Fungal Infections

The polymorphic fungus *Candida albicans* is a commensal organism that colonizes the gastrointestinal tract, vagina and some cutaneous areas of the majority of healthy humans. However, under certain conditions the fungus is able to cause a variety of infections, ranging from mucosal to life-threatening invasive candidiasis. *C. albicans* continues to be the most common cause of various forms of candidiasis, but several other *Candida* spp. are also important agents. Invasive disease is associated with billions of dollars each year in healthcare costs and a mortality rate estimated at ~40%. The limited number and toxicity of antifungal agents, and, most importantly, the poor outcome of almost half of the number of candidemia patients treated with appropriate antifungal therapy, militates in favor of disease prevention, possibly through active and passive immunization strategies.

Fungal infections, such as *candida,* commonly afflict patients in the ICU, and also those subjects with suppressed immune systems due to a variety of factors. Non-limiting examples of such factors comprise cancer, HIV, and organ transplants. Of the 68,000 cases of disseminated candidiasis, about 10-20% of the patients are severely immune-suppressed.

Positive diagnosis of fungal infections, such as invasive *Candida* functions, is largely reliant on laboratory culturing of blood samples. However, blood cultures are often positive only late in the course of infection, leading to delayed diagnosis. Without wishing to be bound by theory, non-culture-based laboratory techniques can contribute to early diagnosis and management of invasive candidiasis. For example, both serologic (mannan, antimannan, and betaglucan) and molecular (*Candida*-specific PCR in blood and serum) based techniques have been applied as serial screening procedures in high-risk patients.

Identification of patients susceptible to fungal infections who can benefit from empirical antifungal treatment remains challenging, but it is necessary to avoid antifungal overuse in critically ill patients.

For non-neutropenic patients (i.e., patients with a functioning immune system) a Fluconazole loading dose of 800 mg (12 mg/kg) followed by a daily dose of 400 mg (6 mg/kg) Fluconazole is recommended for mild to moderate illness.

Echinocandin therapy (Caspofungin: loading dose of 70 mg, then 50 mg daily; micafungin: 100 mg daily; anidulafungin: loading dose of 200 mg, then 100 mg daily) is recommended for non-neutropenic adults with moderately severe to severe illness, or infection due to *Candida glabrata.*

For non-neutropenic patients, Amphotericin B deoxycholate (AmB-d) administered at a dosage of 0.5-1.0 mg/kg daily or a lipid formulation of AmB (LFAmB) administered ata dosage of 3-5 mg/kg daily are alternatives if there is intolerance to or limited availability of other antifungals.

For neutropenic patients (i.e., patients with an impaired immune system) an echinocandin (caspofungin: loading dose of 70 mg, then 50 mg daily; micafungin: 100 mg daily; anidulafungin: loading dose of 200 mg, then 100 mg daily) or LFAmB (3-5 mg/kg daily) is recommended for most patients, including those who are critically ill.

For neutropenic patients who are less critically ill and who have no recent azole exposure, fluconazole (loading dose of 800 mg [12 mg/kg], then 400 mg [6 mg/kg] daily) is a reasonable second-line treatment.

Voriconazole can be used in situations in which additional mold coverage is desired.

The recommended duration of therapy for candidemia without obvious metastatic complications is for 2 weeks after documented clearance of *Candida* from the bloodstream and resolution of symptoms attributable to candidemia.

Because mortality remains high in patients with candidemia, antifungal prophylaxis has been considered as a means to prevent its occurrence. However, there remain few, if any, effective options for antifungal prophylaxis, although broad use of Fluconazole has shown to decrease invasive candidiasis in some trials.

Examples of populations which can benefit from embodiments of the invention, such as anti-fungal vaccine and monoclonal antibodies, is summarized in FIG. 1. For example, a broad population can benefit from being administered a chimeric peptide vaccine or a composition comprising the same. As another example, subjects resistant to anti-fungal drugs or immune-suppressed subjects can benefit from administration of the mAbs.

Peptide Vaccine

"Peptide vaccine" can refer to a peptide, for example those antigenic universal peptides described herein, or modified peptides thereof that is administered to a subject as a vaccine, either alone or as a component of a composition. For example, the peptide vaccine can comprise one or more antigenic universal peptides which share amino acid sequence homology across two or more different microorganisms and that can elicit an immune response so as to protect against infections. Antigenic universal peptides can be at least 3, 4, 5, 6, 7, 8, 9, 10, 11, 12, 13, 14, 15, 16, 17, 18, 19, 20, 21, 22, 23, 24, 25 or greater than 25 amino acids in length. In embodiments, the peptide vaccine comprises at least one of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82.

"Chimeric peptide" or "chimeric peptide vaccine" refers to peptide comprising two or more peptides, such as the universal antigenic universal peptides as described herein, covalently linked to each other. In embodiments, the chimeric peptide vaccine comprises at least one of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82.

The peptide vaccine can be a synthetic peptide vaccine. "Synthetic peptide vaccine" can refer to a peptide comprising the component of immunogenic determinants, i.e. a vaccine prepared by synthesizing a peptide according to the amino acid sequence of proteins, such as those proteins and sequences identified herein. For example, the synthetic peptide vaccine can be prepared by synthesizing a peptide of Fba, Met6, Hwp1, Enol1, Gap1, or Pgk1, and can share sequence homolog across 2 or more microorganisms. For example, the synthetic peptide vaccine can comprise the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82. In embodiments, the synthetic peptide vaccine can optionally comprise additional components such as an adjuvant and/or carrier protein.

In embodiments, the antigenic universal peptide comprises a peptide that is at least 80% identical in two or more different microorganisms. In other embodiments, the antigenic universal peptide comprises a peptide that is about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical in two or more microorganisms. In embodiments, the antigenic peptide comprises a peptide that is 100% identical in two or more microorganisms. For example, such organisms can comprise fungi, such as those relevant to disease (for example, *Candida* spp.), bacteria, viruses, or protozoa. Without wishing to be bound by theory, efficacy, such as protective efficacy, of the peptide vaccine correlates with the homology of the amino acid sequence between the two or more microorganisms. For example, protective efficacy is higher for a peptide that shares 100% homology in two or more microorganisms than that of a peptide that is 80% homologous.

For examples, embodiments comprise the antigenic universal peptide GPV-MO1 (SEQ ID NO. 81; PTTTIGSFPQ) whose amino acid sequence has 100% homology in medically important fungal species, such as *Candida* spp. *Aspergillus Fumigatus, Aspergillus Niger,* & *Streptococcus agalactiae, Streptococcus suis.*

As another example, embodiments can comprise the antigenic universal peptide GPV-MO1A (SEQ ID NO. 82; NLPLFPTTTIGSFPQTK), which corresponds to the peptide exposed on the surface of *Candida albicans*, and also shares 100% homology in medically important fungal species, such as *Candida* spp. In addition to *C. albicans, Aspergillus Fumigatus* & *Aspergillus Niger.*

Embodiments as described herein can elicit an immune response in a subject. As used herein, an "immunological response" or "immune response" to a peptide, for example an antigenic universal peptides as described herein or nucleic acid encoding the antigenic universal peptide, or composition comprising a polypeptide or nucleic acid encoding the polypeptide includes the development in a mammal of a cellular immune response that recognizes the polypeptide of the invention. In some examples, the immune response is an humoral immune response. In some examples, the cellular immune response additionally includes an humoral immune response. The immune response can be specific to the antigenic universal peptide, but this is not required. The immune response that is elicited by administration of the antigenic universal peptide, or nucleic acid encoding the antigenic polypeptide, can be any detectable increase in any facet of the immune response (e.g., cellular response, humoral response, cytokine production), as compared to the immune response in the absence of the administration of the polypeptide or nucleic acid.

Encompassed within the present invention are compositions in association with an antigenic universal peptide, or nucleic acid encoding the polypeptide that elicit the immune response.

As used herein, an "humoral immune response" can refer to an immune response mediated by antibody molecules or immunoglobulins. Antibody molecules of the present invention can include the classes of IgG (as well as subtypes IgG1, IgG2a, and IgG2b), IgM, IgA, IgD, and IgE. Antibodies functionally can include antibodies of a primary immune response as well as memory antibody responses or serum neutralizing antibodies. With respect to infectious disease, antibodies of the present invention can serve to, but are not required to, neutralize or reduce infectivity of the pathogen, and/or mediate antibody-complement, or antibody dependent cell cytotoxicity (ADCC) to the peptide. For more detailed information, see Peptide-Based Immunotherapeutics and Vaccines, Journal of Immunology Research Volume 2014 (2014), which is incorporated by reference herein in its entirety.

As used herein, a "cellular immune response" is one mediated by T-lymphocytes and/or other white blood cells, including without limitation natural killer (NK) cells and macrophages. T-lymphocytes of the present invention include T-cells expressing alpha/beta T-cell receptor subunits or gamma/delta receptor expressing T-cells and may be either effector or suppressor T-cells.

Embodiments as described herein can protect against fungal infections caused by yeast cells, or other microbial infections, such as those caused by bacteria, protozoa, and/or viruses. The outermost layer of the *Candida* yeast cell envelope is the cell wall. The cell wall maintains the structure and the rigidity of the cell but is freely permeable to solutes. Inside the cell wall, the plasma membrane forms a relatively impermeable barrier for hydrophilic molecules. In embodiments, the antigenic universal peptide comprises cell wall peptides, including, for example, fungal cell wall peptides and bacterial cell wall peptides.

In embodiments, the antigenic universal peptide comprises an amino acid sequence, or is encoded by a nucleic acid encoding the amino acid sequence (such as that obtained by reverse translation), corresponding to that of fungal cell wall proteins. Non-limiting examples of fungal cell wall proteins comprise fructose-bisphosphate aldolase (Fba; GenBank Accession No. AOW28947; Protein Accession No. XP_722690), methyltetrahydropteroyltriglutamate homocysteine methyltransferase (Met6; GenBank Access No. AOW30921; Protein Accession No. XP 718219), hyphal wall protein-1 (Hwp1; GenBank Access No. ACN63125), enolase (Eno1; GenBank Accession No. AAA71939), glyceraldehyde-3-phosphate dehydrogenase (Gap1; GenBank Accession No. AOW29704), and phosphoglycerate kinase (Pgk1; GenBank Accession No. AAA66523) as described in Pitarch et al, [Pitarch A, Abian J, Carrascal M, Sanchez M, Nombela C, Gil C (2004) Proteomics-based identification of novel *Candida albicans* antigens for diagnosis of systemic candidiasis in patients with underlying hematological malignancies. *Proteomics* 4:3084-3106], Clancy et al [Clancy C J, Nguyen M-L, Cheng S, Huang H, Fan G, Jaber R A, Wingard J R, Cline C, Nguyen M H (2007) Immunoglobulin G responses against a panel of *Candida albicans* antigens as accurate and early markers for the presence of systemic candidiasis. *J Clin Microbiol* 46:1647-1654], and Pitarch et al, [Prediction of the clinical outcome in invasive candidiasis patients based on molecular fingerprints of five anti-*Candida* antibodies in serum. Mol Cell Proteomics. 2011 January; 10(1):M110.004010. doi: 10.1074/mcp.M110.004010. Epub 2010 Sep. 21], each of which are hereby incorporated by reference in their entireties.

In embodiments, the antigenic universal peptide comprises an amino acid sequence, or is encoded by a nucleic acid encoding the amino acid sequence (such as that obtained by reverse translation), corresponding to that of Fba Protein Accession No. XP_722690; 359 amino acids (SEQ ID NO: 53)

```
  1 mappavlsks gviygkdvkd lfdyaqekgf aipainvtss stvvaaleaa rdnkapiilq
 61 tsqggaayfa gkgvdnkdqa asiagsiaaa hyiraiapty gipvvlhtdh cakkllpwfd
121 gmlkadeeff aktgtplfss hmldlseetd deniatcaky fermakmgqw lemeigitgg
181 eedgvnnehv ekdalytspe tvfavyeslh kispnfsiaa afgnvhgvyk pgnvqlrpei
241 lgdhqvyakk qigtdakhpl ylvfhggsgs tqeefntaik ngvvkvnldt dcqyayltgi
301 rdyvinkiey lkapvgnpeg adkpnkkyfd prvwvregek tmskriaeal difhtkgql
```

In embodiments, the antigenic universal peptide comprises an amino acid sequence, or is encoded by a nucleic acid encoding the amino acid sequence (such as that obtained by reverse translation), corresponding to that of Met6 Protein Accession No. XP_718219; 767 amino acids (SEQ ID NO: 54)

```
  1 myqssylgfp riggqrelkk iteaywsgka tveellakgk elrehnwklq qkagvdiips
 61 ndfsyydqvl dlsllfnaip erytkfdlap idvlfamgrg lqkkatetqa avdvtalemv
121 kwfdsnyhyv rptfshstef klntaagikp vdefneakal gvqtrpvilg pvsylylgka
181 dkdsldlepi sllpkilpvy kellqklkea gaeqvqidep ylvldlpeav qskfkeayda
241 lvgadvpeli lttyfgdvrp nlkaienlpv agfhfdfyry peqldevasi lkdgqtlsag
301 vvdgrniwkt dfakasavvq kaiekvgkdk vvvatsssll htpvdleset kldavikdwf
361 sfatqkldev vviaknvsge dvskqleana asikarsess iindpkvqer lttinealat
421 rkaafperlt eqkakynlpl fptttigsfp qtkdirinrn kfakgqitae eyeafinkei
481 etvvrfqeei gldylvhgep erndmvqyfg eqlngfaftt ngwvqsygsr yvrppiivgd
541 vsrpkamtvk esvyaqsits kpmkgmltgp vtilrwsfpr ddvsgkiqal qlglalrdev
601 ndlegagitv iqvdepaire glplragker sdylnwaaqs frvatsgven stqihshfcy
661 sdldpnhika ldadvvsief skkddpnyiq efseypnhig lglfdihspr ipskqefvsr
721 ieeilkvypa skfwvnpdcg lktrgwpevk esltnmveaa kefraky
```

In embodiments, the antigenic universal peptide comprises an amino acid sequence, or is encoded by a nucleic acid encoding the amino acid sequence (such as that obtained by reverse translation), corresponding to that of Hwp1 Accession No. ACN63125; 264 amino acids (SEQ ID No: 55)

```
  1 sssapattpn tsvpittiet kssstplttt tehdttvvtv tscsnsvcte sevttgvivi
 61 tskdtiytty cpltettpvs tapatetptg tvststeqst tvitvtscse ssctesevtt
121 gvvvvtseet vyttfcplte ntpgtdstpe asippmetip agsqpsipag etspavpksd
181 vpatesapap emtpagtetk paapkssapa tepspvapgt esapagpgas sspkssvlas
241 etspiapgae tapagssgai tipe
```

In embodiments, the antigenic universal peptide comprises an amino acid sequence, or is encoded by a nucleic acid encoding the amino acid sequence (such as that obtained by reverse translation), corresponding to that of Enolase Accession No. AAA71939; 440 amino acids (SEQ ID NO. 56)

```
  1 msyatkihar yvydsrgnpt vevdfttdkg lfrsivpsga stgvhealel rdgdkskwlg
 61 kgvlkavanv ndiiapalik akidvvdqak idefllsldg tpnksklgan ailgvslaaa
121 naaaaaqgip lykhianisn akkgkfvlpv pfqnvinggs haggalafqe fmiaptgvst
181 fsealrigse vyhnlksltk kkygqsagnv gdeggvapdi ktpkealdli mdaidkagyk
241 gkvgiamdva ssefykdgky dldfknpesd pskwlsgpql adlyeqlise ypivsiedpf
301 aeddwdawvh ffervgdkiq ivgddltvtn ptriktaiek kaanalllkv nqigtltesi
361 qaandsyaag wgvmvshrsg etedtfiadl svglrsgqik tgaparserl aklnqilrie
421 eelgseaiya gkdfqkasql
```

In embodiments, the antigenic universal peptide comprises an amino acid sequence, or is encoded by a nucleic acid encoding the amino acid sequence (such as that obtained by reverse translation), corresponding to that of Gap1 Accession No. AOQ29704; 582 amino acids (SEQ ID NO: 57)

```
  1 mlhkketndt fvqlnrspst geqkssgiws sikdsfkpal pqdkltgvdd ipdreltdie
 61 rininaansn lqrklktrhl qmiaigssig tglfvgtgga lstggpaaiv lawaisaisv
121 fmtmqglgel avafpvsggf nlyaskflep gigfavgwny flqffyllpl elvagaitik
181 ywnasinsdv fyiifwfvvl vitmlgvrwy geaelvfcti kviavigfii lgivlicggg
241 pnhefiggky wrepgpfans fkgfasslit aafsfggtem ialtasessn vrhalpkaik
301 qvfwrivify lgsiimiatl vpyndkrllg sssydvtasp ftiaivnggi kglpsvinav
361 ilisvlsvgn asvyatsrtl nslaeqgmap kwtgyidrag rplfailitn vfglfaliaa
421 dnekqvvafn wllalsglss iftwmsinls hirfrramkv qnrsltelpf vaqsgvwgsy
481 fgltlnilyl iaqfyiglfp vggkpnaydf flaylgvpvi laswigykiw krdwtlfira
541 kdidldtgri nvdldllqqe iaeekaqlae kpfyiriyrf wc
```

In embodiments, the antigenic universal peptide comprises an amino acid sequence, or is encoded by a nucleic acid encoding the amino acid sequence (such as that obtained by reverse translation), corresponding to that of Pgk1 Accession No. AAA66523; 417 amino acids (SEQ ID NO: 58)

```
  1 mslsnklsvk dldvagkrvf irvdfnvpld gktitnnqri vaalptikyv eehkpkyivl 61 ashlgrpnge rndkyslapv atelekllgq kytflndcvg pevtkavena kdgeifllen 121 lryhieeegs skdkdgkkvk adpeavkkfr qeltsladvy indafgtahr ahssmvglev 181 pqraagflms keleyfakal enperpflai lggakvsdki qlidnlldkv dmlivgggma 241 ftfkkilnkm pigdslfdea gaknvehlve kakknnveli lpvdfvtadk fdkdaktssa 301 tdaegipdnw mgldcgpksv elfqqavaka ktivwngppg vfefekfangtkslldaavk 361 saengnivii gggdtatvak kygvveklsh vstgggasle llegkdlpgv valsnkn
```

In embodiments, the antigenic universal peptide comprises the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82. In some embodiments, the antigenic universal peptide comprises at least 3, 4, 5, 6, 7, 8, consecutive amino acids of any one of SEQ ID NOS: 1-28. In some embodiments, the antigenic universal peptide comprises at least 60%, 65%, 70%, 75%, 80%, 85%, 90%, 91%, 92% identity to any one of SEQ ID NOS: 1-28, 81-82.

Embodiments as described herein can further comprise multiple antigenic universal peptides covalently linked to each other, such as two or more antigenic universal peptides covalently linked to each other. For example, embodiments can comprise 2, 3, 4, 5, 6, 7, 8, 9, 10, 11, or 12 antigenic universal peptides covalently linked. One or more of the linked antigenic universal peptides can be at least 80% identical in two or more different microorganisms.

Examples of antigenic peptides covalently linked to each other comprise SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93.

Embodiments as described herein can comprise peptides linked in different orders and orientations. For example, the linked construct can comprise NH$_3$-PEPTIDE1-Linker-PEPTIDE2-COOH or NH$_3$-PEPTIDE2-Linker-PEPTIDE1-COOH.

In certain embodiments, the order of the linked peptides may not be relevant to the protective efficacy of the peptide vaccine. For example, the covalently linked universal peptide can comprise NH$_3$-(SEQ ID NO: 1)-KK-(SEQ ID NO: 14)-COOH or NH$_3$-(SEQ ID NO: 14)-KK-(SEQ ID NO. 1)-COOH, each of which having similar protective efficacy.

In other embodiments, the order of the linked peptides is important for the protective efficacy of the vaccine, such as is the case when one construct protects against infection more effectively than another construct. For example, NH$_3$-PEP1-KK-PEP2-COOH works better than NH$_3$-PEP2-KK-PEP1-COOH, even though NH$_3$-PEP2-KK-PEP1-COOH itself can induce moderate protection (~40%-50% survival).

In embodiments, the antigenic universal peptides are covalently linked by a linker, such as a peptide linker. Non-limiting examples of such peptide linkers comprise the amino acid sequence KK (SEQ ID NO: 49), GPSL (SEQ ID NO: 50), a universal CD4 T cell helper peptide, also known as non-natural pan DR epitope or PADRE (SEQ ID NO: 51): aKXVAAWTLKAAaZC (X=1-cyclohexylalanine, Z=aminocaproic acid). In embodiments, the linker is a helical linker (such as EAAAK; SEQ ID NO: 76), wherein in other embodiments the linker is a flexible linker (such as GGGGS; SEQ ID NO: 77). Examples of antigenic peptides covalently linked to each other comprise SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, or SEQ ID NO: 93.

EAAAK (SEQ ID NO: 76) is an alpha helix-forming linker which can be used as a linker in fusion proteins. The α-helical structure is rigid and stable, with intra-segment hydrogen bonds and a closely packed backbone. Thus, stiff α-helical linkers, such as EAAAK (SEQ ID NO: 76), can act as rigid spacers between protein domains, maintaining the structure of the epitope intact, especially binding sites. Also, EAAAK (SEQ ID NO: 76) motif can effectively separate functional domains.

GGGGS (SEQ ID NO: 77) linker is a flexible linker (GGGGS)$_n$ (SEQ ID NO: 77) (Huston J et al. Protein engineering of antibody binding sites: recovery of specific activity in an anti-digoxin single-chain Fv analogue produced in *Escherichia coli*. Proc Natl Acad Sci USA. 1988; 85:5879-5883, incorporated herein by reference in its entirety) that can be used to construct an antibody fragment, such as scFv, since its flexible structure allows for the correct orientation of the V$_H$ and V$_L$ domains and does not interfere with the folding of the protein domains.

In certain embodiments, the peptide comprises two or more linkers, further including combinations of helical and flexible linkers. For example, embodiments can comprise both RGD (SEQ ID NO 52) and KK (SEQ ID NO. 49) in chimeric-peptide vaccines, such as those comprise an Fba peptide and a Met6 peptide, such as RGD-(SEQ ID NO: 26)-KK-(SEQ ID NO: 1)-KLH.

GPSL (SEQ ID NO: 50) is a 4 amino acid linker that functions as a flexible linker joining the B cell and the T cell epitopes of the vaccine without transporting structural information to the other part. Without wishing to be bound by theory, the GPSL unit connects the two or more parts of the peptide vaccine without transferring any structural information from one part to the other. For example, see Structural Characterization by NMR of a Double Phosphorylated Chimeric Peptide Vaccine for Treatment of Alzheimer's Disease Molecules 2013, 18, 4929-4941, which is incorporated by reference herein in its entirety.

Embodiments as described herein can comprise universal T cell epitope, such as TT830-844 (QYIKANSKFIGITE; SEQ ID NO: 75) or TT947-967 (FNNFTVSFWLRVPKVSASHLE; SEQ ID NO: 78).

The production of antibodies directed to and/or that recognize epitopes in the antigenic universal peptides of the invention, such as those described herein, can be increased significantly by introducing a di-lysine spacer (KK; SEQ ID NO: 49). Cathepsin B, one of the important proteases for antigen processing in the context of MHC class II molecules, digests the di-lysine amino acid sequence. Without wishing to be bound by theory, the reduction in antibody production to the newly generated epitope by tandem repeating of peptides is related to the digestion of the spacer by the protease. Peptides with an RGD motif at the N-terminal side of the -KK-linker strongly induced the antibodies to the peptides derived from the C-terminus of the KK linker of the antigenic universal peptide. However, only minimal levels of peptide antibodies were induced when the determinant was on the N-terminal side of the KK linker. The KK linker greatly reduced the induction of the antibodies that could recognize the KK including regions. (RGD motif enhances immunogenicity and adjuvanicity of peptide antigens following intranasal immunization; Vaccine 22 (2003) 237-243, which is incorporated by reference herein in its entirety).

The insertion of two lysine residues at the boundary of a B-cell epitope and a class II presentable peptide (T-cell epitope) enhances the antibody induction capacity of this type of peptide construct. Pairs of basic residues such as KK, KR and RR appeared to be the main cleavage site of cathepsin B, one of the most important enzymes for antigen processing in the context of class II molecules.

RGD enhances the immunogenicity of peptide antigens by addition of motifs that bind to cell attachment proteins, such as arginine-glysine-aspartate (RGD), to the amino acid sequence. RGD, an integrin-binding motif, is the strongest, among several molecules reported, giving an average of 10 times enhancement of antibody titers when incorporated into several peptide antigens. (*RGD motif enhances immunogenicity and adjuvanicity of peptide antigens following intranasal immunization; Vaccine* 22 (2003) 237-243, which is incorporated herein by reference in its entirety).

The pan HLA DR-binding epitope (PADRE; SEQ ID NO: 51) is a simple carrier epitope suitable for use in the development of synthetic and recombinant vaccines. Since PADRE (SEQ ID NO: 51) is capable of binding to murine I-$A^b$ molecules, it was possible to evaluate the in vivo immunogenicity of simple linear constructs using PADRE (SEQ ID NO: 51) as a T helper epitope in conjunction with various *Candida* B cell peptide epitopes. This epitope is a synthetic, non-natural pan HLA DR-binding Epitope (PADRE) (SEQ ID NO: 51) peptide that binds with high or intermediate affinity to 15 of 16 of the most common HLA-DR types tested to date. (Linear PADRE (SEQ ID NO: 51) T Helper Epitope and Carbohydrate B Cell Epitope Conjugates Induce Specific High Titer IgG Antibody Responses; The Journal of Immunology, 2000, 164: 1625-163, which is incorporated by reference herein in its entirety).

In embodiments, an antigenic universal peptide of the invention can comprise a polypeptide comprising at least 2 or more covalently linked antigenic universal peptides, wherein each antigenic universal peptide is at least 80% identical in two or more different microorganisms. For example, the antigenic universal peptides can be at least 3, 4, 5, 6, 7, 8, 9, 10, 11, 12, 13, 14, 15, 16, 17, 18, 19, 20, 21, 22, 23, 24, 25 or greater than 25 amino acids in length comprising peptides corresponding to fructose-bisphosphate aldolase (Fb a), methyltetrahydropteroyltriglutamate homocysteine methyltransferase (Met6), hyphal wall protein-1 (Hwp1), enolase (Enol), glyceraldehyde-3-phosphate dehydrogenase (Gap1), and phosphoglycerate kinase (Pgk1).

In embodiments, chimeric peptides, such as those comprising the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82 comprises a helical linker (such as EAAAK; SEQ ID NO: 76), a flexible linker (such as GGGGS; SEQ ID NO: 77), and/or at least one covalent linker selected from the group consisting of KK (SEQ ID NO: 49), GPSL (SEQ ID NO: 50), a universal CD4 T cell helper peptide (also known as non-natural pan DR epitope (PADRE) (SEQ ID NO: 51).

In other embodiments, the chimeric peptide can comprise an antigenic universal peptides covalently linked to a peptide of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, or SEQ ID NO: 48. Such embodiments, for example, can comprise a helical linker (such as EAAAK; SEQ ID NO: 76), a flexible linker (such as GGGGS; SEQ ID NO: 77), and/or at least one covalent linker selected from the group consisting of KK (SEQ ID NO: 49), GPSL (SEQ ID NO: 50), a universal CD4 T cell helper peptide (also known as non-natural pan DR epitope (PADRE) (SEQ ID NO:51). For a discussion of peptides for fungal infections, see also U.S. Pat. No. 9,416,173, which is incorporated by reference herein in its entirety.

In embodiments, the antigenic universal peptide can be modified to be used as a vaccine in a mammal. For example, modification can include methylation, amidation, acetylation, PEGylation etc. Such modifications can be modifications of the N terminus, the C terminus, and/or internal to the peptide. Such modifications can be carried out onto one or more amino acids of an antigenic universal peptide of the invention. For example, modifications of the antigenic universal peptide can increase the peptide's stability in vivo, elicit a stronger immune response, or allow the peptide to imitate its natural structure.

In embodiments, the peptide modification can be methylation. The methylation of proteins, for example, can help regulate cellular functions such as transcription, cell division, and cell differentiation. Methylation of the antigenic universal peptides, for example, can extend the half-life of the peptides, and can also be used to identify the binding sites of peptides with antibodies. Methylation of amino acid residues can be performed according to methods well understood by one of ordinary skill in the art (see US20090264620 and Mini Rev Med Chem. 2016; 16(9):683-90, each of which are incorporated by reference herein in their entireties entirety).

Without being bound by theory, an important aspect of using a methylated peptide is the role this modification plays in the regulation of protein-protein interactions. The methylation of peptides can either inhibit or promote peptide-antibody interactions, depending on the type of methylation (Lee, Young-Ho, and Michael R. Stallcup. "Minireview: protein arginine methylation of nonhistone proteins in transcriptional regulation." *Molecular endocrinology* 23.4 (2009): 425-433.; Poornima, Gopalakrishna, et al. "Arginine methylation promotes translation repression activity of eIF4G-binding protein, Scd6." *Nucleic Acids Research* (2016): gkw762.; Bedford, Mark T., et al. "Arginine methylation inhibits the binding of proline-rich ligands to Src homology 3, but not WW, domains." *Journal of Biological Chemistry* 275.21 (2000): 16030-16036, each of which are incorporated herein by reference in their entireties). In one embodiment, each amino acid residue of the universal peptide is methylated. In subsequent embodiments, these methylated peptides are tested for their binding affinity to the monoclonal antibodies specific for the original, unmethylated peptide antigen. Also, the specificity and binding affinity of methylated peptide to these mAbs are compared with that of the original, unmethylated, peptide in order to understand which amino acid is the key for the peptide and antibody binding.

In embodiments, the peptide modification can be amidation or acetylation, such as at the C terminus or N terminus, respectively. As the antigenic universal peptide can be that of an internal amino acid sequence of a protein, terminal amidation (such as that of the C-terminus) or acetylation (such as that of the N-terminus) of the peptide will remove the charge of the peptide and help it imitate its natural structure. In other words, the modified peptide termini are uncharged, allowing the modified peptide to more closely mimic that of the native protein. Such modifications can also increase the metabolic stability of the peptides, as well as their ability to resist enzymatic degradation by aminopeptidases, exopeptidases, and synthetases. Amidation and acetylation of amino acid residues can be performed according to methods well understood by the skilled artisan, for example see Cottingham, Ian R., et al. "A method for the amidation of recombinant peptides expressed as intein fusion proteins in *Escherichia coli.*" Nature biotechnology 19.10 (2001): 974-977, Cerovsky, Václav, and Maria-Regina Kula. "Peptide amidase-catalyzed C-terminal peptide amidation in a mixture of organic solvents." *Peptides for the New Millennium* (2002): 142-143; Mura, Manuela, et al. "The effect of amidation on the behaviour of antimicrobial peptides." *European Biophysics Journal* 45.3 (2016): 195-207; Thomas, A., Towards a Functional Understanding of Protein N-Terminal Acetylation. *PLOS Biol.* 2011, 9(5); and Wallace, R. J., Acetylation of peptides inhibits their degradation by rumen microorganisms. *British Journal of Nutrition.* 1992, 68, 365-372, each of which are incorporated by reference in their entireties.

In embodiments, the peptide modification can be acetylation, for example N-terminal acetylation (see U.S. Pat. No. 9,062,093, which is incorporated herein by reference in its entirety). Peptides such as those described herein can be derived from either the N- or C-terminus of cell wall proteins, but are still considered internal peptides of the cell wall proteins and not necessarily at the extreme end of the N- or C-terminus of the proteins. When the peptide is from an internal sequence of a protein, terminal amidation (C-terminus) or acetylation (N-terminus) will remove its charge and help it imitate its natural structure (amide, $CONH_2$). In addition, this modification makes the resulting peptide more stable towards enzymatic degradation resulting from exopeptidases.

In embodiments, the peptide modification can be PEGylation, or linking of the antigenic universal peptides to polyethylene glycol, so as to increase solubility and prolong circulatory time, for example. Once linked to a peptide, the PEG subunit becomes tightly associated with two or three water molecules, which has the dual function of rendering the antigenic universal peptide more soluble in water and making its molecular structure larger. As the kidneys filter substances according to size, the addition of PEG's molecular weight can prevent the premature renal clearance undergone by small peptides. PEG's globular structure can also act as a shield to protect the antigenic universal peptide of the invention from proteolytic degradation, and can reduce the immunogenicity of foreign peptides by limiting their uptake through the dendritic cells. PEG itself is not immunogenic or toxic, and allows for lower doses and less-frequent administrations. In some instances, PEG can increase the circulating half-life of a peptide drug by more than 100 times. In addition to improving the pharmacokinetic and pharmacodynamic properties of peptide drugs once inside the body, PEGylation can also aid drug delivery because PEGylated peptides act as permeation enhancers for nasal drug delivery.

In embodiments, the PEG molecule can be monomethoxy PEG (mPEG), which has relatively simple chemistry due to its monofunctionality ($CH_3O-(CH_2CH_2O)n-CH_2CH_2-OH$). In other embodiments, the PEG molecule can be HiPEG, or PEG attached to histidine sequences expressed on the N or C terminal of proteins. For example, 6 His-tags can be used to create site-specific PEGylated conjugates, that is, PEGylation using a His-tagging approach. A protein is encoded with a polyhistidine tag (such as a 6 histidine tag). Once incubated with a Ni-nitrilotriacetic acid (NTA)-PEG reagent, a complex is formed between the histidine residues and the nickel ion, thus PEGylating the protein. In other embodiments, the PEG molecule can be branched or forked PEG, such as PEG2, releasable PEGs (rPEGs), or heterbifunctional PEGs, details of which can be found in Roberts, et al, which is incorporated by reference herein in its entirety (Roberts, M. J., M. D. Bentley, and J. M. Harris. "Chemistry for peptide and protein PEGylation." *Advanced drug delivery reviews* 64 (2012): 116-127). One of ordinary skill in the art appreciates the routine methods practiced to pegylate amino acid residues of peptides of interest.

In embodiments, a cysteine residue can be incorporated onto the C-terminus and/or N-terminus of the antigenic universal peptide, allowing for conjugation of the peptide to other components, for example carrier proteins such as KLH, BSA, or TT. Methods of incorporating cysteine residues are well understood in the art (e.g., see Chapter 3 Peptide-carrier conjugation: Laboratory Techniques in Biochemistry and Molecular Biology; Volume 19, 1988, Pages 95-130).

In embodiments, the antigenic universal peptide can be conjugated to a macromolecule, non-limiting examples of which comprise carrier proteins such as keyhole limpet hemocyanin (KLH), tetanus toxoid (TT), or bovine serum albumin (BSA). Conjugation of the peptide to such molecules, for example, can increase the stability of the peptide, or can increase resistance to proteolytic cleavage. Conjugation methods as listed herein are well understood by the skilled artisan (Chapter 3 Peptide-carrier conjugation: Laboratory Techniques in Biochemistry and Molecular Biology; Volume 19, 1988, Pages 95-130).

"Conjugation" can refer to the linking of a peptide, either directly or indirectly, to another molecule. For example, "direct conjugation" can refer to linking of the antigenic universal peptide to an activated carbohydrate, another antigenic universal peptide, or a peptide linker, without introducing additional functional groups. As another example, "indirect conjugation" can refer to the addition of functional groups which are used to facilitate conjugation. For example, carbohydrate can be functionalized with amines which are subsequently reacted with bromoacetyl groups. The bromoacetylated carbohydrate is then reacted with thiolated protein. (Hermanson, G T, Bioconjugate Techniques, Academic Press, $2^{nd}$ ed, 2008). The term "functionalization" generally means to chemically attach a group to add functionality, for example, to facilitate conjugation. Examples include functionalization of proteins with hydrazides or aminooxy groups and functionalization of carbohydrate with amino groups.

In embodiments, the antigenic universal peptide of the invention can comprise a Multiple Antigenic universal peptide (MAP), which can allow for the production of high-titer anti-peptide antibodies (Fujita and Taguchi, Chemistry Central Journal 2011, 5:48 Proc. Natl. Acad. Sci. USA Vol. 85, pp. 5409-5413, August 1988, which is incorporated by reference herein in its entirety). Multiple antigen peptide application can be used to produce high-titer anti-peptide antibodies and synthetic peptide vaccines. This system utilizes the α- and ε-amino groups of lysine to form a backbone to which multiple peptide chains can be attached. Depending on the number of lysine tiers, different numbers of peptide branches can be synthesized. This eliminates the need to conjugate the antigen to a protein carrier. MAP is a branched peptide at which linear peptide chains are linked at their C-terminus via polylysine core, thereby increasing the size of whole molecule. For example, 4MAP-peptide refers to four branches of peptide sequences with 3 lysine cores. For the synthesis of MAPs and MAP-based systems, please refer to Kowalczyk, Wioleta, et al. "Synthesis of multiple antigenic peptides (MAPs)—strategies and limitations." *Journal of Peptide Science* 17.4 (2011): 247-251; Tam, James P. "Synthetic peptide vaccine design: synthesis and properties of a high-density multiple antigenic peptide system." *Proceedings of the National Academy of Sciences* 85.15 (1988): 5409-5413; Fujita, Yoshio, and Hiroaki Taguchi. "Current status of multiple antigen-presenting peptide vaccine systems: Application of organic and inorganic nanoparticles." *Chemistry Central Journal* 5.1 (2011): 48, each of which are incorporated herein by reference in their entireties.

Multiple Antigenic universal peptides (MAPS) are peptides that are branched artificially, in which Lys residues are used as the scaffolding core to support the formation branches, for example 1, 2, 3, 4, 5, 6, 7, 8, 9, 10 or greater than 10 branches, with varying peptide sequences or the same peptide sequences. Multiple Antigen Peptides have been used

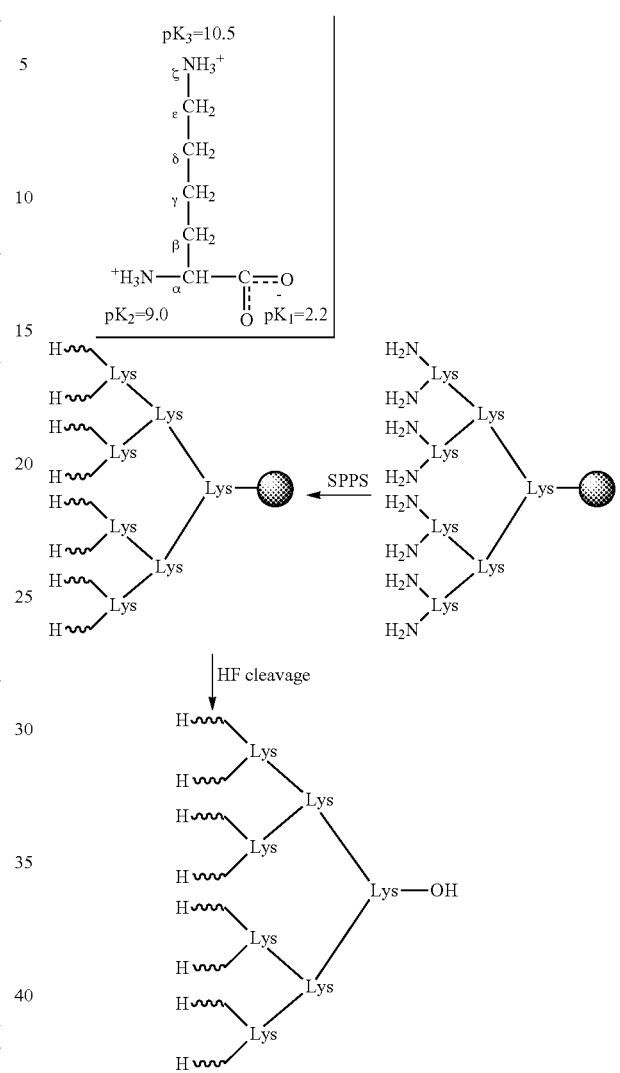

to produce antibodies for use in immunological studies. MAPs have a high molar ratio of the peptide antigen to the core molecule, and no carrier protein is needed to elicit an antibody response.

Standard SPSS can be used to synthesize MAPs. This process involves anchoring Boc-Lys(Boc)-OH to a resin, followed by the sequential treatment with TFA, deprotection, coupling, and deprotection cycles. The peptides to be used in immunological studies are then synthesized on each branch. For the synthesis of MAPs and MAP-based systems, please refer to Kowalczyk, Wioleta, et al. "Synthesis of multiple antigenic peptides (MAPs)—strategies and limitations." *Journal of Peptide Science* 17.4 (2011): 247-251; Tam, James P. "Synthetic peptide vaccine design: synthesis and properties of a high-density multiple antigenic peptide system." *Proceedings of the National Academy of Sciences* 85.15 (1988): 5409-5413; Fujita, Yoshio, and Hiroaki Taguchi. "Current status of multiple antigen-presenting peptide vaccine systems: Application of organic and inorganic nanoparticles." *Chemistry Central Journal* 5.1 (2011): 48, each of which are incorporated herein by reference in their entireties.

The synthesis of an MAP by chemical ligation

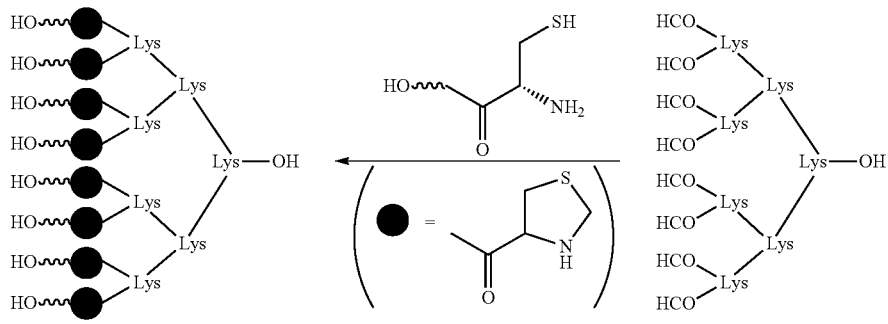

There are no known branched proteins in nature. However, the synthesis of MAP can be problematic. The strict spacing between each of the eight branches might lead to aggregation of the peptides on the resin, and could result in low coupling yields and peptide deletions. The PeptideSyn technology used by LifeTein (https://www.lifetein.com/multiple-antigenic-peptides.html), for example, overcomes this problem using a chemical ligation strategy, which allows production of the desired peptide dendrimer at an increased yield. The branched structures can then form an increased molecular weight protein to elicit an immunogenic response.

MAP peptides perform like large proteins as four or eight copies of antigenic universal peptides of interest, for example, are synthesized on a branched lysine.

MAP peptides comprising the antigenic universal peptides of the invention can be injected directly with an adjuvant for antibody production. A carrier protein is not required.

The MAP technique favors N-terminal or internal peptides because the peptide is linked through the C-terminus. In contrast, KLH-conjugation favors C-terminal peptides. However, the KLH carrier might cause steric hindrance.

Without wishing to be bound by theory, MAP peptides can result in a slightly higher titer than KLH-conjugated peptides due to their structure. The MAP design maximizes the antigen concentration because the synthesized peptide-antigen accounts for up to 95% of the total weight of the final product.

With MAPs, a known amount of peptide can be used for immunization each time, giving greater control over the experimental conditions.

Embodiments as described herein further comprise methods for selecting a peptide vaccine directed to microbial infections. For example, one embodiment comprises aligning the amino acid sequences of two or more proteins, such as cell wall proteins as described herein, and selecting or identifying a peptide sequence, such as those of at least 7-9 consecutive amino acids, wherein the amino acid sequence is at least 70% identical in the two or more cell surface proteins.

Embodiments further comprise the steps of analyzing the hydrophilicity of each amino acid and of the peptide, as well as the score of antigenicity. Hydrophilic peptides tend to appear on the cell surface, which is the first contacting immune cells. Hydrophilic peptides can be the target for vaccine candidates as they score higher for their antigenicity.

Vaccine Composition

The term "vaccine" refers to a composition or compound (e.g., an antigen) used to stimulate an immune response in a mammal and so confer resistance to the disease or infection in that mammal, including an ability of the immune system to remember the previously encountered antigen. Antibodies are produced as a result of the first exposure to an antigen and stored in the event of subsequent exposure.

Embodiments as described herein are directed to a vaccine composition comprising at least one antigenic universal peptide comprising any one of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82 or a combination thereof, and a pharmaceutically acceptable carrier. In some embodiments, the vaccine composition comprises at least one antigenic universal peptide encoded by a nucleic acid, such as a nucleic acid encoding for any one of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82 and a pharmaceutically acceptable carrier. In some embodiments, the vaccine composition comprises at least one antigenic universal peptide encoded by a nucleic acid harbored by vector for expression of the same, and a pharmaceutically acceptable carrier. The term "pharmaceutically acceptable carrier" can refer to a one or more compatible solid or liquid filler diluents or encapsulating substances which are suitable for administration to a mammal, preferably a human. Typically, the carrier may be a solid, liquid, solution, suspension, gel, ointment, lotion, or combinations thereof as further discussed herein.

In embodiments, the vaccine composition can comprise two or more antigenic universal peptides of the invention, such as two or more antigenic universal peptides as described herein. Embodiments can comprise 1, 2, 3, 4, 5, 6, 7, 8, 9, 10, 11, or 12 antigenic universal peptides, including those as described herein, non-limiting examples of which comprise the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82.

In other embodiments, the vaccine composition can further comprise a peptide of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, or SEQ ID NO: 48.

"Adjuvant" can refer to a pharmacological or immunological agent that can be added to a vaccine composition to modify the immune response by boosting it such as to give a higher amount of antibodies and longer-lasting protection, thus minimizing the amount of foreign material to be administered to a subject. Adjuvants can also be used to enhance the efficacy of a vaccine by helping to modify the immune response to particular types of immune system cells: for example, by activating T cells instead of antibody-secreting B cells depending on the purpose of the vaccine. Adjuvants can also be used in the production of antibodies from immunized animals. There are different classes of adjuvants that can push immune response in different directions, but the most commonly used adjuvants include aluminum hydroxide and paraffin oil. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); Ribi-R730; Adjuplex (Wegmann et al, *Clin Vaccine Immunol.* 2015 September; 22(9):1004-12, incorporated herein by reference in its entirety); AS-2 (Smith-Kline Beecham); QS-21 (Aquilla); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

In embodiments, the vaccine composition can optionally comprise an adjuvant, whereas in other embodiments the vaccine composition does not comprise an adjuvant. Peptide vaccines without need for an adjuvant can maintain their protective efficacy while limiting the adverse effects that are associated with adjuvants, such as aluminum based adjuvants. For example, aluminum adjuvants can induce serious immunological disorders in humans, such as risk for autoimmunity, long-term brain inflammation and associated neurological complications, and can have profound and widespread adverse health consequences (Tomljenovic, L., and C. A Shaw. "Aluminum vaccine adjuvants: are they safe?." *Current medicinal chemistry* 18.17 (2011): 2630-2637 and Petrovsky, Nikolai, and Julio César Aguilar. "Vaccine adjuvants: current state and future trends." *Immunology and cell biology* 82.5 (2004): 488-496, each of which are incorporated by reference herein in their entireties).

Embodiments as described herein can comprise a T helper epitope for generating an immune response. In embodiments, the T helper epitope comprises pan DR-binding epitope (PADRE) (SEQ ID NO: 51), and/or an RGD motif. RGD, for example, enhances the immunogenicity of a peptide antigen by addition of motifs that bind to cell attachment proteins. RGD provides an average of 10 times enhancement of antibody titers when incorporated into peptide antigens, such as the antigenic universal peptides of the invention. Other T helper epitopes comprise TT946-967 (FNNFTVSFWLRVPKVSASHLE; SEQ ID NO: 78) and/or TT830-844 (QYIKANSKFIGITE; SEQ ID NO: 75), which belongs to 830 to 844 or 946 to 967 amino acid sequence of the tetanus toxin Tc, human, common for most MHC molecules.

Embodiments as described herein, such as the antigenic universal peptide or composition comprising the same, can optionally comprise a protein carrier. A protein carrier can be a protein, a polypeptide, or fragment thereof that is coupled or conjugated to an antigenic universal peptide as described herein. In some embodiments, the protein carrier can be included with the vaccine composition of the invention. The protein carrier can be used to enhance the immunogenicity of the antigenic universal peptide or vaccine composition to a greater degree than the peptide or composition alone. For example, the protein carrier can serve as a T-dependent antigen which can activate and recruit T-cells and thereby augment T-cell dependent antibody production.

Non-limiting examples of protein carriers comprise bacterial toxoids, toxins, exotoxins, and nontoxic derivatives thereof, such as tetanus toxoid, tetanus toxin Fragment C, diphtheria toxoid, CRM (a nontoxic diphtheria toxin mutant) such as CRM 197, cholera toxoid, *Staphylococcus aureus* exotoxins or toxoids, *Escherichia coli* heat labile enterotoxin, *Pseudomonas aeruginosa* exotoxin A, including recombinantly produced, genetically detoxified variants thereof; bacterial outer membrane proteins, such as *Neisseria meningitis* serotype B outer membrane protein complex (OMPC), outer membrane class 3 porin (rPorB) and other porins; keyhole limpet hemocyanine (KLH), hepatitis B virus core protein, thyroglobulin, albumins, such as bovine serum albumin (BSA), human serum albumin (HSA), and ovalbumin; pneumococcal surface protein A (PspA), pneumococcal adhesin protein (PsaA); purified protein derivative of tuberculin (PPD); transferrin binding proteins, polyamino acids, such as poly(lysine:utamic acid); peptidyl agonists of TLR-5 (e.g. flagellin of motile bacteria like *Listeria*); and derivatives and/or combinations of the above carriers. Preferred carriers for use in humans include tetanus toxoid, CRM 197, and OMPC. For a review of characteristics, development, and clinical trials of protein carrier of conjugate vaccines, please refer to Pichichero, Michael E. "Protein carriers of conjugate vaccines: characteristics, development, and clinical trials." *Human vaccines & immunotherapeutics* 9.12 (2013): 2505-2523, which is incorporated by reference in its entirety herein.

Vaccine compositions as described herein can further comprise therapeutic and/or prophylactic agents, such as one or more antimicrobial agents. For example, the antimicrobial agent can comprise an anti-fungal agent, an anti-viral agent, an anti-bacterial agent, and/or an anti-protozoal agent.

Antifungal compounds can be organized into several groups: polyene antifungals, azoles, allylamines, echinocandins, and other antifungal compounds. Examples of polyene antifungals (compounds with multiple conjugated double bonds) include amphotericin B, candicidin, nystatin, natamycin, and rimocidin. Examples of commonly used azoles (compounds with five-membered organic rings) include fluconazole, itraconazole, ketoconazole, miconazole, and clotrimazole. Examples of allyamines (compounds that inhibit ergosterol synthesis by inhibiting squalene synthesis) include naftifine, terbinafine and amorolfine. Echinocandins (compounds that inhibit the synthesis of glucan in the cell wall) include anidulafungin, caspofungin, and micafungin. Other commonly used antifungal compounds include griseofulvin and 5-fluorocytosine. Non-limiting examples of anti-viral agents comprise TFT, Acyclovir, gancyclovir, penciclovir, cidofovir; ribavirin, interferon, phosphonoacetate, Foscarnet, amantadine, Rimatidine, oseltamivir, Valacyclovir, Valgancyclovir, Peramivir, Zanamivir, ora combination thereof.

Non-limiting examples of anti-bacterial agents comprise aminoglycosides, fluoroquinolones, beta-lactams, macrolide, and tetracyclines.

Non-limiting examples of anti-protozoal agents comprise chloroquine, pyrimethamine, mefloquine, hydroxychloroquine, metronidazole, atovaquone, or a combination thereof.

Antibodies

The protective role of antibodies against fungal infections such as *Candida* has been controversial, but the evidence is mounting in favor for this mode of protection. As a prevention strategy, protection against disease may be actively or passively acquired by vaccination and transfer of preformed antibodies (e.g., monoclonal antibodies), respectively. As a therapeutic measure, experimental evidence indicates that preformed antibodies can enhance the effectiveness of antifungal agents.

Embodiments as described herein comprise an isolated antibody or binding fragment thereof that specifically binds to an antigenic universal peptide, for example that with an amino acid sequence that is at least 80% identical in two or more different microorganisms. Examples of such functional antibody fragments include, but are not limited to, $F_v$, single chain $F_v$ (scFv), complementarity determining regions (CDRs), $V_L$ (light chain variable region), $V_H$ (heavy chain variable region), Fab, F(ab')$_2$, minibody, diabody, and any functional portion of an immunoglobulin peptide capable of binding to target antigen. Non-limiting examples of such peptides are described herein and can comprise those of fructose-bisphosphate aldolase (Fba; GenBank Accession No. AOW28947; Protein Accession No. XP_722690), methyltetrahydropteroyltriglutamate homocysteine methyltransferase (Met6; GenBank Access No. AOW30921; Protein Accession No. XP_718219), hyphal wall protein-1 (Hwp1; GenBank Access No. ACN63125), enolase (Enol; GenBank Accession No. AAA71939), glyceraldehyde-3-phosphate dehydrogenase (Gap1; GenBank Accession No. AOW29704), and phosphoglycerate kinase (Pgk1; GenBank Accession No. AAA66523), such as the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82.

An antibody is a large, Y-shaped glycoprotein produced mainly by plasma cells that is used by the immune system to neutralize pathogens. It belongs to the immunoglobulin superfamily and consists of two identical heavy chains and two identical light chains, and each chain further comprising a variable region (Fv) and a constant region (Fc). Five major antibody classes have been identified and include: IgA, IgD, IgE, IgG and IgM. This classification is based on differences in amino acid sequence in the constant region (Fc) of the antibody heavy chains. Based on differences in the amino acid sequence in the light chain Fc, immunoglobulins can be further classified by the type of light chain (e.g., kappa light chain ($LC_\kappa$) or lambda light chain ($LC_\lambda$)). The ratio of these two light chains differs greatly among species, but the light chains are always either both kappa or both lambda.

The term "antibody" can refer to polyclonal and monoclonal antibodies and derivatives thereof (for example chimeric, humanized, and fully human antibodies). An antibody, for example, can include an immunoglobulin molecule (such as IgG (as well as subtypes IgG1, IgG2a, and IgG2b, IgG3, IgG4), IgM, IgA (as well as subtypes IgA1 and IgA2), IgD, and IgE or any functional fragment of an immunoglobulin molecule which binds to the target antigen and or combinations thereof. Examples of such functional antibody fragments include, but are not limited to, $F_v$, single chain $F_v$ (scFv), complementarity determining regions (CDRs), $V_L$ (light chain variable region), $V_H$ (heavy chain variable region), Fab, F(ab')$_2$, minibody, diabody, and any functional portion of an immunoglobulin peptide capable of binding to target antigen.

Antibodies exist, e.g., as intact immunoglobulins or as a number of well characterized antibody fragments produced synthetically or by digestion with various peptidases. Thus, for example, pepsin digests an antibody below the disulfide linkages in the hinge region to produce F(ab')$_2$a dimer of Fab, which itself is a light chain joined to $V_H$—$C_{H1}$ by a disulfide bond. The F(ab')$_2$ may be reduced under mild conditions to break the disulfide linkage in the hinge region, thereby converting the F(ab')$_2$ dimer into an Fab$^1$ monomer. The Fab$^1$ monomer is essentially an Fab with part of the hinge region (see, FUNDAMENTAL IMMUNOLOGY, 3RD ED., W. E. Paul, ed, Raven Press, N.Y. (1993), which is incorporated herein in its entirety). While various antibody fragments are defined in terms of the digestion of an intact antibody, one of skill in the art will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

An antibody can be "reactive with" or "bind to" an antigen if it interacts with the antigen. This interaction is analogous to a chemical reaction in which two reactants come together to form a product. In the case of the antibody-antigen interaction, the product of the interaction is an antibody-antigen complex. Such antigen-antibody interactions can be measured by surface plasmon resonance, binding affinity assays, ELISA, Western blot, Immunofluorescence, or fluorescence-activated cell sorting (FACS) analysis.

The term "humanized" refers to an antibody wherein the constant regions have at least about 80% or greater homology to a human immunoglobulin. Additionally, some of the nonhuman, such as murine, variable region amino acid residues can be modified to contain amino acid residues of human origin.

Humanized antibodies can be referred to as "reshaped" antibodies. Manipulation of the complementarity-determining regions (CDR) is a way of achieving humanized antibodies. See, for example, Jones, et al., *Nature* 321:522 (1988) and Riechmann, et al., *Nature* 332:323 (1988), both of which are incorporated by reference herein. For a review article concerning humanized antibodies, see Winter & Milstein, *Nature* 349:293 (1991), incorporated by reference herein. In some embodiments, the antibodies of the invention can be humanized according to methods well known in the art, for example by modifying the amino acids of CDR regions to amino acid residues of human origin. Humanized monoclonal antibodies can also be made using the XenoMouse transgenic animal as described in U.S. Pat. No. 5,939, 598, or using methods as described in US 20140004123 or EP 2003960, each of which are hereby incorporated by reference in their entireties.

The term "fully human" refers to an antibody wherein the constant regions are homologous to a human immunoglobulin. Additionally, the variable region amino acid residues are amino acid residues of human origin. Fully human antibodies can be generated using Complementarity-determining region (CDR) engraftment (N. R. Gonzales et al., *Mol. Immunol.* 41, 863-872 (2004); S. V. Kashmiri et al., *Methods* 36, 25-34 (2005); and J. Osbourn, M. Groves, and T. Vaughan, *Methods* 36, 61-68 (2005)); transgenic mice with human immunoglobulin genes (D. M. Fishwild et al., *Nat. Biotechnol.* 14, 845-851 (1996); L. L. Green, *J. Immunol. Methods* 231, 11-23 (1999); L. L. Green et al., *Nat. Genet.* 7, 13-21 (1994); A. Schedl et al., *Nucleic Acids Res.* 20, 3073-3077 (1992); A. Schedl et al., *Nucleic Acids Res.* 21, 4783-4787 (1993); A. Schedl et al., *Nature* 362, 258-261 (1993); and L. M. Weiner, *J. Immunother.* 29, 1-9 (2006)); and/or phage, yeast, or ribosome display technologies (J. Osbourn, M. Groves, and T. Vaughan, *Methods* 36, 61-68 (2005)).

A chimeric antibody is an antibody made by fusing the antigen binding region (for example, the variable domains of the heavy and light chains, VH and VL) from one species like a mouse, with the constant domain (effector region) from another species such as a human. In some embodiments, a chimeric antibody comprises human (or humanized) VH and VL regions, and the Fc region of a mouse. The chimeric antibodies retain the original antibody's antigen specificity and affinity.

The terms "isolated" or "substantially purified," for example when applied to a protein such as an antibody, denotes that the protein is essentially free of other cellular components with which it is associated in the natural state. It is preferably in a homogeneous state, although it can be in either a dry or aqueous solution. Purity and homogeneity can be determined using analytical chemistry techniques such as polyacrylamide gel electrophoresis or high performance liquid chromatography. A protein which is the predominant species present in a preparation is substantially purified.

"Monoclonal antibody" can refer to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567, each of which are incorporated herein by reference in their entireties. The monoclonal antibodies may also be isolated from phage libraries generated using the techniques described in McCafferty et al., 1990, Nature 348:552-554, for example. Monoclonal antibodies, for example fully human antibodies, can also be made using transgenic mice as described in Bruggemann et al., (*Arch Immunol Ther Exp (Warsz)*. 2015; 63(2): 101-108), or using methods as described in EP 2003960 or U.S. Pat. No. 9,220,244, each of which are hereby incorporated by reference in their entireties. Monoclonal antibodies, for example humanized monoclonal antibodies, can also be made using the XenoMouse transgenic animal as described in U.S. Pat. No. 5,939,598, or using the methods as described in U.S. Pat. No. 6,150,584 or 6,075,181, each of which are hereby incorporated by reference in their entireties.

A "variable region" of an antibody can refer to the variable region of the antibody light chain or the variable region of the antibody heavy chain, either alone or in combination. The variable regions of the heavy and light chain each consist of four framework regions (FR) connected by three complementary determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al, 1997, J. Molec. Biol. 273:927-948). As used herein, a CDR may refer to CDRs defined by either approach or by a combination of both approaches.

"Constant region" of an antibody can refer to the constant region of the antibody light chain or the constant region of the antibody heavy chain, either alone or in combination.

Embodiments as described herein comprise an isolated antibody or binding fragment thereof that specifically binds to an antigenic universal peptide with an amino acid sequence that is at least 80% identical in two or more different microorganisms. For example, such antigenic universal peptides comprise the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82.

Further, embodiments as described herein comprise an isolated antibody (for example, a monoclonal antibody (such as a humanized antibody, a fully human antibody, or a chimeric antibody), a polyclonal antibody,) or binding fragment thereof) that specifically binds to at least one synthetic cell wall peptide, for example a bacterial cell wall peptide or a fungal cell wall peptide. Such peptides, including the antigenic universal peptides described herein, can comprise an amino acid sequence that is at least 80% identical in two or more different microorganisms. In embodiments the peptide corresponds to a cell wall protein, such as fructose-bisphosphate aldolase (Fba; GenBank Accession No.

AOW28947; Protein Accession No. XP_722690), methyltetrahydropteroyltriglutamate homocysteine methyltransferase (Met6; GenBank Access No. AOW30921; Protein Accession No. XP_718219), hyphal wall protein-1 (Hwp1; GenBank Access No. ACN63125), enolase (Enol; GenBank Accession No. AAA71939), glyceraldehyde-3-phosphate dehydrogenase (Gap1; GenBank Accession No. AOW29704), and phosphoglycerate kinase (Pgk1; GenBank Accession No. AAA66523), or a combination thereof.

Binding fragments, for example, can comprise an Fv fragment, a Fab fragment, a F(ab') fragment, a F(ab')$_2$ fragment, a disulfide stabilized Fv protein (dsFv) fragment, a scFv fragment, a minibody fragment, or a diabody fragment. These binding fragments can bind to target peptide sequences comprising, for example the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, SEQ ID NO: 28, SEQ ID NO: 81, or SEQ ID NO: 82, or target peptide sequences found in fructose-bisphosphate aldolase (Fb a; GenBank Accession No. AOW28947; Protein Accession No. XP_722690), methyltetrahydropteroyltriglutamate homocysteine methyltransferase (Met6; GenBank Access No. AOW30921; Protein Accession No. XP_718219), hyphal wall protein-1 (Hwp1; GenBank Access No. ACN63125), enolase (Enol; GenBank Accession No. AAA71939), glyceraldehyde-3-phosphate dehydrogenase (Gap1; GenBank Accession No. AOW29704), and phosphoglycerate kinase (Pgk1; GenBank Accession No. AAA66523), corresponding to cell wall proteins of interest.

In embodiments, the antibody or binding fragment binds to its antigen, such as the peptide antigen, with an equilibrium dissociation constant ($K_D$) of less than or equal to about $10^{-4}$ nM, between $10^{-4}$ nM and $10^{-6}$ nM, or greater than $10^{-6}$ nM. The equilibrium dissociation constant can be determined, for example, by surface plasmon resonance (SPR, e.g., BIAcore), ELISA, gel-shift assays, pull-down assays, equilibrium dialysis, analytical ultracentrifugation, spectroscopic assays, and Isothermal Titration calorimetry.

In embodiments, the antibody or binding fragment thereof has an $IC_{50}$ less than or equal to 0.01 µg/ml, between about 0.01 µg/ml and 30 µg/ml, or greater than 30 µg/ml (see US 20020016681 for a discussion of such $IC_{50}$ measurements, which is incorporated herein by reference in its entirety).

In embodiments, the antibody or binding fragment thereof comprises the product produced by the hybridoma clones 2C9G3, 5A9D1, 5A11B1, 6E3D9, 1D4H5, 7A3C4, 10E7E2, 1A11H8, 10B6H8, 5G5G3, or 9F2G5.

In embodiments, the antibody or fragment thereof produced by the clones generated in response to an antigenic universal peptide (e.g. those hybridoma clones listed in Table 3) comprises a variable domain having a variable light chain (VL) amino acid or nucleotide sequence at least 90% identical to those produced by the clones generated in response to an antigenic universal peptide or chimeric peptide, or having a variable heavy chain (VH) amino acid or nucleotide sequence at least 90% identical to those produced by the clones generated in response to an antigenic universal peptide or chimeric peptide. For example, the antibody or fragment thereof comprises a variable domain having a variable light chain (VL) amino acid or nucleotide sequence at least 90%, 91%, 92%, 93%, 94%, 95%, 96%, 97%, 98%, 99%, or 100% identical to those detailed in TABLE 1 or having a variable heavy chain (VH) amino acid or nucleotide sequence at least 90% identical to those detailed in TABLE 1. In embodiments, the variable light chain ($V_L$) and/or variable heavy chain comprises fully human framework region(s).

TABLE 1

| Clone | Isotype | Chain | SEQ ID NO |
| --- | --- | --- | --- |
| 2B10C1 | IgG1 mAb | $V_H$ (DNA) | 59 |
| | | $V_H$ (Amino Acid) | 60 |
| | | $V_L$ (DNA) | 61 |
| | | $V_L$ (Amino Acid) | 62 |
| 1D4H5 | IgG1 mAb | $V_H$ (DNA) | 63 |
| | | $V_H$ (Amino Acid) | 64 |
| | | $V_L$ (DNA) | 65 |
| | | $V_L$ (Amino Acid) | 66 |
| 2D5F7 | IgG2b mAb | $V_H$ (DNA) | 67 |
| | | $V_H$ (Amino Acid) | 68 |
| | | $V_L$ (DNA) | 69 |
| | | $V_L$ (Amino Acid) | 70 |
| 10E7E2 | IgG1 mAb | $V_H$ (DNA) | 71 |
| | | $V_H$ (Amino Acid) | 72 |
| | | $V_L$ (DNA) | 73 |
| | | $V_L$ (Amino Acid) | 74 |
| 9F2G5 | IgG2a mAb | $V_H$ (DNA) | [ ] |
| | | $V_H$ (Amino Acid) | [ ] |
| | | $V_L$ (DNA) | [ ] |
| | | $V_L$ (Amino Acid) | [ ] |

Embodiments as described herein further comprise an engineered cell, such as hybridomas, that secretes an antibody or binding fragment as described herein.

Embodiments as described herein further comprise an isolated nucleic acid encoding an antibody or binding fragment as described herein. The isolated nucleic acid, for example, can be a component of an expression vector. The isolated nucleic acid and/or the expression vector can be transformed into a host cell using methods well established in the art so as to produce the antibody or binding fragment as described herein (Sambrook et al., Molecular Cloning: A Laboratory Manual, Cold SpringHarbor Laboratory, Cold Spring Harbor, 1989). Non-limiting examples of such host cells comprise mammalian cells, such as CHO and HEK 293 cells.

Compositions comprising antibodies or binding-fragments as described herein can further comprise therapeutic and/or prophylactic agents, such as one or more antimicrobial agents. For example, the antimicrobial agent can comprise an anti-fungal agent, an anti-viral agent, an anti-bacterial agent, or an anti-protozoal agent.

Non-limiting examples of an antifungal agent can comprise at least one polyene, at least one azole, at least one allylamine, echinocardins or a combination thereof.

Non-limiting examples of anti-viral agents comprise TFT, Acyclovir, gancyclovir, penciclovir, cidofovir; ribavirin, interferon, phosphonoacetate, Foscarnet, amantadine, Rimatidine, oseltamivir, Valacyclovir, Valgancyclovir, Peramivir, Zanamivir, anti-retroviral drugs or a combination thereof.

Non-limiting examples of anti-bacterial agents comprise aminoglycosides, fluoroquinolones, beta-lactams, macrolide, and tetracyclines.

Non-limiting examples of anti-protozoal agents comprise chloroquine, pyrimethamine, mefloquine, hydroxychloroquine, metronidazole, atovaquone, or a combination thereof.

Active Immunization

The term "active immunization" can refer to the induction of an immune response in an individual, typically an animal, elicited by the administration of an immunogen, vaccine, antigen or hapten-carrier conjugate. By contrast, passive immunization refers to the conferral of immunity in an individual by the transfer of immune molecules or cells into said individual.

Embodiments as described herein comprise antigenic universal peptide vaccines and antigenic vaccine compositions for active immunization against an infection. For example, peptides, chimeric peptides, and compositions comprising the same as described herein can be administered to a subject as a method of active immunization so as to protect against and/or treat an infection, such as a microbial infection. Non-limiting examples of such infections are described herein, and comprise fungal infections, bacterial infections, viral infections, and protozoal infections.

The pharmaceutical compositions of the present invention are advantageously administered in the form of injectable compositions. A typical composition for such purpose comprises a pharmaceutically acceptable carrier. The carrier can be a solid, liquid, solution, suspension, gel, ointment, lotion, or combinations thereof as further discussed herein. For instance, the composition may contain human serum albumin in a phosphate buffer containing NaCl. Other pharmaceutically acceptable carriers include aqueous solutions, non-toxic excipients, including salts, preservatives, buffers and the like (REMINGTON'S PHARMACEUTICAL SCIENCES, 15th Ed., Easton ed., Mack Publishing Co., pp 1405-1412 and 1461-1487 (1975) and THE NATIONAL FORMULARY XIV, 14th Ed., American Pharmaceutical Association, Washington, D.C. (1975), both hereby incorporated by reference). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. The pH and exact concentration of the various components the pharmaceutical composition are adjusted according to routine skills in the art Goodman and Gilman, THE PHARMACOLOGICAL BASIS FOR THERAPEUTICS (7th ed.).

Typically, such vaccines are prepared as injectables, either as liquid solutions or suspensions; solid forms suitable for solution in, or suspension in, liquid prior to injection may also be prepared. The preparation also may be emulsified. The active immunogenic ingredient is often mixed with an excipient that is pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, uttering agents, adjuvants or immunopotentiators that enhance the effectiveness of the vaccine.

The vaccines are conventionally administered intraperitoneally, intramuscularly, intradermally, subcutaneously, orally, nasally, parenterally or administered directly to the urogenital tract, preferably topically, to stimulate mucosal immunity. Additional formulations are suitable for other modes of administration and include oral formulations. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%-95% of active ingredient, preferably 25-70%.

The dose to be administered depends on a predetermined quantity of active material calculated to produce the desired therapeutic effect in association with the required diluent, i.e., carrier or vehicle, and a particular treatment regimen. The quantity to be administered, both according to number of treatments and amount, depends on the subject to be treated, capacity of the subjects immune system to synthesize antibodies, and degree of protection desired. The precise amounts of active ingredient required to be administered depend on the judgment of the practitioner and are peculiar to each individual. However, suitable dosage ranges are on the order of one to several hundred micrograms of active ingredient per individual subject. Suitable regimes for initial administration and booster shots also vary but are typified by an initial administration followed in one or two week intervals by one or more subsequent injections or other administration. Annual boosters may be used for continued protection.

Passive Immunization

"Passive immunization" can refer to conferral of immunity by the administration, by any route, of exogenously produced immune molecules (e.g. antibodies) or cells (e.g. T-cells) into an animal. Passive immunization differs from "active" immunization, where immunity is obtained by introduction of an immunogen, vaccine, antigen or hapten-carrier conjugate into an individual to elicit an immune response.

Passive immunity can occur naturally, when maternal antibodies are transferred to the fetus through the placenta, and it can also be induced artificially, when high levels of antibodies specific to a pathogen or toxin are transferred to non-immune persons through compositions and/or blood products that contain antibodies, such as in immunoglobulin therapy or antiserum therapy.

Passive immunization is used when there is a high risk of infection and insufficient time for the body to develop its own immune response, or to reduce the symptoms of ongoing or immunosuppressive diseases. Passive immunization can be provided when people cannot synthesize antibodies, and when they have been exposed to a disease that they do not have immunity against.

Artificially acquired passive immunity is a short-term immunization achieved by the transfer of antibodies, which can be administered in several forms; as human or animal blood plasma or serum, as pooled human immunoglobulin for intravenous (IVIG) or intramuscular (IG) use, as high-titer human IVIG or IG from immunized donors or from donors recovering from the disease, and as monoclonal antibodies (MAb). Passive transfer is used to prevent disease or used prophylactically in the case of immunodeficiency diseases, such as hypogammaglobulinemia. It is also used in the treatment of several types of acute infection, and to treat poisoning.

Immunity derived from passive immunization lasts for a few weeks to three to four months. Passive immunity provides immediate protection, but the body does not develop memory, therefore the patient is at risk of being infected by the same pathogen later unless they acquire active immunity or vaccination.

Embodiments as described herein comprise antibodies and compositions for passive protection against an infection. For example, antibodies and fragments thereof as described herein can be administered to a subject as a method of passive immunization so as to protect against and/or treat an infection, such as a microbial infection. Non-limiting examples of such infections are described herein, and comprise fungal infections, bacterial infections, viral infections, and protozoal infections.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Introduction

Morbidity and mortality from invasive fungal infections remain unacceptably high despite availability of antifungal agents, underscoring the need for more effective strategies to prevent and/or treat fungal infections.

Invasive fungal diseases often take hold when a subject's natural defenses are weakened, such as what is commonly seen in in hospital settings. Vaccination of high-risk groups, for example subjects admitted to or employed in hospital settings, is a particularly promising strategy to prevent and/or protect against invasive fungal infections because easily identifiable risk factors are clearly defined for many such infections, including candidiasis and aspergillosis. The predominant risk factors for disseminated candidiasis are common iatrogenic and/or nosocomial conditions that disrupt protective anatomical barriers or result in a substantial increase in the colonization burden of *Candida* spp., such as indwelling plastic catheters, abdominal or cardiac surgery, prolonged hospital stay, stay in an intensive care unit, and receipt of broad-spectrum antibiotics. Often, development of such risk factors precedes infection, affording a wide window of opportunity to vaccinate at-risk subjects, such as those at acute risk, before the onset of infection.

Hematogenously disseminated candidiasis in humans is the third leading cause of nosocomial bloodstream infection in the US. *Aspergillus* is the second most common cause of nosocomial, invasive fungal infections, with an incidence of approximately 5 per 100,000 population in the United States. Embodiments as described herein can be used to prevent and/or protect against aspergillosis infection, which has an extremely high mortality rate despite the availability of antifungal therapies. For invasive candidiasis, the mortality rate is 40% to 50%, even with appropriate anti-fungal drug treatments. For invasive aspergillosis, mortality rates range from 40% to 90% in high-risk populations, and are dependent on factors such as host immune status, the site of infection, and the treatment regimen applied Novel universal peptide/multiple-peptide vaccine candidates as described herein are expressed with 100% homology in medically important fungi, such as *Candida* spp. and *Aspergillus* spp. Non-limiting examples of each comprise *C. albican, C. glabrata, C. tropicalis, C. parapsilosis, C. krusei, C. dubliniensis, C. auris, C. parapsilosis, A. fumigatus, A. flavus, A. niger, A. terreus,* and *A. lentulus.*

The synthetic peptide and multi-peptide vaccines against *Candida* spp. protect mice against disseminated candidiasis. Further, antibodies specific for the universal peptides [for example, GPV-MO1 (SEQ ID NO: 81; PTTTIGSFPQ); GPV-M02 (SEQ ID NO. 79; NPDCGLKTR); GPV-M1 (SEQ ID NO. 1; FWVNPDCGLKTR), GPV-M2 (SEQ ID NO. 2; TTTIGSFPQTKDIR)] are each capable of protecting the animals. Without wishing to be bound by theory, we will isolate universal peptide-related monoclonal antibodies that can offer immediate protection by administration of MAbs (i.e., passive protection, or passive immunization). Such compositions and methods provide strong alternative measures to conventional antifungal drug therapy.

With the aging global and US populations, increasingly intensive medical treatments of critical illnesses, for example increasingly aggressive immune-suppressive treatment of patients with cancer, the incidence of invasive fungal infections is expected to continue to rise over the coming decades. Mortality rates associated with these fungal infections remain high despite the availability of new antifungal agents. These factors underscore the important of the development of vaccine compositions and methods to prevent and/or protect against fungal infections.

Peptide Vaccines Against Fungal Species

Synthetic universal peptide and double-peptide vaccines, such as fully synthetic peptide and double-peptide vaccines, against *Candida* spp cell surface epitopes have been successfully designed and tested to protect mice against disseminated candidiasis. In detail, a panel of peptides that are universally produced by medically important *Candida* species in addition to *C. albicans,* as well as *Aspergillus* spp. have been defined. Universal peptide/multiple-peptide vaccines described herein are expressed with 100% amino acid sequence homology in medically important fungi, including medically important *Candida* spp, *Aspergillus fumigates, Aspergillus niger* and other *Aspergillus* spp.

A panel of fully synthetic universal peptide vaccines (for example, GPV-MO1, GPV-MO2, GPV-M1, GPV-M2, GPV-P11, GPV-P2) and a double-peptide vaccine (for example, SEQ ID NO: 83-93) have been developed, each of which was able to protect mice against disseminated candidiasis with the survival rate of 80-100% up to 120 days post challenge.

Subsequent data demonstrates antibodies specific for universal peptides (such as, GPV-MO1, GPV-M1, GPV-M2) are each capable of protecting the animals. Universal peptide-related monoclonal antibodies will be isolated that can be used for immediate protection by passive administration of MAbs, which represents strong alternative measures to conventional antifungal drug therapy.

Without wishing to be bound by theory, embodiments as described herein broadens the range of the protection beyond that of just *Candida albicans* to include protection against fungal species of medical significance, including but not limited to additional *Candida* spp. as well as *Aspergills* spp.

Embodiments as described herein comprise universal synthetic peptide vaccine and double-epitope universal peptide vaccine protective against invasive fungal infection. Without wishing to be bound by theory, the double-peptide vaccine formulation offers protective duality against all medically important *Candida* spp., with the advantages of being cheaper, easier to synthesize, and a more practical application as compared to the original glycopeptide formula (Xin, Hong, et al. "Self-adjuvanting glycopeptide conjugate vaccine against disseminated candidiasis." *PLoS One* 7.4 (2012): e35106, which is incorporated by reference herein in its entirety).

Embodiments as described herein can further comprise coupling, such as covalently linking, the peptide or multi-peptide vaccines to a protein carrier, non-limiting examples of which comprise tetanus toxoid (TT), bovine serum albumin (BSA), ovalbumin, or keyhole limpet hemocyanin (KLH). In some instances, peptide antigens can be too small (for example, less than 7 amino acids in certain instances) to generate significant immune responses on their own. A longer peptide, such as those longer than 20 amino acids, increases the peptide's immunogenicity, but also increases the peptide's chances of cross-reactivity. On the other hand, a shorter peptide, such as those 10 amino acids or less, may improve the specificity, but may not be immunogenic. To solve this problem, these small peptides can be conjugated to larger carrier proteins, such as bovine serum albumin (BSA), ovalbumin, or keyhole limpet hemocyanin (KLH). One of the advantages of KLH is that it does not interfere with ELISA or western blotting because it is not used as a blocking reagent. One common means of conjugation method is the maleimide method, which couples the cysteine residue of the peptide to the carrier protein. For example, see US20140271650, which is incorporated by reference herein in its entirety). To perform this conjugation, one cysteine residue is added to the N- or C-terminus of the peptide so that it may be linked to the carrier protein.

Such embodiments can be an acceptable vaccine formulation for use in a subject, such as a human.

Collectively, embodiments as described herein comprising universal peptide vaccines, such as those comprising double or multiple universal peptide epitopes, can provide broader immune recognitions and subsequent induction of antibody-mediated protection against disseminated fungal infections, such as disseminated candidiasis, and other fungal infections, such as aspergillosis infection.

Compared with Existing *Candida* Vaccine

Several vaccines targeting *Candida* have been described in preclinical settings (De Bernardis, F. et al. A virosomal vaccine against candidal vaginitis: immunogenicity, efficacy and safety profile in animal models. Vaccine 30, 4490-4498 (2012) and Schmidt, C. S. et al. NDV-3, a recombinant alum-adjuvanted vaccine for *Candida* and *Staphylococcus aureus* is safe and immunogenic in healthy adults. Vaccine 30, 7594-7600 (2012), each of which are incorporated by reference herein in their entireties). For example, a protein conjugate vaccine consisting of laminaran (algal glucan) linked to diphtheria toxoid as a carrier protein resulted in significant protection against disseminated candidiasis. However, although carbohydrate antigens are important immune targets associated with a variety of pathogens, most carbohydrates are intrinsically T cell-independent antigens which diminishes their efficacy as immunogens. Further limiting the use of carbohydrate-based vaccines is the complexity of oligosaccharide synthesis. Embodiments as described herein overcome this limitation as the peptide-based vaccines greatly simplify the development of new anti-fungal vaccines, with improved safety, purity, and standardization (Peptide-Based Immunotherapeutics and Vaccines, Journal of Immunology Research Volume 2014 (2014), Article ID 256784, 2 pages; and Skwarczynski, Mariusz, and Istvan Toth. "Peptide-based synthetic vaccines." Chemical Science 7.2 (2016): 842-854, each of which are incorporated herein by reference in their entireties).

Another example of a *Candida* vaccine previously described is based on the agglutinin-like sequence (Als) family of proteins from *Candida albicans*. Specifically, the recombinant N-termini of the *C. albicans* surface adhesins Als1p or Als3p (rAls1p-N or rAls3p-N) protected mice from otherwise lethal disseminated candidiasis, and also reduced fungal burden in a vaginitis model and a steroid-treated oropharyngeal candidiasis model. However, the Als-vaccine only protected disseminated candidiasis caused by a single *Candida* species, *Candida albicans*, and offered no protection against other medically important candidiasis and *aspergillus* species (Schmidt, Clint S., et al. "NDV-3, a recombinant alum-adjuvanted vaccine for *Candida* and *Staphylococcus aureus*, is safe and immunogenic in healthy adults." Vaccine 30.52 (2012): 7594-7600). Unlike the Als-vaccine, embodiments as described herein can protect against disseminated candidiasis caused by diverse medically important fungal species, non-limiting examples of which include *Candida* spp such as *C. albican, C. glabrata, C. tropicalis, C. parapsilosis, C. krusei, Candida dubliniensis, Candida auris*, and *C. parapsilosis*, and *Aspergillus* spp such as *A. fumigatus, A. flavus, A. niger*, and *A. terreus, A. lentulus*.

Compared with Existing *Aspergillus* Vaccines

The feasibility of vaccination of mice with crude antigen preparations from an *Aspergillus* strain, *A. fumigatus*, has been demonstrated (Cenci E, Mencacci A, Bacci A, Bistoni F, Kurup V P, Romani L. T cell vaccination in mice with invasive pulmonary aspergillosis. J Immunol. 2000; 165: 381-8; Ito J I, Lyons J M. Vaccination of corticosteroid immunosuppressed mice against invasive pulmonary aspergillosis. J Infect Dis. 2002; 186:869-71. doi: 10.1086/342509). However, a crude protein preparation is not going to support a clinical development program as a defined antigen preparation that can be manufactured to GMP-compliance must be identified. Thus, a defined antigen preparation must be identified. Embodiments as described herein, such as the peptide-based vaccines, can be manufactured to GMP-compliance ideal for clinical development and clinical use.

Subcutaneous vaccination of mice with recombinant Asp f 3, or specific fractions thereof, protected mice from subsequent lethal inhalational challenge with *A. fumigatus* (Ito J I, Lyons J M, Hong T B, Tamae D, Liu Y K, Wilczynski S P, Kalkum M. Vaccinations with recombinant variants of *Aspergillus fumigatus* allergen Asp f 3 protect mice against invasive aspergillosis. Infect Immun. 2006; 74:5075-84). While protection with the soluble form of protein required the use of TiterMax adjuvant (which is too toxic for use in humans), a protein precipitate form of the vaccine administered as a suspension in methylcellulose carrier was also protective and thus potentially clinically relevant. However, compared to the vaccine components of protein mixtures as described in Ito et al., embodiments as described herein, such as the peptide or double-peptide vaccines, are much safer and cheaper to manufacture; with guaranteed purity and consistency in synthesis. Ito et al. discussed the use of crude protein mixtures, which would not be suitable for use in humans due to safety concerns related to toxicity and allergenicity. Without wishing to be bound by theory, embodiments as described herein, including peptide vaccines and peptide vaccines with modifications (such as linking to carrier proteins, mixtures with FDA approved adjuvants, for example), are suitable for human use, such as a vaccine against invasive pulmonary aspergillosis.

Advantages of Double/Multiple Universal Peptide Vaccines

Univalent vaccines comprise a single recombinant protein antigen. Although such *C. albicans* vaccines can generate immune memory responses that lead to the production of virulence-neutralizing, protective antibodies, they are unsuitable to achieve high-grade, persistent protection in humans due primarily to their univalence.

A defining characteristic of *C. albicans* is its extraordinary range of virulence factors that facilitate tissue invasion by enabling the fungus to escape from host immunity. Taking advantage of this defining characteristic, embodiments as described herein comprise multivalent vaccines that targets two or more concurrent but unrelated virulence factors which, without wishing to be bound by theory, will have a better chance of providing protection against candidiasis. Combination of antigens that are related to key *C. albicans* virulence attributes or biological functions can induce additive or synergistic immune responses, broadening the spectrum of protective antibodies and reducing the probability of fungal immune evasion. As an example of such a multivalent vaccine, the double-peptide vaccine GPV-M1-KK-GPV-P2 comprises the GPV-P2 peptide from Pgk1 protein and the GPV-M1 peptide from Met6 protein, both of which are cell wall proteins of *Candida* spp.

Continued Development

A detailed mechanistic understanding of universal peptide vaccines protection is contemplated, which will elucidate the fundamental requirements of host defense against disseminated candidiasis.

The protective efficacy of embodiments as described herein, such as universal peptides and double peptides, in combination with tetanus toxoid carrier protein (TT) is contemplated, as TT has been widely used in US Food and Drug Administration (FDA)-approved vaccines.

A dosing schedule, route of administration, and use of an adjuvant are contemplated, as such information can support an "Investigational New Drug" (IND) application to support the commencement of clinical testing.

Example 2

Abstract

Fully synthetic universal peptide vaccines (Table 1) and double-peptide vaccines (Table C) against *Candida* spp cell surface epitopes have been designed and subsequently tested for their ability to protect mice against disseminated candidiasis. For example, a panel of peptides have been identified that are universally produced by all medically important *Candida* species including but not limited to *C. albicans*, as well as by some *Aspergillus* species. Such universal peptide/double-peptide vaccines as described herein are expressed at high homology (81-100%) in many medically important fungi, including but not limited to medically important *Candida* spp (Table 2), *Aspergillus fumigates*, *Aspergillus niger* and other *Apergillus* spp. For example, Table 1 lists fully synthetic universal peptide vaccines, each of which can protect mice against disseminated candidiasis as demonstrated by survival rate of 80-100% up to 120 days post challenge.

Further, monoclonal antibodies (mAbs), such as IgG monoclonal antibodies, specific for these universal peptides were isolated and purified (Table 3), and tested for protective efficacy by passive transfer in mouse model of human disseminated candidiasis. Each mAb can protect naïve mice against invasive candidiasis by passive transfer of the mAb before lethal challenge. The synergy of protective efficacy with two mAbs combination have also been tested (See Table 8).

Collectively, *C. albicans* cell surface peptide-related and *Candida* universal peptide-related monoclonal antibodies (mAbs) that can be used for immediate protection by passive administration of those mAbs to naïve animals have been isolated, which represents attractive alternatives to conventional antifungal drug therapy. Without wishing to be bound by theory, mAbs specific for the universal peptide vaccines are protective in mouse model of disseminated candidiasis caused by non-*albicans Candida* species, non-limiting examples of which comprise *C. glabrata*, *C. parapsilosis*, *C. tropicalis*, *C. dubliniensis*, *C. krusei*, and *C. auris*.

Embodiments as described herein further comprise double chimeric peptide vaccine constructs, such as those that are further modified to be suitable for human use by simple i.p. immunization approach. Without wishing to be bound by theory, such embodiments can induced high levels of protection without the need for an adjuvant and carrier protein, as demonstrated by simple i.p. immunization of mice with the peptide. Humans have a much more robust immune system as compared to mice, so we expect the newly designed double-peptide constructs, with appropriate spacer amino acids and T cell universal epitopes, can induce protective immunity under adjuvant-free conditions, via a simple i.p. injection, which leading to a new peptide vaccine formula with immunization approaches perfectly feasible for human use.

Introduction

Morbidity and mortality from invasive fungal infections remain unacceptably high despite availability of new antifungal agents, underscoring the need for more effective preventative strategies. Invasive fungal diseases often takes hold when a subject's natural defenses are weakened. These infections frequently occur in hospital settings. Vaccination of high-risk groups is a particularly promising strategy to prevent invasive fungal infections because easily identifiable risk factors are clearly defined for many such infections, non-limiting examples of which comprise candidiasis and aspergillosis. Often, development of such risk factors precedes infection, affording a wide window of opportunity to vaccinate acutely at-risk patients before the onset of infection.

Being a main invasive fungal disease, hematogenously disseminated candidiasis in humans is the leading cause of nosocomial bloodstream infection in the US. *Aspergillus* is the second most common cause of nosocomial, invasive fungal infections, with an incidence of approximately 5 per 100,000 population in the United States. Embodiments as described herein can protect and/or prevent infections caused by *Candida* spp. and *Aspergillus* spp., the latter of which has an extremely high mortality rate as compared to the former despite antifungal therapy (45% to >80%).

The most common causes of invasive fungal infections are members of the genus *Candida* (1). Disseminated candidiasis is the cause of more fatalities than any other systemic mycosis (2,3). The medically significant *Candida* species that cause more than 90% of invasive infections in humans include: *C. albicans*, the most common species identified (~60%); *C. glabrata* (15-20%), *C. parapsilosis* (10-20%), *C. tropicalis* (6~12%); and *C. krusei* (<5%) (4). Vaccination of high-risk groups is a strategy to prevent invasive *Candida* infection (5). Reports highlight the development of peptide and glycopeptide vaccines and chimeric double-peptide vaccine against *C. albicans* cell surface epitopes that can induce protection in mice against disseminated candidiasis (6-9). Importantly, the reported peptides only offer protection against *C. albicans*, and are unlike embodiments as described herein which offer protection against infections caused by both *Candida* spp. and other fungal species such as *Aspergillus* sp. It was also demonstrated that mAbs specific for the peptides protect both immunocompetent and neutropenic mice against Candidiasis (7,9,10).

Subsequently, double-peptide vaccines designed for human use induced high levels of protection without the need for an adjuvant and carrier protein via the simple i.p. immunization of mice with the peptide (Xin, H. "Double chimeric peptide vaccine and monoclonal antibodies that protect against disseminated candidiasis." *J Vaccines Vaccin* 5 (2014)).

To provide for broader coverage against all medically important non-*albicans Candida* (NAC) species in addition to *C. albicans*, universal peptide vaccines as described herein were designed and mAbs were isolated, both of which were tested for the protective efficacy against disseminated candidiasis in mice.

Without wishing to be bound by theory, the double-peptide vaccine formulation demonstrates protective duality against all medically important *Candida* spp. while providing for a relatively lost cost to manufacture and easier synthesis. Our work demonstrates that development of a double chimeric peptide vaccine that induces protective immune responses against two unrelated cell surface peptide epitopes of *C. albicans* is a better approach against the disease, for example than those that induce a protective immune response against a single epitope. For example, the double vaccine can protect against the mutant strain that may lose one of the epitopes. In addition, combinations of multiple MAbs can provide the most effective form of passive transfer protection, which can demonstrate emergent properties with regard to protective efficacy.

The term "emergent properties" can refer to a property that cannot be explained by the individual components alone, and usually reflects an outcome that is greater than the sum of the parts with a certain form of novelty. As described herein, for example, combinations of mAbs, as opposed to each individual antibody alone, can synergistically benefit the host, such as providing greater protection against fungal infections than the sum of each mAb alone, requiring much less dose of mAb for protective effects, offer complete protection (i.e., 100% survival), and result in fungal cells being completely cleared from organs.

As described herein, the universal peptide vaccines, which comprise for example double or multiple universal peptide epitopes, provide for universal immune recognitions and induction of antibody-mediated protection against disseminated candidiasis against aspergillosis infection.

Of concern when developing potential *Candida* vaccines is the notion that candidiasis occurs almost exclusively in immune-compromised patients whose immune system may not be equipped to respond immunologically to a vaccine. However, there is extensive literature confirming the immunogenicity and efficacy of vaccines even in patients with weakened immune systems—for example, those with neutropenia, active leukemia, HIV infections, or those receiving immunosuppressive corticosteroids (dos Santos, Sigrid De Sousa, et al. "*Haemophilus influenzae* type b immunization in adults infected with the human immunodeficiency virus." *AIDS research and human retroviruses* 20.5 (2004): 493-496.; Dockrell, David H., et al. "Immunogenicity of three *Haemophilus influenzae* type b protein conjugate vaccines in HIV seropositive adults and analysis of predictors of vaccine response." *Vaccine* 17.22 (1999): 2779-2785.; Levin, Myron J., et al. "Immunization of HIV-infected children with varicella vaccine." *The Journal of pediatrics* 139.2 (2001): 305-310.; Tedaldi, Ellen M., et al. "Hepatitis A and B vaccination practices for ambulatory patients infected with HIV." *Clinical Infectious Diseases* 38.10 (2004): 1478-1484.; Sinisalo, Marjatta, et al. "*Haemophilus influenzae* type b (Hib) antibody concentrations and vaccination responses in patients with chronic lymphocytic leukaemia: predicting factors for response." *Leukemia & lymphoma* 43.10 (2002): 1967-1969. Nordøy, Tone, et al. "Cancer patients undergoing chemotherapy show adequate serological response to vaccinations against influenza virus and *Streptococcus pneumoniae.*" *Medical Oncology* 19.2 (2002): 71-78.; Leung, Ting-Fan, et al. "Immunogenicity of a two-dose regime of varicella vaccine in children with cancers." *European journal of haematology* 72.5 (2004): 353-357.; Klugman, Keith P., et al. "A trial of a 9-valent pneumococcal conjugate vaccine in children with and those without HIV infection." *New England Journal of Medicine* 349.14 (2003): 1341-1348.; Madhi, Shabir A., et al. "The impact of a 9-valent pneumococcal conjugate vaccine on the public health burden of pneumonia in HIV-infected and -uninfected children." *Clinical infectious diseases* 40.10 (2005): 1511-1518.). At the same time, the development of effective mAbs is extremely important because they can protect against severe infection more rapidly than antifungal drugs, and they are also effective against antifungal resistance in multiple *Candida* species. As described herein. peptide-vaccine-specific monoclonal antibodies (mAb s) for the passive immunization in host against *Candida* infection (Table 3 and Table 4) have been isolated and purified. Further, the combination of two protective mAbs into one cocktail provides for a more effective protection as compared to single mAb treatment (Table 6 and Table 7).

Embodiments in this Example

Embodiments as described herein comprise antigenic universal peptides, such as universal peptides, that are expressed by clinically related *Candida* species in addition to *C. albicans*. Without wishing to be bound by theory, such peptides can protect against all medically significant *Candida* spp.

Embodiments as described herein also comprise multivalent peptide vaccines that are superior to the existing one-antigen (univalent) vaccine. According to Cassone's 2013 nature review (Cassone, Antonio. "Development of vaccines for *Candida albicans*: fighting a skilled transformer." *Nature Reviews Microbiology* 11.12 (2013): 884-891.), it is unlikely that a univalent vaccine will be successful as the complexity of *C. albicans* antigens and host-invasion mechanisms makes it difficult to obtain effective immune protection with a single antigen. Our multivalent vaccine that targets two or more unrelated virulence factors will have a better chance of providing protection and avoiding immune evasion. Without wishing to be bound by theory, multivalent vaccines as described herein which targets two or more unrelated protective epitopes offer improved protection when compared to univalent peptide vaccines and can avoid immune evasion.

Embodiments as described herein further comprise mAbs and protective combinations thereof which can protect against severe infection more rapidly than antifungal drugs, and are also effective against antifungal resistance in multiple *Candida* species.

Embodiments as described herein further comprise double peptide vaccine, further including such vaccines that do not require an adjuvant and carrier protein in order to be effective. Peptide-based vaccines are promising approaches to treat infections, however their sometimes-weak immunogenic potency impedes their clinical application. Addressing this unmet need are embodiments as described herein comprising double-peptide construct. Such embodiments can comprise spacer amino acids and/or T cell universal epitopes, and can induce protective immunity under adjuvant-free conditions, leading to a peptide vaccine, compositions comprising the same, and methods of using the same for immunizations of mammals, such as humans.

Materials and Methods

*Candida* strains and culture conditions. *C. albicans* 3153A and SC5314, *C. parapsilosis* (ATCC MYA-4646), *C. tropicalis* (ATCC 28775), *C. krusei* (ATCC 6258), *C. glabrata* (ATCC 2001) and *S. cerevisiae* (ATCC 9463) were grown as stationary-phase yeast cells in glucose-yeast extract-peptone broth at 37° C., washed and suspended to the appropriate cell concentration (5×106/ml) in Dulbecco's PBS (DPBS; Sigma), and used to infect mice intravenously (i.v.) as described before (14,15). *C. albicans* strain 3153A was also used for serum antibody absorption, immunofluorescence staining and flow cytometric analysis.

Mice. BALB/c and C57BL/6 female mice (National Cancer Institute Animal Production Program, Frederick Md.) 5 to 7 weeks old were used throughout. Mice were always maintained in our AAALAC-certified animal facility and all animal experiments were done in accordance with a protocol approved by the Institutional Animal Care and Use committee (IACUC) at LSU Health Sciences Center (LSUHSC).

Peptide vaccines. Two 14-mer peptides Fba and Met6 are derived from N-terminus of *C. albicans* cell wall proteins fructose-bisphosphate aldolase (Fba) and methyltetrahydropteroyltriglutamate (Met6). Fba peptide (YGKDVKDLFDYAQE) and Met6 peptide (PRIGGQRELKKITE) were produced commercially (GenScript). All the universal peptides, derived from N-terminus of *Candida* cell wall proteins, were listed at Table 1 with sequence detail. They were produced commercially (Gen Script).

Protective mAbs. Hybridoma clones, which produce mAbs specific for Fba peptide, Met6 peptide, Hwp1 peptides and the universal peptides (Table 3 and Table 4) were generated from mice vaccinated with peptide-pulsed dendritic cell (DC) preparation as described previously (6). Briefly, BALB/c mice were immunized by injection of synthetic peptide pulsed DCs to stimulate the production of antibodies against peptide as described above. Ten days after the second booster, serum was taken from each animal to determine animals with the highest anti-peptide titers for subsequent sacrificing, removal of spleens and preparation of single cell suspensions. Hybridoma clones were established by the polyethylene glycol facilitation of fusion of spleen cells to an SP2/0-AG14 myeloma cell line by standard protocols. Hybridoma clones were screened by ELISA for production of specific anti-peptide antibody; only the highest titers and most rapidly growing clones were selected for subsequent cloning×3 or more by limiting dilution.

The hybridoma cell lines were initially grown in antibiotic-free RPMI 1640 medium (Sigma) supplemented with 10% fetal bovine serum (Invitrogen) and 2 mM L-glutamine (Sigma) at 37° C. and in the presence of 5% CO2. For antibody production, the hybridoma clones were grown in antibiotic-free, BD cell mAb serum-free medium (but containing 1.1 mg bovine serum albumin/ml) in a CELLine device (BD, Bedford, Mass.). All the peptide-specific mAbs (IgGs) were purified and analyzed as described before (9). In short, the supernatant was collected and mAb was purified by affinity chromatography using a Protein A Sepharose 4FF column (GE Healthcare, USA). The isotype of mAb was determined with a Mouse Monoclonal Antibody Isotyping Kit (Pierce, USA).

Isolation and culture of dendritic cells (DCs) from mouse bone marrow. Dendritic cells (DCs) were generated from mouse bone marrow by a previously described method (6,16). Briefly, donor mice were euthanized by CO2 asphyxiation, their long bones and tibias were aseptically removed, bone marrow was flushed from the bones by forcibly injecting several ml of RPMI-1640 and clumps were removed or dispersed by gentle pipetting through a sterile 70-mm cell strainer. Red blood cells were lysed (ACK lysing buffer, 0.15 M NH4C1, 1.0 mM KHCO3, 0.1 mM EDTA) for 4 min and the remaining bone marrow cells were suspended in complete medium [CM, RPMI-1640 supplemented with 10% FBS (FBS), 2 mM L-glutamine, 1% of nonessential amino acids and 100 units/ml penicillin and 100 µg/ml streptomycin], adjusted to 2×105 cells per ml plated in 6-well plates at 5 ml per well and cultured for up to 9 days in the presence of 40 ng/ml of rmGM-CSF and rmIL-4 (R&D Systems) at 37° C., 5% CO2. On days 4 and 7 of culture, the same amount of fresh GM-CSF and IL-4 was added to the wells.

Active Immunizations with peptide pulsed dendritic cells. The antigen-pulsed DC immunization approach proved to be a powerful way to identify the protective peptide epitopes on *C. albicans* cell surface (6,10,17). We have demonstrated the feasibility of this approach in our finding of protective peptide-based vaccines (7). It allows us to perform rapid throughput evaluation of candidate short peptides. When protective double universal peptide conjugate(s) become identified by this study, immunization approaches suitable for human use will be applied in further studies. All active vaccinations were conducted as previously described (6,7, 9). DCs were pulsed in vitro with universal peptide as described before with minor modification by totally removing CFA for last booster (6). Briefly, DCs in culture were pulsed with the peptide antigen (1 µM) on day 6. On day 7, PGE2 (10-7M) was added along with LPS (2 µg/ml, Sigma) for 24 h to induce DC maturation. On day 9, antigen-pulsed DCs were washed extensively and 5×105 in 200 µl DPBS were given by intraperitoneal (i.p.) route as the priming dose to mice. The mice were boosted i.p. at day 14 and day 28 with fresh antigen-pulsed DCs without adjuvant.

To test the efficacy of the vaccine in immunocompromised mice, vaccinated mice were induced neutropenia by intraperitoneal injection of 200 mg/kg of cyclophosphamide (CY; Sigma-Aldrich) on day −3 followed by another 4 doses (150 mg/kg) every 10 days on days 10, 20, 30 and 40 relative to infection.

Induction of neutropenia. Although *C. albicans* remains the dominant disease-causing pathogen of this genus, rates of infections caused by non-*albicans Candida* (NAC) species are increasing. Among these *Candida* species, only *C. albicans* is pathogenic in the normal mouse model. To test vaccine and mAbs against non-*albicans Candida* spp, we have developed neutropenic murine models of disseminated infection by *C. glabrata*, *C. tropicalis*, and *C. parapsilosis*. Before challenge, BLAB/c mice were made neutropenic by intraperitoneal receipt of a 200 mg/kg dose of cyclophosphamide (CY; Sigma-Aldrich) at day −3. The i.p. injection (150 mg/kg) is repeated every 10 days after infection (i.e., at days 10, 20, 30, and 40 post-infection) in order to maintain low neutrophil counts for the entire experimental procedure. The experiment was set up to test this regimen, which has been shown to render mice neutropenic (The absolute neutrophil count is <500 cells/mm3) within 3-4 day of the first cyclophosphamide injection, and neutropenia lasts until the termination of the experiments (day 50). To evaluate leukocytopenia in these mice, blood samples were collected from tail veins 3 days after each CY or saline injection (n=10 in each group). Total leukocyte and differential cell counts were determined on a hemocytometer and by Wright-Giemsa staining. Body weights of the mice were also measured and compared for 14 days after the first CY or saline injection (n=10 in each group).

Fungal challenge dose and assessment of protection. Although *C. albicans* remains the dominant disease-causing pathogen of this genus, rates of infections caused by non-*albicans Candida* (NAC) species are increasing (18). Among these *Candida* species, only *C. albicans* is pathogenic in the normal mouse model (19,20). We have developed neutropenic murine models of disseminated infection by *C. glabrata, C. tropicalis*, and *C. parapsilosis*. Preliminary experiments demonstrated the optimal dose of each *Candida* strain for producing an acute infection, with 80-100% of animals dying within 10-15 days. In details, mice of different experimental groups (five mice per group) were intravenously infected with 5×106 viable *C. parapsilosis* ATCC MYA-4646 (A), 1×108 *C. glabrata* ATCC 2001 cells (B) and 1×107 *C. tropicalis* ATCC 28775 cells (C) in 0.1 ml DPBS. As controls, immunocompetent mice were challenged with the same dose of each *Candida* strain tested.

Passive transfer of MAbs by intraperitoneal (i.p.) route. The preventive effect of peptide-specific mAbs listed in Table 3 and Table 4 in naïve mice was examined by passive transfer experiments. Each mAb was appropriately diluted in DPBS to give a 40,000-100,000 ELISA titer against each corresponding specific peptide coated on the plate. For testing, mice received 0.5 ml of each mAb or 1 ml of two mAbs in combination (0.5 ml of each) intraperitoneally. Table 6 and Table 7 have listed all the peptide-specific mAb combinations that have been tested, as well as the protective efficacy of each mAb cocktail as compared to single mAb treatment. The negative control materials tested in mice were single mAb or DPBS. Control mice received 0.5 ml of the DPBS diluents or single mAb treatment. For each condition, 6- to 8-week-old female BALB/c mice (NCI) were given 0.5 ml of test mAb, or 1 ml two mAb cocktails or control materials intraperitoneally, followed 4 h later by 0.1 ml intravenously of defined lethal dose of yeast cells per milliliter of DPBS. Mice were divided into groups with five mice each and three independent experiments were carried out. In some experiments, mice were given the same dose of mAbs or control materials on every other day post-challenge for two weeks, as compared to the protective efficacy of mAb in combinations. All mice were sacrificed on day 50. For animal groups that were challenged non-*albicans candida* species, determined optimal challenge doses were applied for each *candida* strain.

Statistical Analysis. Survival times were statistically evaluated by Kaplan-Meier (GraphPad Prism, version 6), and statistical significance was subsequently calculated for each preset time point of analysis. A P value <0.05 was considered to be statistically significant.

Results:

Table 2 lists universal peptide vaccines that induced protection against disseminated candidiasis caused by *C. albicans* in mice. The universal peptide vaccines listed in Table 1 are expressed at high homology by all analyzed medically important *Candida* species in addition to *C. albicans* (see details at Table 2). By dendritic cell (DC) based immunization approach as described herein, each of the universal peptide vaccines was able to protect mice against disseminated candidiasis caused by *C. albicans*, with the survival rate 80-100% up to 80-120 days post challenge.

TABLE 2

| Universal peptide vaccines | Sequences | SEQ ID NO: |
|---|---|---|
| GPV-M1 | cFWVNPDCGLKTR | 1 |
| GPV-M2 | cTTTIGSFPQTKDIR | 2 |

TABLE 2-continued

| Universal peptide vaccines | Sequences | SEQ ID NO: |
|---|---|---|
| GPV-M3 | ADKDSLDLEPISLLPK | 3 |
| GPV-M4 | YNLPLFPTTTIGSFPQTKDIR | 4 |
| GPV-M5 | DDVSGKIQALQLGLALR | 5 |
| GPV-M6 | GWPEVKESLTNMVEAAK | 6 |
| GPV-M7 | YTKFDLAPIDVLFAMGR | 7 |
| GPV-P1 | cAILGGSKVSDKI | 14 |
| GPV-P3 | cIVIIGGGDTATVAKK | 15 |

Table 3 displays the homology of protective universal peptide vaccines among all medically significant *Candida* species.

TABLE 3

| Candida spp. | GPV-P1 | GPV-P3 | GPV-M1 | GPV-M2 | GPV-M3 | GPV-M4 | GPV-M5 | GPV-M6 | GPV-M7 |
|---|---|---|---|---|---|---|---|---|---|
| albicans | 100% | 100% | 100% | 100% | 100% | 100% | 100% | 100% | 100% |
| glabrata | 100% | 100% | 100% | 100% | 81% | N/A | N/A | N/A | 82% |
| parapsilosis | 100% | 100% | 100% | 100% | 100% | 100% | 88% | 94% | 100% |
| tropicalis | 100% | 100% | 100% | 100% | 100% | 100% | 100% | 94% | 94% |
| dubliniensis | 100% | 100% | 100% | 100% | 100% | 100% | 100% | 100% | 100% |
| krusei | 100% | 100% | 100% | 100% | 100% | 100% | N/A | 0% | N/A |
| auris | N/A | N/A | N/A | 100% | 93% | 100% | 82% | 82% | 100% |

Table 4 displays hybridoma clones producing universal peptide-specific mAbs and the isotype of each protective mAbs. The hybridoma clones that produce the universal peptide specific mAbs listed above were generated from mice vaccinated with peptide-pulsed dendritic cell (DC) preparation as described previously (6). The isotype of mAb was determined with a Mouse Monoclonal Antibody Isotyping Kit (Pierce, USA). All the mAbs listed at Table 4 were able to confer enhanced protection against systemic candidiasis in passive transfer experiments in mouse model of human disseminated candidiasis. In detail, BALB/c mice were given an i.p dose of each mAb four hours before hematogenous challenged with a lethal dose of *C. albicans*3153A cells. Mice that received mAb treatments had prolonged survival as compared to control animals, which received DPBS buffer or adsorbed mAb solutions at the same time with mAb treatment. In addition, surviving animals that received the antibody had significantly reduced or non-detectable fungal burdens in their kidneys as compared to controls. Importantly, passive protection was prevented by removal of the mAbs by absorption with *Candida* cells before transfer, which provided strong additional evidence for the protection being due to the mAb.

In embodiments, the antibody or fragment thereof produced by the clones generated in response to an antigenic universal peptide (e.g, those hybridoma clones listed in Table 4) comprises a variable domain having a variable light chain (VL) amino acid or nucleotide sequence at least 90% identical to those produced by the clones generated in response to an antigenic universal peptide or chimeric peptide, or having a variable heavy chain (VH) amino acid or nucleotide sequence at least 90% identical to those produced by the clones generated in response to an antigenic universal peptide or chimeric peptide. For example, the antibody or fragment thereof comprises a variable domain having a variable light chain (VL) amino acid or nucleotide sequence at least 90%, 91%, 92%, 93%, 94%, 95%, 96%, 97%, 98%, 99%, or 100% identical to those of the clones detailed in TABLE 4 or having a variable heavy chain (VH) amino acid or nucleotide sequence at least 90% identical to those of the clones detailed in TABLE 4. In embodiments, the variable light chain ($V_L$) and/or variable heavy chain comprises fully human framework region(s).

TABLE 4

Hybridoma clone and related protective peptide-specific mAbs

| Hybridomas | mAb | mAb isotype | peptide vaccine | peptide Sequences |
|---|---|---|---|---|
| 2C9G3 | 2C9 | IgG2a | GPV-M2 universal | cTTTIGSFPQTKDIR (SEQ ID NO: 2) |
| 5A9D1 | 5A9 | IgG3 | GPV-M2 universal | cTTTIGSFPQTKDIR (SEQ ID NO: 2) |
| 5A11B1 | 5A1 | IgG3 | GPV-M2 universal | cTTTIGSFPQTKDIR (SEQ ID NO: 2) |
| 6E3D9 | 6E3 | IgG1 | GPV-M1 universal | cFWVNPDCGLKTR (SEQ ID NO: 1) |
| 1D4H5 | 1D5 | IgG1 | GPV-M1 universal | cFWVNPDCGLKTR (SEQ ID NO: 1) |
| 7A3C4 | 7A3 | IgG1 | GPV-M1 universal | cFWVNPDCGLKTR (SEQ ID NO: 1) |
| 10E7E2 | 10E7 | IgG1 | GPV-P3 universal | cIVIIGGGDTATVAKK (SEQ ID NO: 1) |
| 1A11H8 | 1A11 | IgG3 | GPV-P1 universal | cAILGGSKVSDKI (SEQ ID NO: 1) |
| 10B6H8 | 10B6 | IgG1 | GPV-P1 universal | cAILGGSKVSDKI (SEQ ID NO: 1) |

TABLE 4-continued

Hybridoma clone and related protective peptide-specific mAbs

| Hybridomas | mAb | mAb isotype | peptide vaccine | peptide Sequences |
|---|---|---|---|---|
| 5G5G3 | 5G5 | IgG2a | GPV-P1 universal | cAILGGSKVSDKI (SEQ ID NO: 1) |

The underlined represents the peptide antigen (can also be referred to as peptide epitope) that is recognized and bound by the antibody, such as the monoclonal antibody.

Table 5 displays the hybridoma clones producing protective mAbs that are specific for peptides derived from *C. albicans* cell wall proteins and the isotype of each protective mAbs. Three T-cell peptides (Fba peptide, Met6 peptide and Hwp1 peptide) found in *Candida albicans* cell wall proteins were selected by algorithm peptide epitope searches and fully synthetic peptides were used to immunize mice by DC-based immunization approach. The three cell wall proteins were selected because of expression during human candidiasis and cell wall association, and included fructose-bisphosphate aldolase (Fba); methyltetrahydropteroyltriglutamate-homocysteine methyltransferase (Met6); hyphal wall protein-1 (Hwp1). The hybridoma clones listed at Table 5, which produce the peptide specific mAbs, were generated from mice vaccinated with peptide-pulsed dendritic cell (DC) preparation as described previously (6). The isotype of mAb was determined with a Mouse Monoclonal Antibody Isotyping Kit (Pierce, USA). All the mAbs listed at Table 5 conferred enhanced protection against systemic candidiasis in passive transfer experiments in mouse model of human disseminated candidiasis. In detail, BALB/c mice given an i.p dose of each mAb four hours before hematogensous challenge with a lethal dose of *C. albicans* 3153A had prolonged survival as compared to control animals. In addition, surviving animals that received the antibody had reduced/non detectable fungal burden in their kidneys. Importantly, passive protection was prevented by removal of the mAbs by absorption with *Candida* cells before transfer, which provided strong additional evidence for the protection being due to the mAb).

TABLE 5

Hybridoma clone, peptide vaccines, and related protective peptide-specific mAbs

| Hybridomas | mAbs | mAb isotype | Peptide vaccine | Peptide sequences |
|---|---|---|---|---|
| 3H7E3 | 3H7 | IgG1 | Met6 peptide | PRIGGQRELKKITEc (SEQ ID NO: 30) |
| 5E12D10 | 5E12 | IgG1 | Met6 peptide | PRIGGQRELKKITEc (SEQ ID NO: 30) |
| 2B10C1 | 2B10 | IgG1 | Met6 peptide | PRIGGQRELKKITEc (SEQ ID NO: 30) |
| 7H6A2 | 7H6 | IgG2b | Met6 peptide | PRIGGQRELKKITEc (SEQ ID NO: 30) |
| 6H1G8 | 6H1 | IgG2b | Hwp1 peptide | QGETEEALIQKRSYc (SEQ ID NO: 31) |
| 3B5H7 | 3B5 | IgG2b | Hwp1 peptide | QGETEEALIQKRSYc (SEQ ID NO: 31) |
| 5B11H1 | 5B11 | IgG1 | Hwp1 peptide | QGETEEALIQKRSYc (SEQ ID NO: 31) |

TABLE 5-continued

Hybridoma clone, peptide vaccines, and related protective peptide-specific mAbs

| Hybridomas | mAbs | mAb isotype | Peptide vaccine | Peptide sequences |
|---|---|---|---|---|
| 2D5F7 | 2D5 | IgG2b | Fba peptide | YGKDVKDLFDYAQE (SEQ ID NO: 29)c |
| 3E2G2 | 3E2 | IgG2b | Fba peptide | YGKDVKDLFDYAQEc (SEQ ID NO: 29) |
| 6G9E11 | 6G9 | IgG2b | Fba peptide | YGKDVKDLFDYAQEc (SEQ ID NO: 29) |
| 9C11F6 | 9C11 | IgG2b | Fba peptide | YGKDVKDLFDYAQEc (SEQ ID NO: 29) |
| 7H5H6 | 7H5 | IgG2b | Fba peptide | YGKDVKDLFDYAQEc (SEQ ID NO: 29) |

Table 6 displays protective universal-peptide-specific mAbs that have been tested in mouse model of human disseminated candidiasis caused by *C. albicans*, *C. tropicalis* and *C. glabrata*. The preventive effect of each universal peptide-specific mAb was examined by passive transfer experiments. Each mAb was appropriately diluted in DPBS (0.2 μg/μl) to give a 100,000 ELISA titer against each universal peptide coated on the plate. For testing, 5 mice of each tested group received 0.5 ml of each mAb intraperitoneally. The negative control materials tested in mice were mAbs absorbed with *C. albicans* yeast cells (3153A) and DPBS. Control mice received 0.5 ml of the DPBS diluents or adsorbed mAb solution. For each condition, 6- to 8-week-old female BALB/c mice (NCI) were given 0.5 ml of test mAb, or control materials intraperitoneally, followed 4 h later by 0.1 ml intravenously of a suspension containing lethal dose of *Candida* cells per milliliter of DPBS. Mice were divided into groups with five mice each and three independent experiments were carried out. We have developed neutropenic murine models of disseminated infection by *C. glabrata*, *C. tropicalis* and *C. parapsilosis*. To induce neutropenia, naïve mice received a 200 mg/kg dose of cyclophosphamide (CY) by i.p. on day −3. Prolonged neutropenia were maintained for 30-50 days by giving each animal a 150 mg/kg dose of CY by i.p. every 10 days after infection. On day 0, BALB/c mice were given an i.p dose of each mAb four hours before being intravenously infected with 5×10$^5$ viable *C. albicans* (3153A), 5×10$^6$ *C. parapsilosis* ATCC MYA-4646 (A), 1×10$^8$ *C. glabrata* ATCC 2001 cells (B) and 1×10$^7$ *C. tropicalis* ATCC 28775 cells (C) in 0.1 ml DPBS.

TABLE 6 universal peptide-specific mAbs provide protection against Non-*albicans Candida* spp in mouse model of human disseminated candidiasis

| mAb | against C. albicans | against C. tropicalis | against C. glabrata | against C. parapsilosis |
|---|---|---|---|---|
| 2C9 | High (80-100%) | High (60-80%) | High (80-90%) | High (70-80%) |
| 5A9 | High (80-90%) | High (70-90%) | High (80-90%) | High (80-90%) |
| 5A1 | High (60-90%) | High (60-80%) | High (60-90%) | High (60-80%) |
| 6E3 | High (80-100%) | High (80-100%) | High (80-90%) | High (80-100%) |

TABLE 6-continued universal peptide-specific mAbs provide protection against Non-*albicans Candida* spp in mouse model of human disseminated candidiasis

| mAb | against C. albicans | against C. tropicalis | against C. glabrata | against C. parapsilosis |
|---|---|---|---|---|
| 1D5 | High (70-80%) | High (60-80%) | High (70-90%) | High (70-80%) |
| 7A3 | High (70-90%) | High (80-90%) | High (80-90%) | High (80-100%) |
| 10E7 | High (80-100%) | High (60-70%) | High (60-70%) | High (60-80%) |
| 1A11 | High (60-90%) | High (70-80%) | High (80-90%) | High (70-80%) |
| 10B6 | High (80-100%) | High (60-80%) | High (60-70%) | High (60-90%) |
| 5G5 | High (80-100%) | High (80-90%) | High (60-80%) | High (70-80%) |

Table 7 displays combinations of universal peptide-specific mAbs (also referred to as mAb cocktails) conferred enhanced protection against systemic candidiasis in passive transfer experiments as compared to single mAb treatment. Mice receiving single mAb treatment had significantly prolonged survival as compared to control animals that received either DPBS or adsorbed mAbs. However, the protective mAbs combination treatment provided the best protection (80-100% survival). Consistently, the group receiving treatment of multiple protective mAbs in combination had the least CFUs in kidneys among all the groups. To test the number of doses of each mAb needed for the complete protection in naïve mice, each mAb was further evaluated by giving to naïve mice every other day post challenge for two weeks. Interestingly, when mAb was given once, it provided 50-60% protection of recipient animals; however, when each mAb was given every other day for two weeks, it increased protection to 70-80% survival (Xin, H. "Double chimeric peptide vaccine and monoclonal antibodies that protect against disseminated candidiasis." *J Vaccines Vaccin* 5 (2014).). However, the combination of protective mAbs provides the best protection with reduced dose of each mAb administered. Specifically, the combination mAb treatment provided 80-100% survival with one dose of mAbs in combination. In all the transfer experiments, passive protection was prevented by removal of the mAbs through absorption with *C. albicans* cells before transfer, which provided strong additional evidence for the protection being due to the mAbs.

TABLE 7

| protective mAb cocktails | Control #1 | control #2 | Protection of mAb cocktails | Synergy of combinations |
|---|---|---|---|---|
| 2C9 + 1A11 | 2C9 | 1A11 | High (90-100%) | Yes++ |
| 2C9 + 10B6 | 2C9 | 10B6 | High (90-100%) | Yes++ |
| 2C9 + 5G5 | 2C9 | 5G5 | N/A | N/A |
| 2C9 + 10E7 | 2C9 | 10E7 | High (70-80%) | No |
| 5A9 + 10E7 | 5A9 | 10E7 | High (100%) | Yes++ |
| 5A9 + 1A11 | 5A9 | 1A11 | High (100%) | Yes++ |
| 5A9 + 10B6 | 5A9 | 10B6 | High (70-80%) | No |
| 5A9 + 5G5 | 5A9 | 5G5 | N/A | N/A |
| 6E3 + 10E7 | 6E3 | 10E7 | High (80-90%) | Yes |
| 6E3 + 10B6 | 6E3 | 10B6 | High (70-80%) | No |
| 6E3 + 1A11 | 6E3 | 1A11 | High (100%) | Yes++ |
| 6E3 + 5G5 | 6E3 | 5G5 | N/A | N/A |
| 7A3 + 10E7 | 7A3 | 10E7 | High (70-80%) | No |
| 7A3 + 10B6 | 7A3 | 10B6 | High (90-100%) | Yes++ |
| 7A3 + 1A11 | 7A3 | 1A11 | High (90-100%) | Yes++ |
| 7A3 + 5G5 | 7A3 | 5G5 | High (90-100%) | Yes |

Table 8 displays that administration of combination of protective mAbs specific for peptides Fba, Met6 or Hwp1 conferred enhanced protection against systemic candidiasis in passive transfer as compared to single mAb treatment. For example, multiple protective mAbs specific for Fba, Met6 or Hwp1 peptide vaccines that were derived from different *C. albicans* cell wall proteins were combined into one cocktail and the combination cocktails were evaluated for protective efficacy in comparison with each protective mAb given alone. Survival data indicates that although the use of individual mAb can be a single prophylactic for infection, the combinations of multiple mAbs (detailed in Table 8) resulted in the best protective efficacies as evidenced by longer survival time, higher survival and significantly reduced/non-detectable CFU in kidneys when compared to group receiving single mAb treatment. This work demonstrates that the combination of monoclonal antibodies is a more efficient immune-protective approach against the disease as compared to single mAb treatment.

TABLE 8

| protective mAb cocktails | Control #1 | control #2 | Protection of mAb cocktails | Protection synergy of combination |
|---|---|---|---|---|
| 3H7 + 6H1 | 3H7 | 6H1 | High (90-100%) | Yes++ |
| 3H7 + 3B5 | 3H7 | 3B5 | High (90-100%) | Yes++ |
| 3H7 + 5B11 | 3H7 | 5B11 | N/A | N/A |
| 7H6 + 6H1 | 7H6 | 6H1 | N/A | N/A |
| 7H6 + 3B5 | 7H6 | 3B5 | High (100%) | Yes++ |
| 7H6 + 5B11 | 7H6 | 5B11 | High (100%) | Yes++ |
| 2D5 + 6H1 | 2D5 | 6H1 | N/A | N/A |
| 2D5 + 3B5 | 2D5 | 3B5 | N/A | N/A |
| 2D5 + 2B10 | 2D5 | 2B10 | High (80-90%) | Yes |
| 3H7 + 2D5 | 3H7 | 2D5 | N/A | N/A |
| 3H7 + 3E2 | 3H7 | 3E2 | High (80-100%) | Yes++ |
| 3H7 + 6G9 | 3H7 | 6G9 | N/A | N/A |
| 3H7 + 9C11 | 3H7 | 9C11 | N/A | N/A |
| 3H7 + 7H5 | 3H7 | 7H5 | High (90-100%) | Yes++ |
| 7H6 + 2D5 | 7H6 | 2D5 | N/A | N/A |
| 7H6 + 3E2 | 7H6 | 3E2 | High (90-100%) | Yes |
| 7H6 + 6G9 | 7H6 | 6G9 | High (90-100%) | Yes++ |
| 7H6 + 9C11 | 7H6 | 9C11 | High (90-100%) | Yes++ |
| 7H6 + 7H5 | 7H6 | 7H5 | N/A | N/A |

Embodiments further comprise chimeric peptide constructs, such as double-peptide constructs, including those feasible for human vaccine immunization approach, and also those that do not require an adjuvant, in induction of protective immunity in mice.

The Utility of Two Peptide Epitopes Combined in One Vaccine for Induction of a Greater Protective Immunity Against Disseminated Candidiasis.

Without wishing to be bound by theory, t double chimeric peptide vaccines can induce greater protection against disseminated candidiasis. For example, one antigenic universal peptide can be conjugated to the N terminus of a second peptide, such as a second antigenic universal peptide, through a linker, such as a double lysine linker (-KK-), to form a double chimeric peptide vaccine. Dendritic cell (DC) based immunization approach can be used to show protective efficacy (6). For example, five mice of each test group can be immunized with the double conjugate construct, the individual peptides themselves, or peptide mixture. Control groups can receive DPBS or DCs only. All the animals were challenged with lethal dose of live *C. albicans* 3153A cells by i.v.

Without wishing to be bound by theory, the double chimeric peptide vaccine, for example that which comprises two peptides expressed on the cell surface of *C. albicans*, can induce greater protective immunity than that induced by each individual peptide or by a simple mixture of both peptides. For example, the mice immunized with the double conjugate will have the least detectable CFUs in kidneys as compared to other immunized groups. The experiment can be terminated after 60 days, at which point CFUs in kidneys can be measured.

Improved Double Peptide Constructs Feasible for Human Use Induced Protection Against Disseminated Candidiasis in Mice without Need for Adjuvant.

Using two identified 14mer protective peptide vaccines as the unit peptide, a panel of double-peptide vaccines can be constructed by inserting various amino acid spacers (such as -KK- or GPSL or RDG, or PADRE (SEQ ID NO: 51)) between the two unit peptides, and adding T cell universal epitope (TT947-967 (SEQ ID NO: 78) or TT830-844(SEQ ID NO: 75)) derived from tetanus toxoid at either N- or C-terminus of the peptide.

To demonstrate protective efficacy, groups of BALB/c mice can be immunized via the simple i.p. injections with each conjugate peptide vaccine, with or without any adjuvant. Following challenge with a lethal dose of *C. albicans* 3153A yeast cells, it is expected that the double-peptide constructs will induce 80-100% protection under adjuvant-free conditions in mice, leading to new peptide vaccine formulas with an immunization approach feasible for human use. It is expected that mice vaccinated with the double-peptide vaccines will survive significantly longer than control DPBS group as well as other immunized groups (p<0.001). It is anticipated that no CFUs or significantly reduced CFUs will be detected in kidneys of the mice immunized with the conjugate vaccines.

Conclusions and Discussion for Improved Double-Peptide Vaccines.

Without wishing to be bound by theory, double peptide vaccine compositions comprising antigenic universal peptides provide solid protection against hematogenously disseminated candidiasis by *C. albicans* in both BALB/c and DAB/2 mice. A significant strength of the vaccine composition is that it contains multiple protective peptide epitopes inducing double protective immunity, feasible for simple i.p. immunization, and induces protection in the absence of an adjuvant. Furthermore, a neutropenic murine model of disseminated infection by three non-*albicans* (NAC) *Candida* spp has been established. Additional searches in the N-terminal region of full-length cell surface proteins of *C. albicans* have been performed, and identified multiple universal peptide candidates expressed at 100% homology by *C. albicans, C. tropicalis, C. glabrata, C. parapsilosis*, and *C. Krusei* (Table 2). Those peptides have the capability to induce strong antibody responses and protective immunity against disseminated candidiasis due to *C. albicans*. Therefore, without wishing to be bound by theory, the inclusion of universal peptides in the new double-peptide constructs provides broad coverage against these other medically significant *Candida* species.

References from This Example, Each of Which are Incorporated by Reference Herein in Their Entireties 1. Wilson, L. S., C. M. Reyes, M. Stolpman, J. Speckman, K. Allen, and J. Beney. 2002. The direct cost and incidence of systemic fungal infections. Value Health 5: 26-34.
2. Pappas, P. G., C. A. Kauffman, D. Andes, D. K. Benjamin, Jr., T. F. Calandra, J. E. Edwards, Jr., S. G. Filler, J. F. Fisher, B.-J. Kullberg, L. Ostrosky-Zeichner, A. C. Reboli, J. H. Rex, T. J. Walsh, and J. D. Sobel. 2009. Clinical practice guidelines for the management of candidiasis: 2009 update by the Infectious Diseases Society of America. Clin. Infect. Dis. 48: 503-535.
3. Pappas, P. G., J. H. Rex, J. Lee, R. J. Hamill, R. A. Larsen, W. Powderly, C. A. Kauffman, N. Hyslop, J. E. Mangino, S. Chapman, H. W. Horowitz, J. E. Edwards, W. E. Dismukes, and NIAID Mycoses Study Group. 2003. A prospective observational study of candidiemia: epidemiology, therapy, and influences on mortality in hosptilaized adult and pediatric patients. Clin. Infect. Dis. 37: 634-643.
4. Claudia, S., and D. Leonardi. 2013. *Candida* Infections, Causes, Targets, and Resistance Mechanisms: Traditional and Alternative Antifungal Agents. BioMed Research International 2013.
5. Spellberg, B. 2011. Vaccines for invasive fungal infections. F1000 Medicine Reports 3: 13.
6. Xin, H., S. Dziadek, D. R. Bundle, and J. E. Cutler. 2008. Synthetic glycopeptide vaccines combining b-mannan and peptide epitopes induce protection against candidiasis. Proc. Natl. Acad. Sci. USA 105: 13526-13531.
7. Xin, H., and J. E. Cutler. 2011. Vaccine and monoclonal antibody that enhance mouse resistance to candidiasis. Clin. Vaccine Immunol. 18: 1656-1667.
8. Xin, H., J. Cartmell, J. J. Bailey, S. Dziadek, D. R. Bundle, and J. E. Cutler. 2012. Self-adjuvanting glycopeptide conjugate vaccine against disseminated candidiasis. PLoS One 7.
9. Xin, H. 2014. Double Chimeric Peptide Vaccine and Monoclonal Antibodies That Protect Against Disseminated Candidiasis. J Vaccines Vaccin 5.
10. Xin, H. 16 A.D. Active immunizations with peptide-DC vaccines and passive transfer with antibodies protect neutropenic mice against disseminated candidiasis. Vaccine 34: 245-251.
11. Filler, S. G., and J. E. Edwards. 1995. When and how to treat serious candidial infections: Concepts and controversies. Curr. Clin. Top. Infect. Dis. 15: 1-18.
12. Chung, J. W., S. O. Lee, S. H. Choi, J. H. Woo, J. Ryu, Y. S. Kim, and N. J. Kim. 2006. Risk factors and outcome for breakthrough candidemia in patients with cancer. Mycoses 49: 114-118.
13. Saylor, C., E. Dadachova, and A. Casadeval. 2009. Monoclonal antibody-based therapies for microbial diseases. Vaccine 27 (Suppl 6): 38-46.
14. Han, Y., and J. E. Cutler. 1995. Antibody response that protects against disseminated candidiasis. Infect. Immun. 63: 2714-2719.
15. Han, Y., M. H. Riesselman, and J. E. Cutler. 2000. Protection against candidiasis by an immunoglobulin G3 (IgG3) monoclonal antibody specific for the same mannotriose as an IgM protective antibody. Infect. Immun. 68: 1649-1654.
16. Son, Y.-I., S. Egawa, T. Tatsumi, R. E. Redlinger, P. Kalinski, and T. Kanto. 2002. A novel bulk-culture method for generating mature dendritic cells from mouse bone marrow cells. J. Immunol. Meth. 262: 145-157.
17. Xin, H., B. L. Granger, S. Dziadek, D. R. Bundle, and J. E. Cutler. 2007. Antigen-pulsed dendritic cells used for identification of carrier peptides and eventual glycopeptide conjugate vaccines against candidiasis. ASM Proc. (Abst).
18. Guinea, J. 2014. Global trends in the distribution of *Candida* species causing candidemia. Clin. Microbiol. Infect. 20: 5-10.
19. Arendrup, M., T. Horn, and N. Frimodt-Moller. 2002. In vivo pathogenicity of eight medically relevant *Candida* species in an animal model. Infection 30: 286-291.
20. MacCallum, D. M. 2012. Hosting Infection: ExperimentalModels to Assay *Candida* Virulence. International Journal of Microbiology 2012: 1-12.

Example 3

Vaccination with Universal Peptide Vaccines in Mice to Demonstrate Induced Protective Antibodies and Protection Against all the Medically Important *Candida* Spp.

Novel universal peptides as described herein can be excellent peptide vaccines against *C. ablicans* infection. The universal peptide vaccines have been tested against other important opportunistic *Candida* species, including *C. tropicalis, C. glabrata* and *C. parapsilosis* in addition to *C. albicans* to demonstrate that the range of protection by a peptide vaccine against disseminated candidiasis can be broadened by incorporating a cell surface peptide generally expressed by medically important *Candida* spp.

By the established powerful DC-based immunization strategy favoring production of antibodies, a subset of the universal *Candida* surface peptide candidates (for example, GPV-M1, GPV-M2, GPV-P1, GPV-P3) was able to provide broad coverage against a variety of medically important *Candida* spp, which cause >85% disseminated candidiasis in humans.

Further, monoclonal antibodies specific to the universal peptides have been produced and/or isolated which demonstrate solid protection in mouse model of disseminated candidiasis caused by *C. albicans, C. tropicalis* and *C. glabrata* (Table 9).

TABLE 9

Universal peptide vaccines protect against disseminated candidiasis caused by C. tropicalis and C. glabrata in addition to C. albicans:

| | | Universal Peptide Vaccines and Related mAbs | | Protection against Candida spp in mouse model | | |
|---|---|---|---|---|---|---|
| Hybridomas | mAb isotype | Peptide vaccine | Peptide Sequences | Against C. albicans | Against C. tropicalis | Against C. glabrata |
| 2C9G3 | IgG2a | GPV-M2 universal | cTTTIGSFPQTKDIR | High (80-100%) | High (60-80%) | High (80-90%) |
| 5A9D1 | IgG3 | GPV-M2 universal | cTTTIGSFPQTKDIR | High (80-90%0 | High (70-90%) | not yet tested |
| 5A11B1 | IgG3 | GPV-M2 universal | cTTTIGSFPQTKDIR | High (60-90%) | High (60-80%) | High (60-90% |
| 6E3D9 | IgG1 | GPV-M1 universal | cFWVNPDCGLKTR | High (80-100%) | High (80-100% | not yet test |
| 1D4H5 | IgG1 | GPV-M1 universal | cFWVNPDCGLKTR | High (70-80%) | High (60-80%) | High (70-90%) |
| 7A3C4 | IgG1 | GPV-M1 universal | cFWVNPDCGLKTR | High (70-90%) | High (80-90%) | High (80-90%) |
| 10E7E2 | IgG1 | GPV-P3-universal | cIVIIGGGDTATVAKK | High (80-100% | High (60-70%) | High (60-70%) |
| 1A11H8 | IgG3 | GPV-P1 universal | cAILGGSKVSDKI | High (60-90%) | High (70-80%) | not yet tested |
| 10B6H8 | IgG1 | GPV-P1 universal | cAILGGSKVSDKI | High (80-100% | High (60-80%) | High (60-70%) |
| 5G5G3 | IgG2a | GPV-P1 universal | cAILGGSKVSDKI | High (80-100% | High (80-90%) | High (60-80%) |

As described herein are examples of universal peptide vaccines that can elicit antibody responses and high degree protection against disseminated candidiasis due to *Candida* spp., such as those described above.

Figure 2:
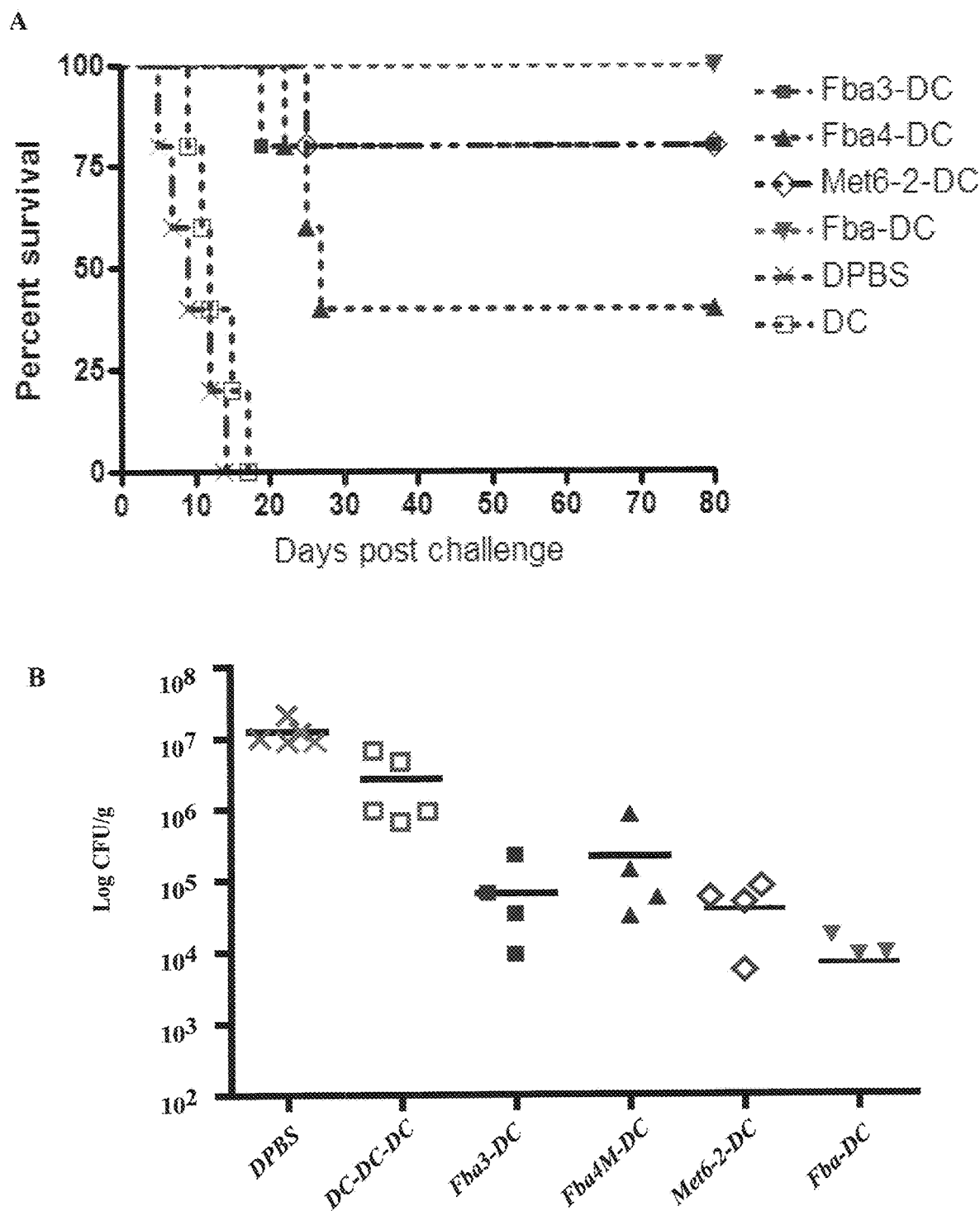
FIG. 2 shows peptide candidates Met6-2, FbaU1 induced high degree protection against disseminated candidiasis caused by *C. albicans* in mice. Peptides Met6-2, Fba3 and FbaU1 induced good protective responses against disseminated candidiasis caused by *C. albicans* (panels A and C, respectively), and the protected groups had reduced or non-detectable CFUs in their kidneys as compared to controls (panels B and D, respectively).

New Universal Peptide Candidates Met6-2, FbaU1 Induced High Degree Protection Against Disseminated Candidiasis Caused by *C. albicans* in Mice To perform rapid throughput evaluation of peptide vaccine candidates, immunizations were done by use of the similar antigen-pulsed DC based vaccine strategy with modification by totally removing CFA from vaccine formula. Fba peptide was used as positive control. All five putative universal peptides [Fba3 (also referred to as FbaU1; SEQ ID NO: 36; FAIPAINVTSSSTVVAALE); Fba4 (SEQ ID NO. 37; SSSTVVAAL); Met6-2 (SEQ ID NO. 38; YDQVLDLSLLFNAIP); FbaU1; and FbaU2 (SEQ ID NO. 80; PAINVTSSSTVVAALEAA)] were able to induce specific antibody responses in BALB/c mice (data not shown), and importantly, peptides Met6-2, Fba3 and FbaU1 induced good protective responses against disseminated candidiasis caused by *C. albicans* (FIG. 2); accordingly, the protected groups had reduced or non-detectable CFUs in their kidneys as compared to controls (FIGS. 2, B and D). Passive transfer of immune sera showed the antibodies are responsible for the protection.

The Range of Protection by Universal Peptide Vaccines can be Broadened to Protect Against Disseminated Candidiasis Caused by *C. tropicalis*

Figure 3:
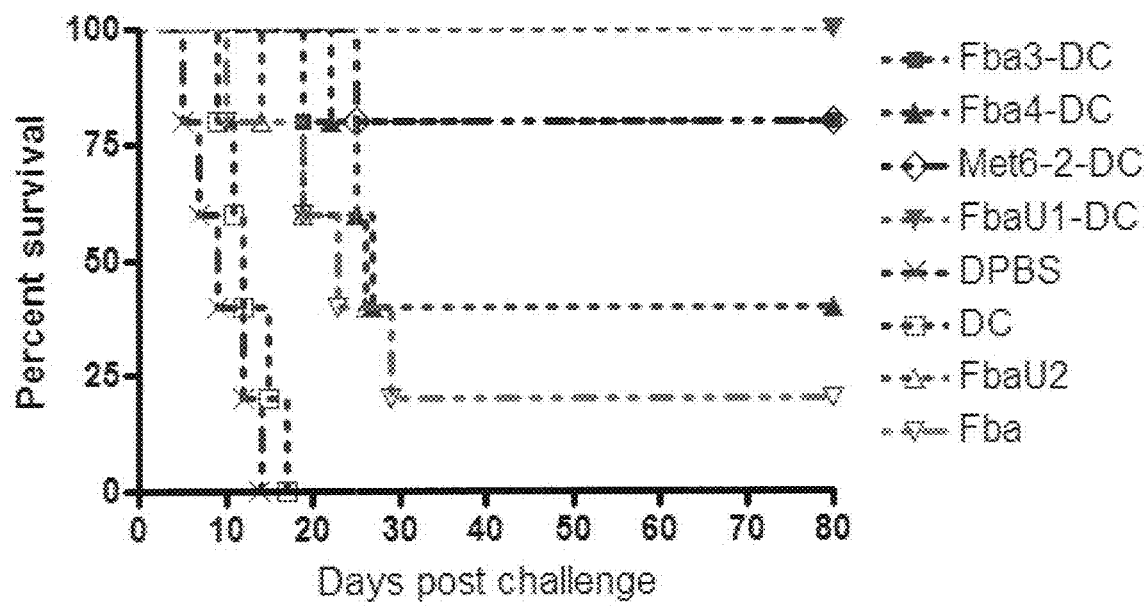
FIG. 3 shows the range of protection by universal peptide vaccines can be broadened to protect against disseminated candidiasis caused by *C. tropicalis*. Peptide FbaU1 induced the best protection (100% survival) among the peptide candidates; both Fba3 and Met6-2 peptides induced good protection with 80% survival up to 80 days (Panel A). CFU data in kidneys of immunized groups are very consistent with the survival data (Panel B), FbaU1, Fba3 and Met6-2 groups had significantly reduced live fungal cells in their kidneys as compared to controls ($p<0.001$).
Figure 3:
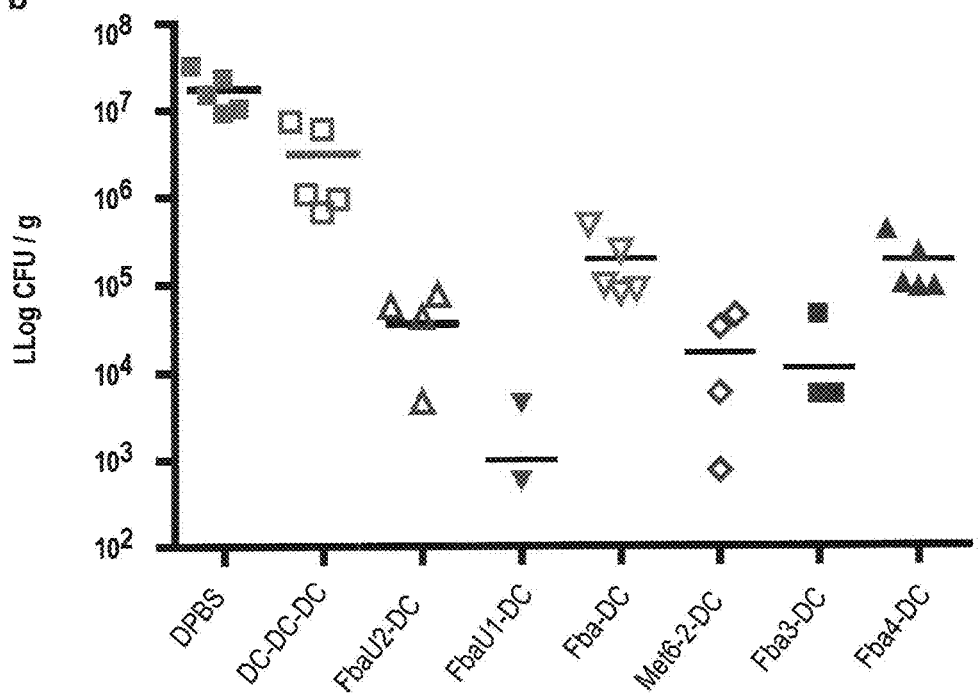

Peptide-vaccinated mice were challenged with lethal dose of live *C. tropicalis* cells (ATCC 20336; i.v. challenge dose: 1×106/mouse). Peptide FbaU1 induced the best protection (100% survival) among the peptide candidates; both Fba3 and Met6-2 peptides induced good protection with 80% survival up to 80 days (FIG. 3A). CFU data in kidneys of immunized groups are very consistent with the survival data (FIG. 3B), FbaU1, Fba3 and Met6-2 groups had significantly reduced live fungal cells in their kidneys as compared to controls (p<0.001).

The Range of Protection by Universal Peptides can be Broadened to Protect Against Disseminated Candidiasis Caused by *C. glabrata*

Figure 4:
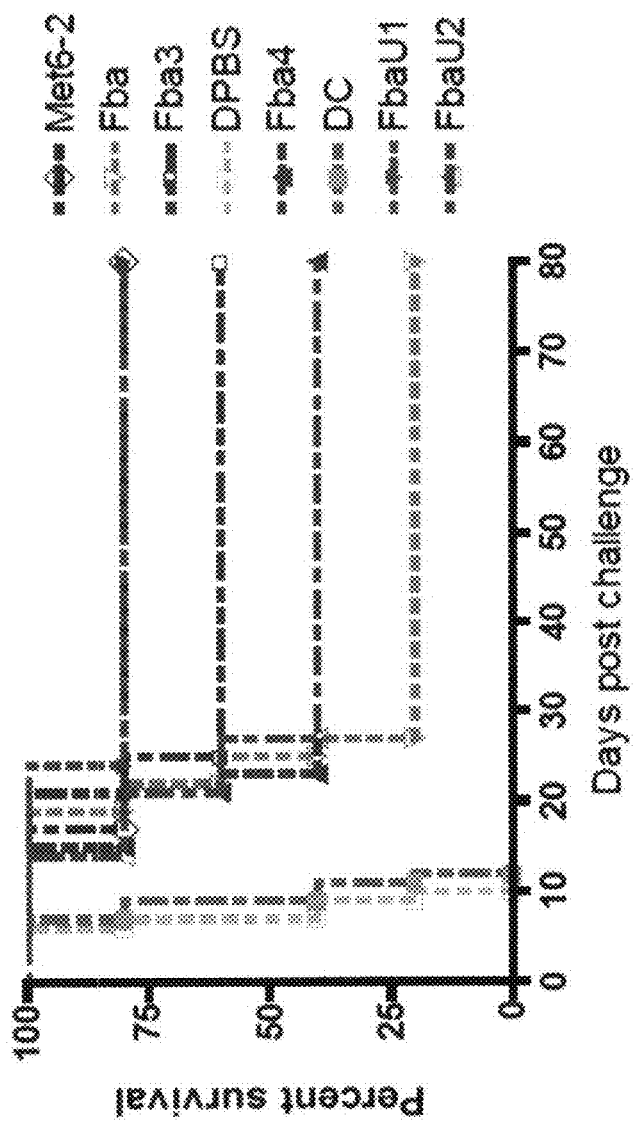
FIG. 4 shows the range of protection by universal peptides can be broadened to protect against disseminated candidiasis caused by *C. glabrata*. Peptide FbaU1& Met6-2 peptides were able to induce a high degree protection.
Figure 5:
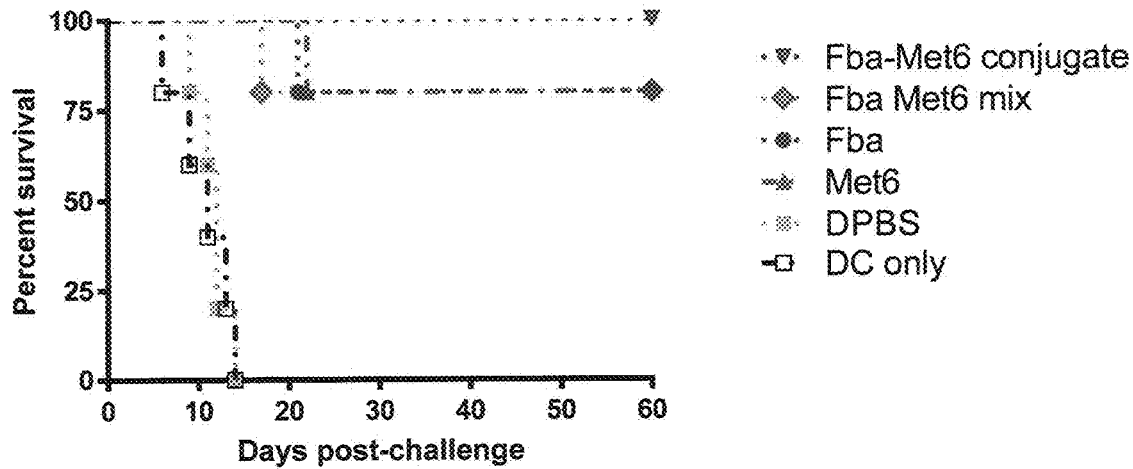
FIG. 5 shows that, when tested in C57BL/6 mice, the tested peptide vaccines are prone to Th1 responses.
Figure 5:
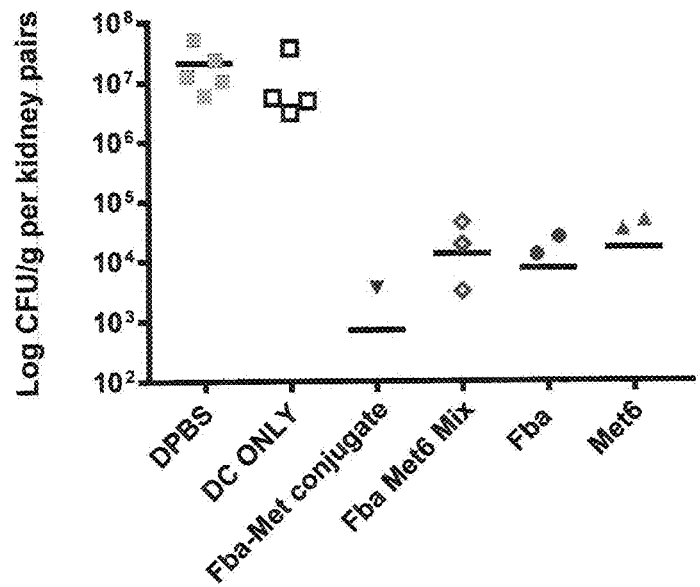

Peptide vaccinated mice were also challenged with *C. glabrata*, which has emerged as the second most common cause of invasive candidiasis in the US. Since *C. glabrata* is not lethal for wild-type mice, immunosuppression in vaccinated mice were induced by cyclophosphamide (50 mg/kg) treatment for two weeks, and then mice were challenged with live *C. glabrata* cells [CBS138 (ATCC 2001), 1×107 cells/mouse]. Peptide FbaU1 & Met6-2 peptides were able to induce a high degree protection (FIG. 4). CFU experiments will be performed and completed. Without wishing to be bound by theory, survival data is correlated with the number of CFUs in kidneys of experimental mice. Expected results comprise a significant reduction in number of CFUs in kidneys of mice vaccinated with peptide FbaU1 or Met6-2 peptide vaccine as compared to controls.

Vaccination with Universal Double Chimeric or Multiple Peptide Vaccines in Mice to Show Enhanced Efficacy and Synergistic Protection Against Disseminated Candidiasis.

TABLE 10

New universal double/multiple peptide vaccines against disseminated candidiasis:

| SEQ ID NO | Double Peptide Vaccine Formula Feasible for Human Use | | Modification |
|---|---|---|---|
| 83 | 1 | PADRE-GPV-M1-GPSL-GPV-P1 | Amidation (C-terminus) and Acetylation (N-terminus) |
| 84 | 2 | TT830-844-GPSL-GPV-M1-GPSL-GPV-P1 | Amidation (C-terminus) and Acetylation (N-terminus) |
| 85 | 3 | TT947-967-GPSL-GPV-M1-GPSL-GPV-P1 | Amidation (C-terminus) and Acetylation (N-terminus) |
| 86 | 4 | RGD-GPV-P3-KK-GPV-M2 | Amidation (C-terminus) and Acetylation (N-terminus) |
| 87 | 5 | RGD-GPV-P3-KK-GPV-M2-KLH | Amidation (C-terminus) and Acetylation (N-terminus) KLH Conjugation on Cysteine |
| 88 | 6 | TT830-844-KK-GPV-P3-KK-GPV-M2 | Amidation (C-terminus) and Acetylation (N-terminus) |
| 89 | 7 | TT947-967-KK-GPV-P3-KK-GPV-M1 | Amidation (C-terminus) and Acetylation (N-terminus) |
| 90 | 8 | RGD-TT830-844-KK-GPV-P3-KK-GPV-M1 | Amidation (C-terminus) and Acetylation (N-terminus) |
| 91 | 9 | RGD-TT947-967-KK-GPV-P3-KK-GPV-M1 | Amidation (C-terminus) and Acetylation (N-terminus) |
| 92 | 10 | PADRE-GPV-M2-KK-GPV-P1 | Amidation (C-terminus) and Acetylation (N-terminus) |
| 93 | 11 | RGD-PADRE=GPV-M2-KK-GPV-P3 | Amidation (C-terminus) and Acetylation (N-terminus) |

As described herein, universal double/multiple peptide vaccines against disseminated candidiasis have been developed. For example, 11 double chimeric peptide vaccines, each with different linkers, have been developed, along with vaccines formulated for human use (Table 10). Each chimeric peptide conjugate comprises two peptide epitopes.

Further, compositions and methods of animal immunizations feasible for human use, for example vaccination without any need for adjuvant, have been developed.

The double chimeric peptide conjugate vaccines have been tested for their abilities to induce specific anti-peptide antibodies and protective immunity against the disease caused by C. albicans. In this example, universal double-peptide vaccines were able to induce robust antibody responses, as well as provided 60-100% survival up to 50 days in immunized mice, which showed enhanced protection as compared to each individual universal peptide vaccine. The enhancement in vaccine efficacy was evidenced by both increased survival and reduced or non-detectable fungal burden (colony forming units, CFUs) in kidneys of animals.

As described herein are double chimeric universal peptide conjugate vaccines composed of peptides universally produced by medically important Candida species in addition to C. albicans. An enhanced immune response offering protection against disseminated candidiasis due to C. albicans was also detected in a mouse model of human disseminated candidiasis.

A subset of the universal double chimeric peptide vaccines detected will be tested to show their protective efficacy against other clinically Candida important species.

Combined Universal-Peptides-Related MAbs Will be Tested for Synergistic Protection Against Disseminated Candidiasis.

Combined universal-peptides-related MAbs have been tested for synergistic protection against disseminated candidiasis to demonstrate combinations of multiple protective MAbs specific to different universal peptides provide an effective form of passive transfer protection.

As described herein the combination of MAbs is a more efficient immunoprotective approach against candidiasis as compared to the single MAb treatment. In this study, the protective efficacy of universal-peptide-related MAbs in combination against disseminated candidiasis was further evaluated. This is important, the use of peptide vaccines, for example, in immunosuppressed patients can potentially be limited, as these patients may not necessarily mount active protective responses.

As described herein, the combination of MAbs is a more efficient immunoprotective approach against candidiasis as compared to the single MAb treatment (Table 12).

Several monoclonal antibodies specific for the defined universal peptide vaccines have been obtained by use of standard hybridoma techniques. Development of peptide-specific MAbs provided an unlimited supply of protective antibodies for in vivo applications. Initial results demonstrate that MAbs combination (M2-4/E2-9) treatment provides the best protection (100% survival) as compared to single MAb treatment. Such results have been extended to include specific for novel universal peptides.

TABLE 11 universal double-peptide vaccines induce solid and synergistic protection.

| Double Peptide vaccine formula feasible for human use | Protection against Candidiasis in mouse model | Synergy |
|---|---|---|
| 1. PADRE-GPV-M1-GPSL-GPV-P1 | High (60-90%) | ++ |
| 2. TT830-844-GPSL-GPV-M1-GPSL-GPV-P1 | medium (40-60%) | |
| 3. TT947-967-GPSL-GPV-M1-GPSL-GPV-P1 | medium (40-60%) | |
| 4. RGD-GPV-P3-KK-GPV-M2 | High (70-90%) | ++ |
| 5. RGD-GPV-P3-KK-GPV-M2-KLH | High (80-100%) | ++ |
| 6. TT830-844-KK-GPV-P3-KK-GPV-M2 | medium (40-60%) | |
| 7. TT947-967-KK-GPV-P3-KK-GPV-M1 | High (70-90%) | |
| 8. RGD- TT830-844-KK-GPV-P3-KK-GPV-M1 | High (80-100%) | ++ |
| 9. RGD- TT947-967-KK-GPV-P3-KK-GPV-M1 | Low (20-40%) | |
| 10. PADRE-GPV-M2-KK-GPV-P1 | Low (20-40%) | |
| 11. RGD- PADRE-GPV-M2-KK-GPV-P3 | High (80-100%) | ++ |

TABLE 12

Combinations of multiple protective MAbs that specific to different universal peptides may provide the most effective form of passive transfer protection.

| Therapeutic mAb cocktails | Control #1 | control #2 | Protection of mAb cocktails | Synergy of combination |
|---|---|---|---|---|
| 2C9G3 + 10E7E2 | 2C9G3 | 10E7E2 | High (80-100%) | Yes+++ |
| 5A9D1 + 10E7E2 | 5A9D1 | 10E7E2 | High (80-90%) | Yes++ |
| 1D4H5 + 1A11H8 | 1D4H5 | 1A11H8 | High (80-90%) | No |
| 6E3D9 + 10B6H8 | 6E3D9 | 10B6H8 | High (80-100%) | No |
| 7A3C4 + 5G5G3 | 7A3C4 | 5G5G3 | High (70-90%) | Yes++ |
| 5A11B1 + 10E7E2 | 5A11B1 | 10E7E2 | High (90-100%) | Yes++ |

Example 4

2B10C1 IgG1 mAb Sequencing Results and Analysis

Five single colonies with correct $V_H$ and $V_L$ insert sizes were sent for sequencing The $V_H$ and $V_L$ genes of five different clones (see the attached file for sequence and sequence alignment for details) were found nearly identical. The consensus sequence, listed below, is believed to be the sequence of the antibody produced by the hybridoma 2B10C1.

Heavy chain variable region: DNA sequence (405 bp) (SEQ ID NO: 59)

Leader sequence—FR1—CDR1—FR2—CDR2—FR3—CDR3—FR4

ATGGGATGGAGCTATATCATCCTCTTCTTGTTAGCAACAGCTAC

ACGTGTCCACTCCCAGGTCCAACTGCAGCAGCCTGGGGCTGAGGTGGTGAGGC

CTGGGGCTTCAGTGAAGGTGTCCTGCAAGGCTTCTGGCTACACGGTCAGCAGCTA

CTGGATGAGCTGGGTTAAGCAGAGGCCGGAGCAAGGCCTTGAGTGGATTGGAAG

GATTGATCCTTACGATAGTGAAACTCACTACAATCAAAAGTTCAAGGACAAGGC

CATATTGACTGTAGACAAATCCTCCAGCACAGCCTACATGCAACTCAGCAGCCTG

ACATCTGAGGACTCTGCGGTCTATTACTGTGCAAGGACGGCCGCTTCGTTTGACT

ATTGGGGCCAAGGCACCACTCTCACAGTCTCCTCA

Heavy chain: Amino acids sequence (135 AA) (SEQ ID NO: 60)

Leader sequence-FR1-CDR1-FR2-CDR2-FR3-CDR3-FR4

MGWSYIILFLLATATRVHSQVQLQQPGAEVVRPGASVKVSCKASGY

TVSSYWMSWVKQRPEQGLEWIGRIDPYDSETHYNQKFKDKAILTVDKSSSTAYMQL

SSLTSEDSAVYYCARTAASFDYWGQGTTLTVSS

Light chain: DNA sequence (393 bp) (SEQ ID NO: 61)

Leader sequence-FR1-CDR1-FR2-CDR2-FR3-CDR3-FR4

ATGAAGTTGCCTGTTAGGCTGTTGGTGCTGATGTTCTGGATTC

CTGCTTCCAGCAGTGATGTTGTGATGACCCAAACTCCACTCTCCCTGCCTGTCA

GTCTTGGAGATCAAGCCTCCATCTCTTGCAGATCTAGTCAGAGCCTTGTACACAG

TAATGGAAACTCCTATTTACATTGGTACCTGCAGAAGCCAGGCCAGTCTCCAAAG

CTCCTGATCTACAAAGTTTCCAACCGATTTTCTGGGGTCCCAGACAGGTTCAGTG

GCAGTGGATCAGGGACAGATTTCACACTCAATATCAGCAGAGTGGAGGCTGAGG

ATCTGGGAGTTTATTTCTGCTCTCAAAGTACACATGTTCCATTCACGTTCGGCTCG

GGGACAAAGTTGGAAATAAAA

Light chain: Amino acids sequence (131 AA) (SEQ ID NO: 62)

Leader sequence-FR1-CDR1-FR2-CDR2-FR3-CDR3-FR4

MKLPVRLLVLMFWIPASSSDVVMTQTPLSLPVSLGDQASISCRSSQSL

VHSNGNSYLHWYLQKPGQSPKLLIYKVSNRFSGVPDRFSGSGSGTDFTLNISRVEAE

DLGVYFCSQSTHVPFTFGSGTKLEIK

Example 5

1D4H5 IgG1 GPV-M1 mAb Sequencing Results and Analysis

Five single colonies with correct $V_H$ and $V_L$ insert sizes were sent for sequencing. The $V_H$ and $V_L$ genes of five different clones were found nearly identical. The consensus sequence, listed below, is believed to be the sequence of the antibody produced by the hybridoma 1D4H5.

Heavy chain: DNA sequence (399 bp) (SEQ ID NO: 63)

Leader sequence-FR1-CDR1-FR2-CDR2-FR3-CDR3-FR4

ATGTACTTGGGACTGAACTGTGTATTCATAGTTTTTCTCTTAAA

AGGTGTCCAGAGTGAAGTGAAGCTTGAGGAGTCTGGAGGAGGCTTGGTGCAAC

CTGGAGGATCCATGAAACTCTCCTGTGTTGCCTCTGGATTCACTTTCAGTAACTAC

TGGATGAACTGGGTCCGCCAGTCTCCAGAGAAGGGGCTTGAGTGGGTTGCTGAA

ATTAGATTGAAATCTAATAATTATGCAACACATTATGCGGAGTCTGTGAAAGGCGA

GGTTCACCATCTCAAGCGATGATTCCAAAAGTAGTGTCTACCTGCAAATGAACAA

CTTAAGAGCTGAAGACACTGGCATTTATTACTGTTCAACGGGAACTACTGGGGC

CAAGGCACCACTCTCACAGTCTCCTCA

Heavy chain: Amino acids sequence (133 AA) (SEQ ID NO: 64)

Leader sequence-FR1-CDR1-FR2-CDR2-FR3-CDR3-FR4

MYLGLNCVFIVFLLKGVQSEVKLEESGGGLVQPGGSMKLSCVASGF

TFSNYWMNWVRQSPEKGLEWVAEIRLKSNNYATHYAESVKGRFTISSDDSKSSVYL

QMNNLRAEDTGIYYCSTGNYWGQGTTLTVSS

Light chain: DNA sequence (390 bp) (SEQ ID NO: 65)

Leader sequence-FR1-CDR1-FR2-CDR2-FR3-CDR3-FR4

-continued

ATGGATTTTCAGATGCAGATTATCAGCTTGCTGCTAATCAGTGT

CACAGTCATAGTGTCTAATGGAGAAATTGTGCTCACCCAGTCTCCAACCACCAT

GGCTGCATCTCCGGGGAGAAGATCACTATCACCTGCAGTGCCAGCTCAACTATA

AGTTCCAATTACTTGCATTGGTATCAGCAGAAGCCAGGATTCTCCCCTAAACTCT

TGATTTATAGGACATCCAATCTGGCTTCTGGAGTCCCAGCTCGCTTCAGTGGCAG

TGGGTCTGGGACCTCTTACTCTCTCACAATTGGCACCATGGAGGCTGAAGATGTT

GCCACTTACTACTGCCAGCAGGGTAGTACTATATCACGCACGTTCGGCTCGGGGA

CAAAGTTGGAAATAAAA

Light chain: Amino acids sequence (130 AA) (SEQ ID NO: 66)

[Leader sequence-FR1-CDR1-FR2-CDR2-FR3-CDR3-FR4

MDFQMQIISLLLISVTVIVSNGEIVLTQSPTTMAASPGEKITITCSASST

ISSNYLHWYQQKPGFSPKLLIYRTSNLASGVPARFSGSGSGTSYSLTIGTMEAEDVAT

YYCQQGSTISRTFGSGTKLEIK

Example 6

2D5F7 IgG2b mAb Sequencing Results and Analysis

Five single colonies with correct $V_H$ and $V_L$ insert sizes were sent for sequencing. The $V_H$ and $V_L$ genes of five different clones were found nearly identical. The consensus sequence, listed below, is believed to be the sequence of the antibody produced by the hybridoma 2D5F7.

Heavy chain: DNA sequence (420 bp) (SEQ ID NO: 67)

Leader sequence-FR1-CDR1-FR2-CDR2-FR3-CDR3-FR4

ATGGAAAGGCACTGGATCTTTCTCTTCCTGTTGTCAGTAACTGC

AGGTGTCCACTCCCAGGTCCAGCTGCAGCAGTCTGCAGCTGAACTGGCAAGAC

CTGGGGCCTCAGTGAAGATGTCCTGCAAGGCTTCCTGGCTACACCTTTAGTAGCTA

CACGATGCACTGGGTAAAACAGAGGCCTGGACAGGGTCTGGAATGGATTGGATA

CATTAATCCTAGCAGTGGATATACTGATTACAATCAGAAGTTCAAGGACAAGGC

CACATTGACTGCAGACAAATCCTCCAGCACAGCCTACATGCAACTGAGCAGCCT

GACATCTGAGGACTCTGCGGTCTATTACTGTGCAAGACTATATGATAACTACGA

TACTATGCTATGGACTACTGGGGTCAAGGAACCTCAGTCACCGTCTCCTCA

Heavy chain: Amino acids sequence (140 AA) (SEQ ID NO: 68)

Leader Sequence-FR1-CDR1-FR2-CDR2-FR3-CDR3-FR4

MERHWIFLFLLSVTAGVHSQVQLQQSAAELARPGASVKMSCKASGY

TFSSYTMHWVKQRPGQGLEWIGYINPSSGYTDYNQKFKDKTTLTADKSSSTAYMQL

SSLTSEDSAVYYCARLYDNYDYYAMDYWGQGTSVTVSS

Light chain: DNA sequence (396 bp) (SEQ ID NO: 69)

Leader Sequence-FR1-CDR1-FR2-CDR2-FR3-CDR3-FR4

ATGGATTCACAGGCCCAGGTTCTTATATTGCTGCTGCTATGGGT
ATCTGGTACCTGTGGGGACATTGTGATGTCACAGTCTCCATCCTCCCTGGCTGTG

TCAGCAGGAGAGAAGGTCACTATGAGCTGCAAATCCAGTCAGAGTCTGCTCAATA

GTAGAATCCGAAAGAACTACTTGGCTTGGTACCAGCAGAAACCAGGGCAGTCTCC

TAAACTGCTGATCTACTGGGCATCCACTAGGGAATCGGGGTCCCTGATCGCTTC

TCAGCAGGAGAGAAGGTCACTATGAGCTGCAAATCCAGTCAGAGTCTGCTCAATA

ACAGGCAGTGGATCTGGGACAGATTTCACTCTCACCATCAGCAGTGTGCAGGCTG

ATGACCTGGCAGTTTATTACTGCAAGCAATCTTATAATCTGCTCACGTTCGGTGC

GGGACCAAGCTGGAGCTGAAA

Light chain: Amino acids sequence (132 AA) (SEQ ID NO: 70)

Leader Sequence-FR1-CDR1-FR2-CDR2-FR3-CDR3-FR4

MDSQAQVLILLLLWVSGTCGDIVMSQSPSSLAVSAGEKVTMSCKSSQ

SLLNSRIRKNYLAWYQQKPGQSPKLLIYWASTRESGVPDRFTGSGSGTDFTLTISSVQ

ADDLAVYYCKQSYNLLTFGAGTKLELK

Example 7

10E7E2 IgG1 GPV-P3 mAb Sequencing Results and Analysis

Five single colonies with correct $V_H$ and $V_L$ insert sizes were sent for sequencing. The $V_H$ and $V_L$ genes of five different clones were found nearly identical. The consensus sequence, listed below, is believed to be the sequence of the antibody produced by the hybridoma 10E7E2.

Heavy chain: DNA sequence (405 bp) (SEQ ID NO: 71)

Leader Sequence-FR1-CDR1-FR2-CDR2-FR3-CDR3-FR4

ATGGCTGTCTTGGGGCTGCTGCTCTTCTGCCTGGTGACATTCCCAA
GCTGTGTCCCATCCCAGGTGCAGCTGAAGCAGTCAGGACCTGGCCTAGTGCAG

CCCTCACAGAGCCTGTCCATCACCTGCACAGTCTCTGGTTTCTCATTAACAGCTA

TGGTGTACACTGGGTTCGCCAGTCTCCAGGAAAGGGTCTGGAGTGGCTGGGAGT

GATATGGAGTGGTGGAACTACAGACTATAATGCAGCTTTCATATCCAGACTGAG

ATCAGCAAGGACAATTCCAAGAGCCAAGTTTTCTTTAAAAATGAACAGTCTGCAA

GCTAATGACACAGCCATATATTACTGTGCCAGAGGGGGGCACCGAGGGTTTGCTT

ACTGGGGCCAAGGGACTCTGGTCACTGTCTCTGCA

Heavy chain: Amino acids sequence (135 AA) (SEQ ID NO: 72)

Leader Sequence-FR1-CDR1-FR2-CDR2-FR3-CDR3-FR4

MAVLGLLFCLVTFPSCVPSQVQLKQSGPGLVQPSQSLSITCTVSGFSL

TSYGVHWVRQSPGKGLEWLGVIWSGGTTDYNAAFISRLSISKDNSKSQVFFKMNSL

QANDTAIYYCARGGHRGFAYWGQGTLVTVSA

Light chain: DNA sequence (393 bp) (SEQ ID NO: 73)

Leader sequence—FR1—CDR1—FR2—CDR2—FR3—CDR3—FR4

ATGGGCATCAAGATGGAGACACATTCTCAGGTCTTTGTATACA

TGTTGCTGTGGTTGTCTGGTGTTGAAGGAGACATTGTGATGACCCAGTCTCAC

AAATTCATGTCCACATCAGTAGGAGACAGGGTCAGCATCACCTGCAAGGCCAGT

CAAGATGTGGGTACTGCTGTAGCCTGGTATCAACAGAAACCAGGGCAATCTCCT

AAACTACTGATTTACTGGGCATCCACCCGGCACACTGGAGTCCCTGATCGCTTCA

CAGGCAGTGGATCTGGGACAGATTTCACTCTCACCATTAGCAATGTGCAGTCTGA

AGACTTGGCAGATTATTTCTGTCAGCAATATAGCAGCTATCCTCTCACGTTCGGT

GCTGGGACCAAGCTGGAGCTGAAA

Light chain: Amino acids sequence (131 AA) (SEQ ID NO: 74)

Leader sequence—FR1—CDR1—FR2—CDR2—FR3—CDR3—FR4

MGIKMETHSQVFVYMLLWLSGVEGDIVMTQSHKFMSTSVGDRVSI

TCKASQDVGTAVAWYQQKPGSPKLLIYWASTRHTGVPDRFTGSGSGTDFTLTISNV

QSEDLADYFCQQYSSYPLTFGAGTKLELK

Example 8

MAbs Provided Enhanced Resistance to Disseminated Candidiasis in Neutropenic Mice.

Figure 6:
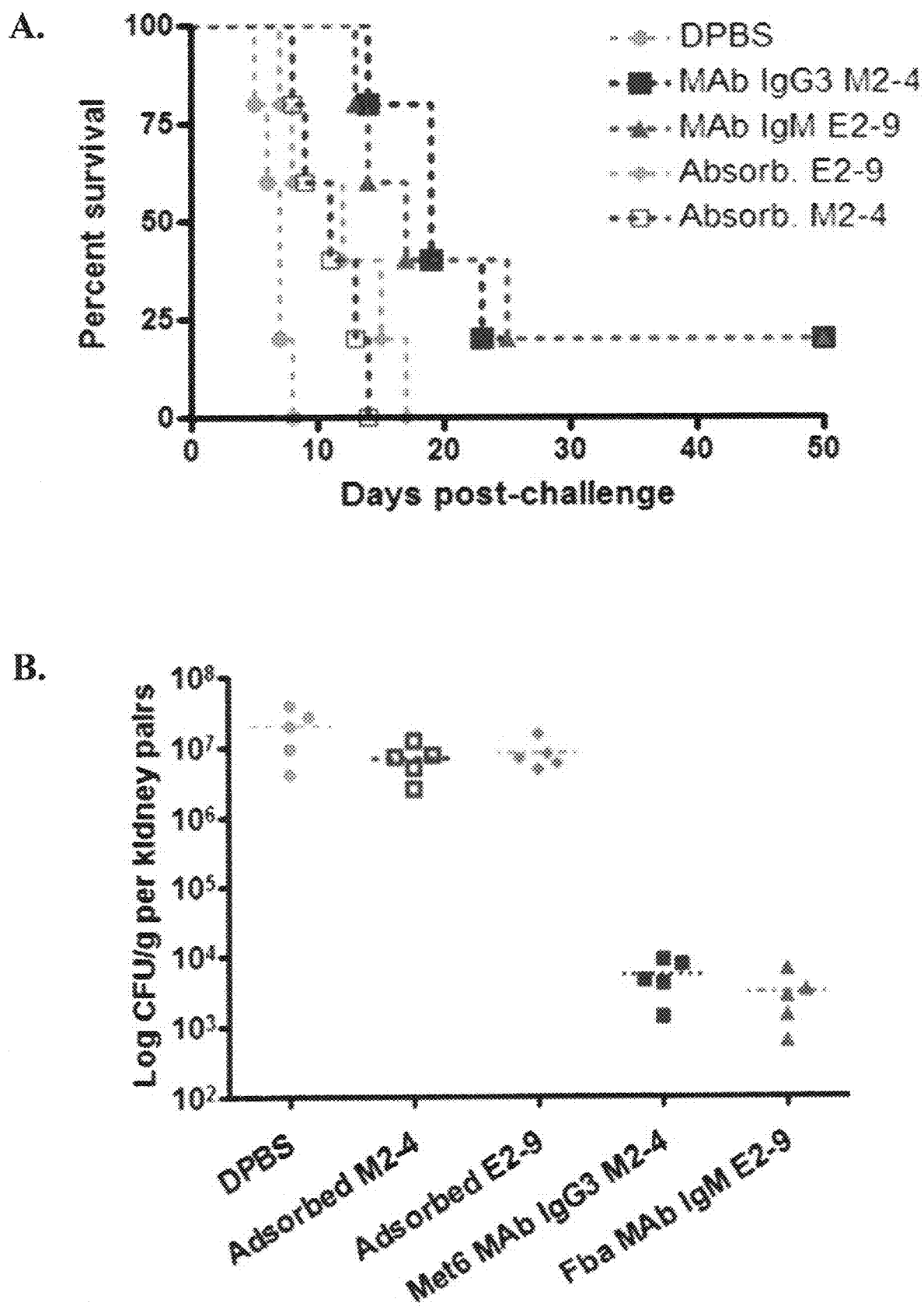
FIG. 6 shows passive immunization with mAbs E2-9 and M2-4 enhanced resistance of neutropenic mice to disseminated candidiasis. (A) Neutropenic mice received 0.5 ml of either mAb M2-4 or mAb E2-9 (one dose) had significantly prolonged survival as compared to control animals that received DPBS or absorbed mAbs, $p<0.05$; (B) Consistently, the groups received treatment of either protective mAb (M2-4 and E2-9) had significantly reduced CFUs in kidneys compared with control mice, $p<0.001$. (C) After challenge, some groups of mice were given the same dose of antibodies (mAb E2-9 or MAb M2-4) as above or control materials on every other day post-challenge for two weeks. The survival of recipients was significantly improved ($p<0.01$). As compared to one-dose treatment, treatment with mAb M2-4 for two weeks was able to increase protection from 20% to 40%; with MAB E2-9, from 20% to 60%. (D) Groups received mAb treatment for two weeks had significantly reduced CFUs in kidneys as compared with control animals that received DPBS or absorbed mAbs ($p<0.001$).
Figure 7:
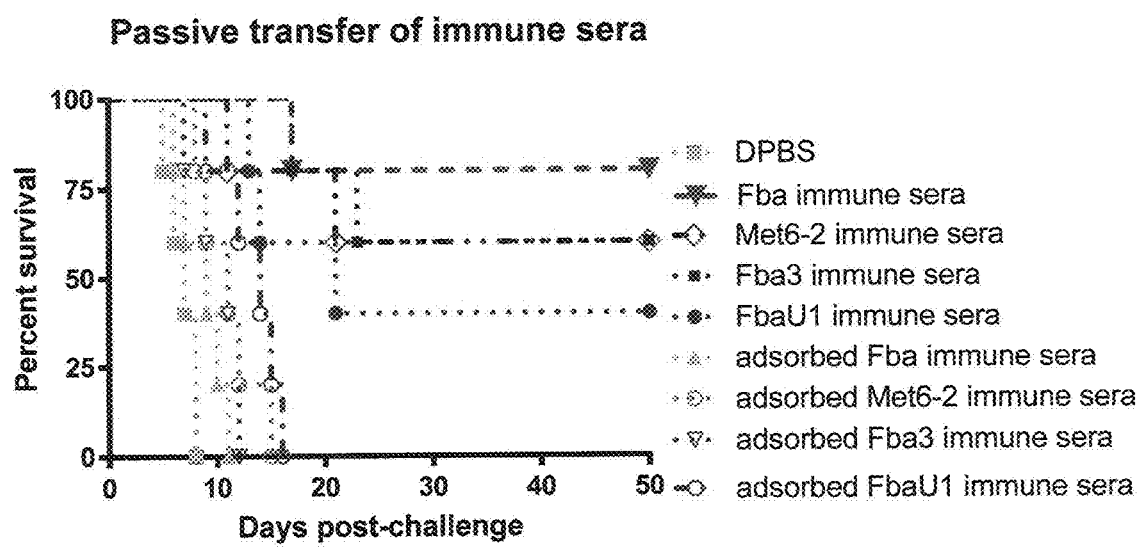
FIG. 7 shows passive transfer of immune sera.
Figure 9:
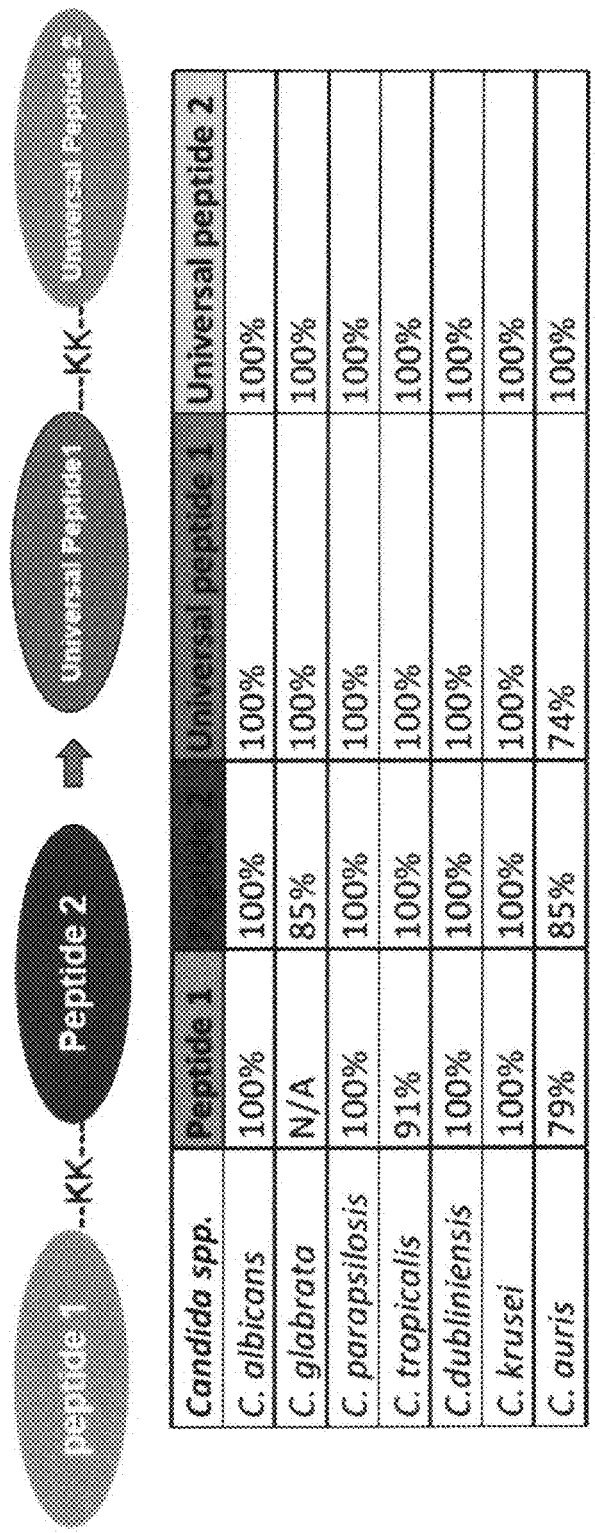
FIG. 9 shows a schematic of an embodiment comprising a synthetic chimeric peptide vaccine against invasive fungal infections.
Figure 10:
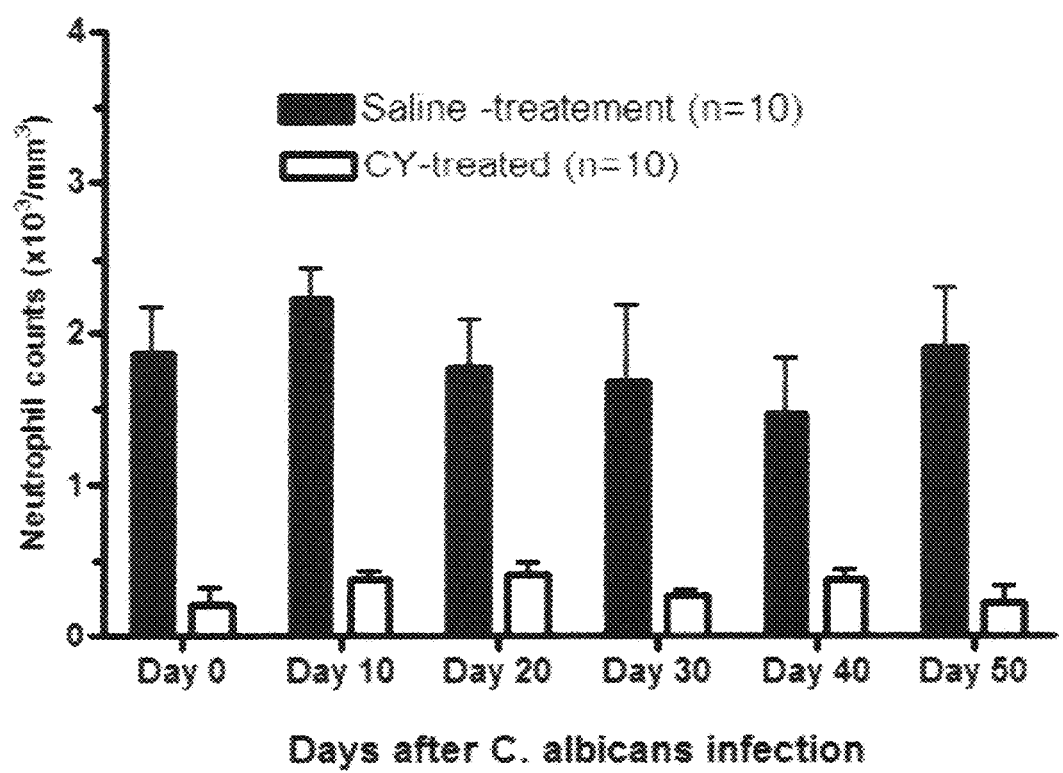
FIG. 10 shows a neutropenic mouse model of human disseminated candidiasis.
Figure 11:
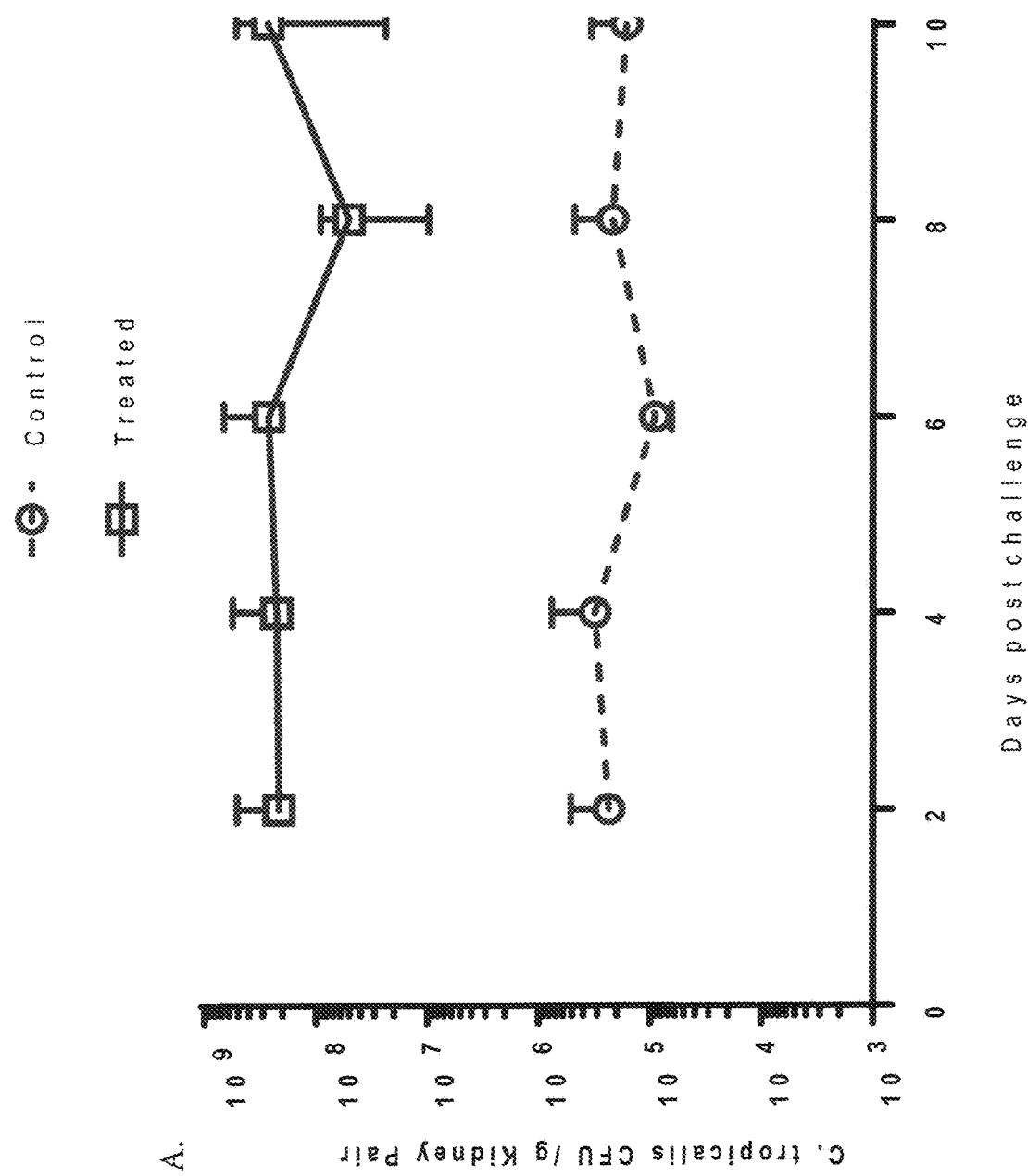
FIG. 11 shows the effect of immunosuppression on kidney fungal burden (NAC).
Figure 11:
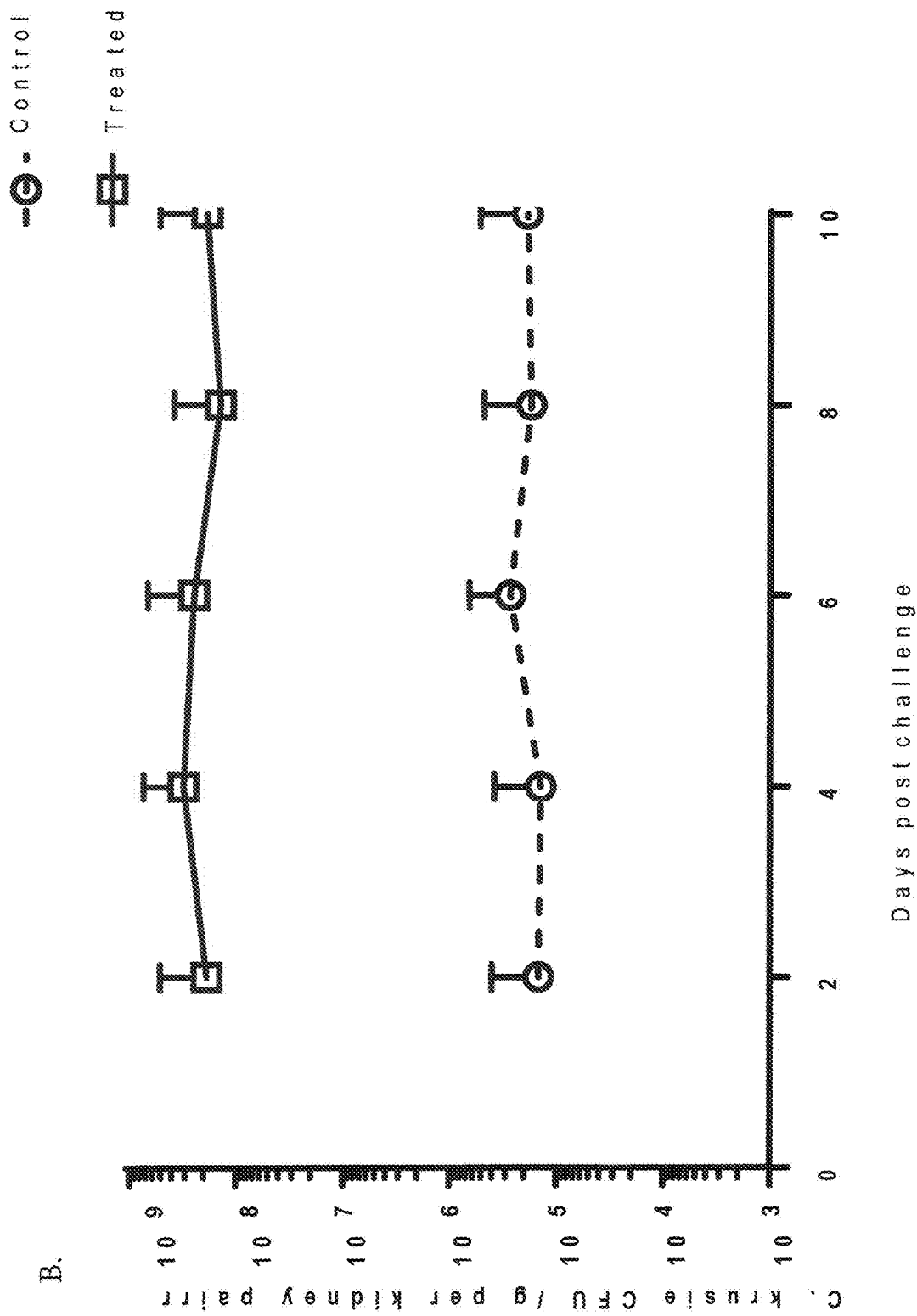
Figure 12:
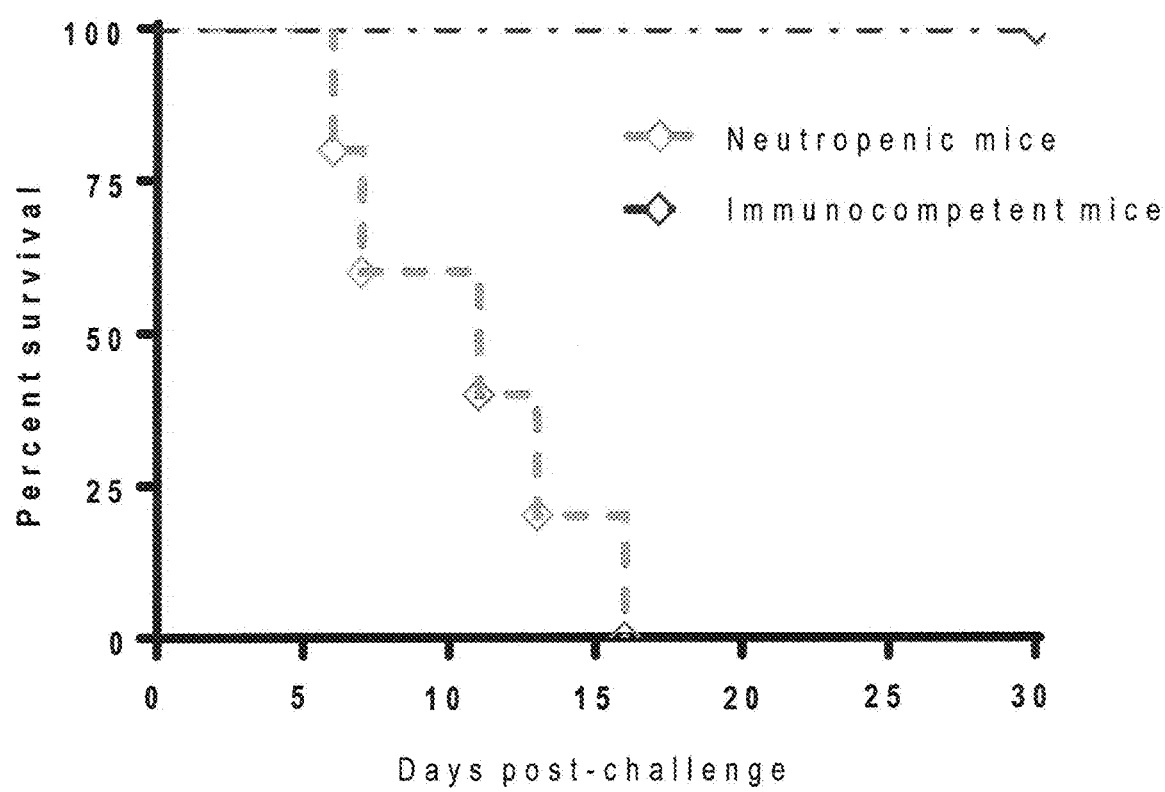
FIG. 12 shows a neutropenic mouse model of NAC.
Figure 12:
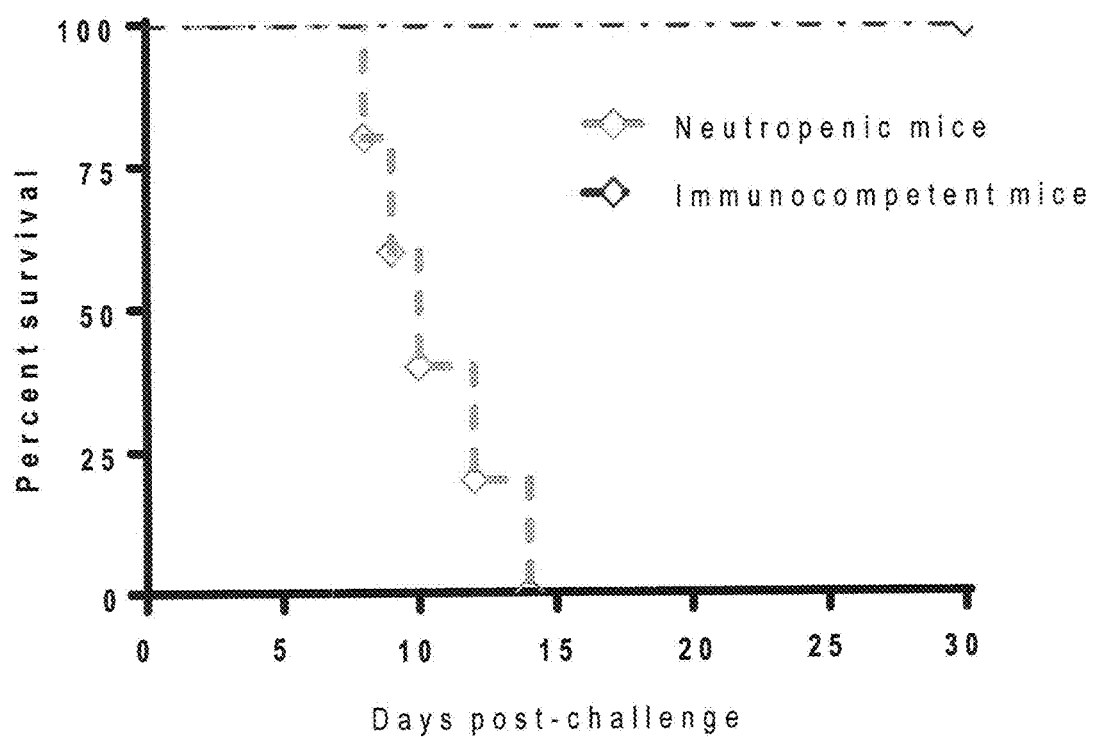
Figure 12:
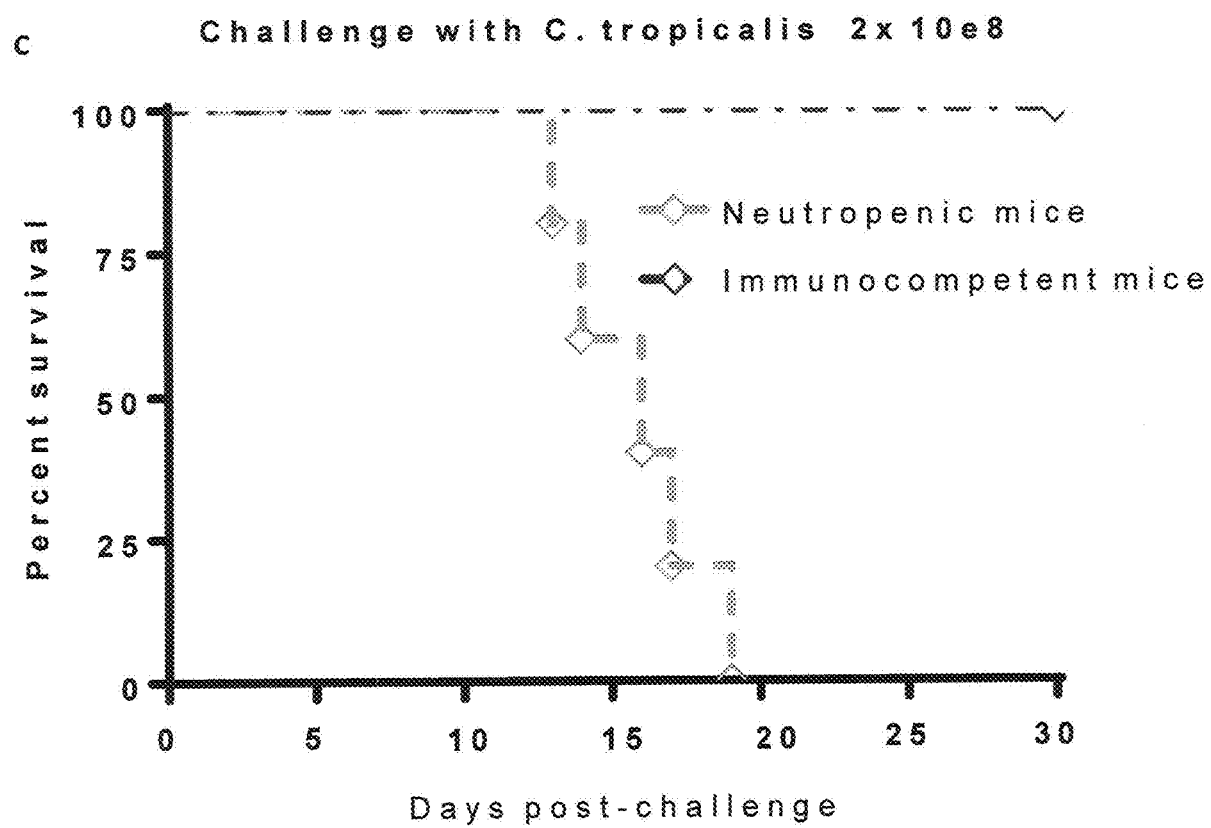
Figure 13:
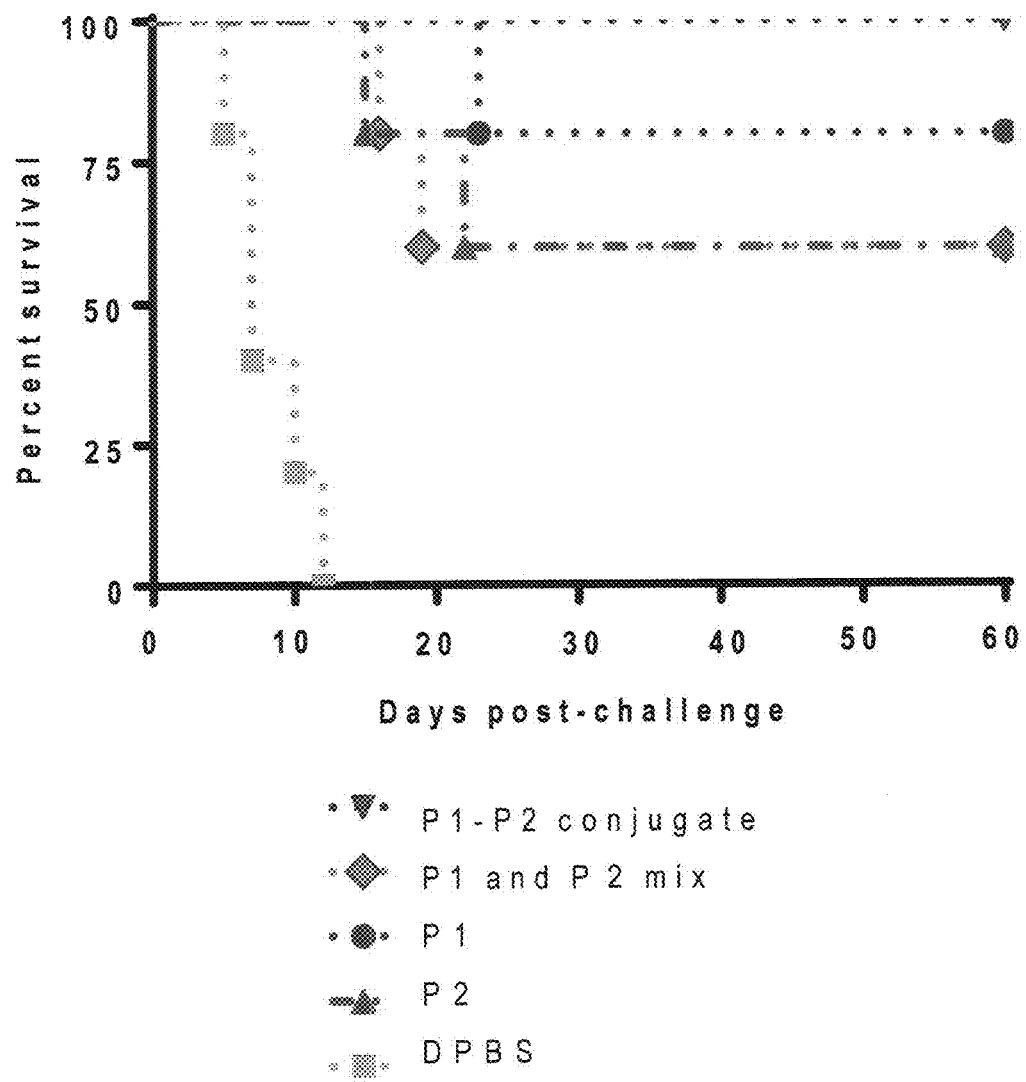
FIG. 13 shows double peptide conjugate vaccines induced protection against disseminated candidiasis caused by medically important *candida* species.
Figure 13:
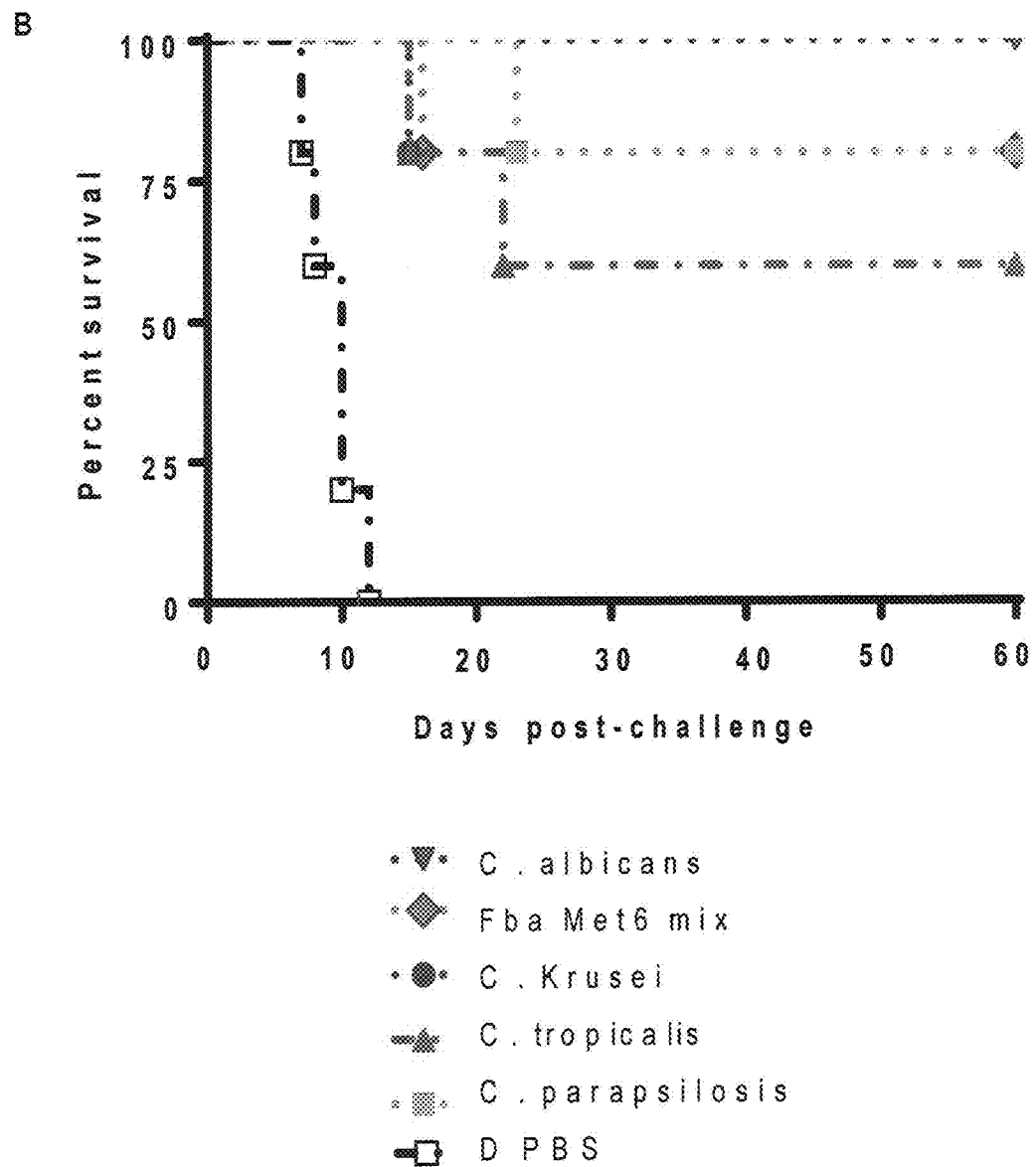

The possibility of using passive mAb immunotherapy in neutropenic mice can be evaluated. As an example, the protective effect of mAb specific for antigenic universal peptides against disseminated candidiasis in neutropenic mice can be examined by passive transfer experiments. To verify that the protection elicited by antibodies is indeed due to mAbs, control groups can receive mAbs absorbed with *C. albicans* yeast cells. For example, mice can receive either the mAb itself, in one dose or multiple doses during 14 day period, or absorbed mAbs. Without wishing to be bound by theory, it is expected that the group receiving treatment of protective mAb will have significantly reduced CFUs in kidneys compared with control mice. When each mAb is given every other day for two weeks, mAb is expected to be able to increase protection, such as from 20% to 40%, or from 20% to 60%, with similar improved efficacy as we observed in immunocompetent mice. As an example, see FIG. 6.

Example 9

MAbs have Therapeutic Activity for Disseminated Candidiasis.

The therapeutic efficacy of mAb, such as those specific for antigenic universal peptides, can be examined in the murine model of disseminated candidiasis. Without wishing to be bound by theory, it is expected that data resulting from the kidney-CFU measurement will show that the administration of such mAbs to BLAB/c mice at 1 h, 2 h, 4 h post-infection will exert a therapeutic potential to the disseminated disease, whereas administrations of mAbs at 8 h, 12 h or 24 h post-infection will not be effective.

Example 10

Combined two universal-peptide-specific mAbs (mAb cocktails) conferred enhanced protection against systemic candidiasis in passive transfer as compared to single mAb treatment.

TABLE 13

| protective mAb cocktails | Control #1 | control #2 | Protection of mAb cocktails | Synergy of combinations | Protection of adsorbed mAb cocktails or mAb |
|---|---|---|---|---|---|
| 2C9 + 1A11 | 2C9 | 1A11 | High (90-100%) | Yes++ | None |
| 2C9 + 10B6 | 2C9 | 10B6 | High (90-100%) | Yes++ | None |
| 2C9 + 5G5 | 2C9 | 5G5 | N/A | N/A | None |
| 2C9 + 10E7 | 2C9 | 10E7 | High (70-80%) | No | None |
| 5A9 + 10E7 | 5A9 | 10E7 | High (100%) | Yes++ | None |
| 5A9 + 1A11 | 5A9 | 1A11 | High (100%) | Yes++ | None |
| 5A9 + 10B6 | 5A9 | 10B6 | High (70-80%) | No | None |
| 5A9 + 5G5 | 5A9 | 5G5 | N/A | N/A | None |
| 6E3 + 10E7 | 6E3 | 10E7 | High (80-90%) | Yes | None |
| 6E3 + 10B6 | 6E3 | 10B6 | High (70-80%) | No | None |
| 6E3 + 1A11 | 6E3 | 1A11 | High (100%) | Yes++ | None |
| 6E3 + 5G5 | 6E3 | 5G5 | N/A | N/A | None |
| 7A3 + 10E7 | 7A3 | 10E7 | High (70-80%) | No | None |
| 7A3 + 10B6 | 7A3 | 10B6 | High (90-100%) | Yes++ | None |
| 7A3 + 1A11 | 7A3 | 1A11 | High (90-100%) | Yes++ | None |
| 7A3 + 5G5 | 7A3 | 5G5 | High (90-100%) | Yes | None |

Passive protection against disseminated candidiasis caused by *C. albicans* was prevented by removal of the mAbs by absorption with *Candida* cells before transfer.

TABLE 14

Hybridoma clone, peptide vaccines, and related protective peptide-specific mAbs

| Hybridomas | mAbs | mAb isotype | Peptide vaccine | Protection | Protection of adsorbed mAb |
|---|---|---|---|---|---|
| 3H7E3 | 3H7 | IgG1 | Met6 peptide SEQ ID NO: 30 | High (70-90%) | None |
| 5E12D10 | 5E12 | IgG1 | Met6 peptide SEQ ID NO: 30 | High (90-100%) | None |
| 2B10C1 | 2B10 | IgG1 | Met6 peptide SEQ ID NO: 30 | High (80-100%) | None |
| 7H6A2 | 7H6 | IgG2b | Met6 peptide SEQ ID NO: 30 | High (80-90%) | None |
| 6H1G8 | 6H1 | IgG2b | Hwp1 peptide SEQ ID NO: 31 | High (70-80%) | None |
| 3B5H7 | 3B5 | IgG2b | Hwp1 peptide SEQ ID NO: 31 | High (70-80%) | None |
| 5B11H1 | 5B11 | IgG1 | Hwp1 peptide SEQ ID NO: 31 | High (90-100%) | None |
| 2D5F7 | 2D5 | IgG2b | Fba peptide SEQ ID NO: 29 | High (90-100%) | None |
| 3E2G2 | 3E2 | IgG2b | Fba peptide SEQ ID NO: 29 | High (70-90%) | None |
| 6G9E11 | 6G9 | IgG2b | Fba peptide SEQ ID NO: 29 | High (80-100%) | None |
| 9C11F6 | 9C11 | IgG2b | Fba peptide SEQ ID NO: 29 | High (90-100%) | None |
| 7H5H6 | 7H5 | IgG2b | Fba peptide SEQ ID NO: 29 | High (80-100%) | None |

Additional data for universal peptide-specific mAbs. Passive protection against disseminated candidiasis caused by *C. albicans* was prevented by removal of the mAbs by absorption with *Candida* cells before transfer.

TABLE 15

Hybridoma clone and related protective peptide-specific mAbs

| Hybridomas | mAb | mAb isotype | peptide vaccine | Protection | Protection of adsorbed mAb |
|---|---|---|---|---|---|
| 2C9G3 | 2C9 | IgG2a | GPV-M2 universal SEQ ID NO: 2 | High (80-100%) | None |
| 5A9D1 | 5A9 | IgG3 | GPV-M2 universal SEQ ID NO: 2 | High (80-90%) | None |
| 5A11B1 | 5A1 | IgG3 | GPV-M2 universal SEQ ID NO: 2 | High (60-90%) | None |
| 6E3D9 | 6E3 | IgG1 | GPV-M1 universal SEQ ID NO: 1 | High (80-100%) | None |
| 1D4H5 | 1D5 | IgG1 | GPV-M1 universal SEQ ID NO: 1 | High (70-80%) | None |
| 7A3C4 | 7A3 | IgG1 | GPV-M1 universal SEQ ID NO: 1 | High (70-90%) | None |
| 10E7E2 | 10E7 | IgG1 | GPV-P3 universal SEQ ID NO: 16 | High (80-100%) | None |
| 1A11H8 | lA11 | IgG3 | GPV-P1 universal SEQ ID NO: 14 | High (60-90%) | None |
| 10B6H8 | 10B6 | IgG1 | GPV-P1 universal SEQ ID NO: 14 | High (80-100%) | None |
| 5G5G3 | 5C5 | IgG2a | GPV-P1 universal SEQ ID NO: 14 | High (80-100%) | None |

Example 11

Abstract

*Candida* species are a major cause of fungal infections, yet to date there are no vaccines against *Candida* or indeed any other fungal pathogen. Our knowledge of immunity to *Candida* has almost exclusively been obtained from studies on *Candida albicans*, the most common disease-causing species. However, non-*albicans Candida* (NAC) species also cause disease and their prevalence is increasing. Worryingly, antifungal drug resistance has been detected for all clinically relevant *Candida* species to some degree. Research into immunity to NAC species is still at an early stage due to the lacking of tractable animal models with which to study these important pathogens. This is partly because many NAC species are not usually pathogenic in mouse models of candidiasis. Therefore, developing a faithful murine model to understand immunity to NAC species is key for future studies in this area.

The purpose of this study was to 1, perform a simultaneous comparison of the relative pathogenicity of the five clinically relevant *Candida* species in both immunocompetent and immunocompromised mouse models in order to present an overall picture of species-related variations in virulence. 2, to establish neutropenic mouse models of disseminated candidiasis by several medically important NAC species. 3, to address the fundamental question as to whether the peptide vaccine(s) will protect neutropenic mice from disseminated candidiasis caused by medically important NAC species. As results, we have successfully established a NAC invasive infection model in immunosuppressed BALB/c mice induced by cyclophosphamide, including *C. tropicalis, C. glabrata, C. parapsilosis* and *C. krusei*. Together with *C. albicans*, these four NAC species cause more than 90% of invasive infections. The intravenous (IV) challenge mouse model has been used to compare the virulence of different *Candida* species. The survival study was performed by comparing mortality and degree of kidney infection. Importantly, we demonstrated the protective efficacy of two peptide vaccines, which protect mice against disseminated candidiasis caused by *C. albicans*, also protected neutropenic mice against other medical significant NAC species.

Vaccinated BALB/c Mice were rendered severely neutropenic (polymorphonuclear leukocyte count, <500/mm3) 3 days prior to the beginning of the challenge study (Day 0) with 200 mg/kg of bodyweight intraperitoneal (i.p.) cyclophosphamide (CY, Sigma).

Significant decreases in the numbers of total leukocytes and neutrophils were observed in the CY-treated mice compared with those in the control mice. The effects of CY treatment were monitored every 2-3 days during the entire experimental procedure. The total neutrophil counts were reduced (<500 cells/mm3) within 3 days of the first CY injection, and severe neutropenia was maintained until the termination of the experiments at day 50.

Effect of immunosuppression on kidney fungal burdens of immunosuppressed mice infected with *C. tropicalis* and *C. krusei*. Mice were inoculated with 2×108 CFU of *C. tropicalis* per mouse. Twenty-four hours before fungal inoculation, one group of mice was immunosuppressed with an intraperitoneal injection of 200 mg/kg of cyclosphamide (CY).

Statistically significant differences were seen between control (DPBS i.p.) and immunosuppressed animals (p<0.01). B. Mice were inoculated with 1×108 CFU of *C. Krusei* per animal. Twenty-four hours before fungal inoculation, one group of mice was immuno-suppressed with an intraperitoneal injection of 200 mg/kg of CY. Statistically significant differences were seen between normal control and immuno-suppressed animals (p<0.01). We have seen a similar effect of immunosuppression on kidney CFU with other NAC species.

Establish Neutropenic Mouse Models of NAC

Neutropenic murine models of disseminated infection by *C. tropicalis, C. glabrata, C. parapsilosis* and *C. Krusei* have been successfully established. To induce neutropenia, naïve mice received a 200 mg/kg dose of cyclophosphamide (CY) by i.p. on day −3. Prolonged neutropenia was maintained for 30-50 days by giving each animal a 150 mg/kg dose of CY by i.p. every 10 days after infection. On day 0, mice of different experimental groups (five mice per group) were intravenously infected with 5×107 viable *C. parapsilosis* ATCC MYA-4646 (A), 1×108 *C. glabrata* ATCC 2001 cells (B) and 2×108 *C. tropicalis* ATCC 28775 cells (C) or 1×108 *C. Krusei* ATCC 32196 in 0.1 ml DPBS (D). As controls, immunocompetent mice were challenged with the same dose of each *Candida* strain tested.

Double Peptide Vaccines Induced Solid Protection Against Disseminated Candidiasis in Mice.

A. P1 peptide was conjugated to the N terminus of P2 peptide through double lysine linker to form P1-P2 conjugate. Mice immunized with P1, P2 or P1 & P2 mixture were used as positive controls to compare the efficacy between single peptide vaccine and double peptide conjugate. After animals were challenged, P1-P2 conjugate induced 100% complete protection up to 60 days when the experiment was terminated. Our data indicate P1-P2 double peptide vaccine worked superior as compared to other individual peptides or peptide mixture.

B. By the same approach, double universal peptide 1 & 2 (UP1-UP2) conjugate was used to vaccinate mice and evaluated for its ability to induce protective immunity against disseminated candidiasis caused by medically important non-*albicans* species. Immunized mice challenged with *C. albicans* were used as positive controls, and mice that received DPBS and challenged with *C. albicans* were used as negative controls. Survival data show that universal double peptide conjugate vaccine induced protective immunity against all the medically important non-*albicans Candida* species, in addition to *C. albicans*.

Conclusions

Neutropenic murine models of disseminated infection by *C. tropicalis, C. glabrata, C. Krusei* and *C. parapsilosis* have been successfully established.

A double peptide conjugate vaccine, targeting two peptides expressed on the cell surface of all the medically important *Candida* species, can induce a high degree of protection against disseminated candidiasis in a mouse model of human disseminated candidiasis by *Candida* species.

Example 12 mAbs Protect Against *Candida auris*

Induction of Immunosuppression in Mice:

An immunocompromised murine model of disseminated infection by *C. auris* was developed. To induce immunosuppression, Jackson B6.129X1Elane mice received a 200 mg/kg dose of cyclophosphamide (CY) by i.p. on day −3. Prolonged immunosuppression was maintained for 30 days by giving each animal a 200 mg/kg dose of CY by i.p. every 10 days after infection. On day 0, mice of different experimental groups were intravenously infected with 2×108 viable *C. auris* yeast cells.

Passive Transfer of MAbs by Intraperitoneal (i.p.) Route:

The preventive effect of peptide-specific mAbs, for example 7H6A2 and 1D4H5, and combinations thereof, for example 7H6A2+1D4H5, was examined by passive transfer experiments. Each mAb was appropriately diluted in DPBS to give a 40,000-100,000 ELISA titer against each corresponding specific peptide coated on the plate. For testing, mice received 0.5 ml of each mAb or 1 ml of two mAbs in combination (0.5 ml of each) intraperitoneally. Control mice received 0.5 ml of the DPBS diluents.

Figure 14:
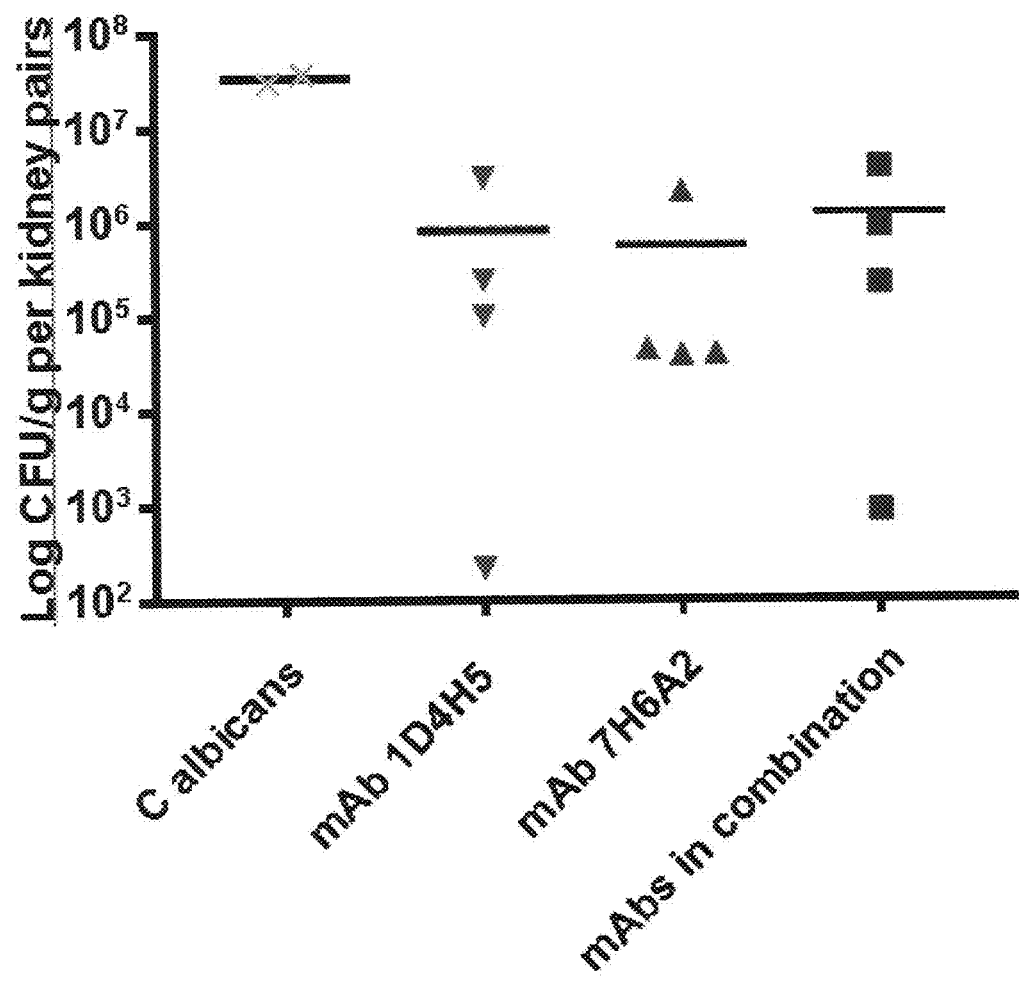
FIG. 14 shows protective mAbs protect immunocompromised mice against disseminated infection by *Candida auris*. Mice received either mAb 7H6A2 or 1D4H5 or the two mAbs in combination had reduced CFUs in kidneys (A) and in brains (B) as compared with control mice.

Protective mAbs protect immunocompromised mice against disseminated infection by *Candida auris*: The possibility of using passive mAb immunotherapy in immunocompromised mice against disseminated candidiasis by *C. auris*. The protective effect of mAb 7H6A2, 1D4H5 or these two mAbs in combination against the disease in immunocompromised mice was examined by passive transfer experiments (FIG. 14). Mice received either mAb 7H6A2 or 1D4H5 or the two mAbs in combination had reduced CFUs in kidneys (FIG. 14A) and in brains (FIG. 14B) as compared with control mice. Especially there is no CFU detected in brains of mice received mAb 7H6A2 treatment.

Example 13

In embodiments, protective mAbs have enhanced/synergy efficacy when combined with conventional antimicrobial drugs against fungal infections, such as disseminated candidiasis caused by *C. albicans* in mice.

TABLE 16

| Treatment | MST (mean survival times) Days |
| --- | --- |
| None | 9.4 ± 2.1 |
| Amp B (0.5 mg/kg) | 14.5 ± 3.7 |
| mAb E2-9 + Amp B (0.5 mg/kg) | 29.4 ± 4.2 |
| mAb M2-4 + Amp B (0.5 mg/kg) | 37.4 ± 6.3 |
| mAb 2D5 + Amp B (0.5 mg/kg) | 39.1 ± 5.9 |
| mAb 21310 + Amp B (0.5 mg/kg) | 46.7 ± 6.7 |

Table 16: mAbs have Enhanced/Synergy Efficacy when Combined with Conventional Antimicrobial Drugs Against Disseminated Candidiasis Therapeutic effect of amphotericin B (Amp B) on mice with disseminated candidiasis is dose-dependent. BALB/c mice received minimal dose of Amp B (0.5 mg drug/kg body) appeared to be the same susceptible to the disease as mice that received no Amp B. Combination treatment of Amp B (0.5 mg/kg body weight) and each mAb (E2-9, M2-4, 2D5F7 and 2B10) at 8 hours post-infection significantly increased the survival time of mice receive the Amp B and mAb treatment, as compared to mice that received none treatment or with Amp B only.

Materials and Methods

Amp B—Antibody Combination Therapy

Prior to testing the effects of combination therapy with combination of Amp B & mAbs, the dose of the Amp B alone (0.5 mg/kg) that have no therapeutic effect on animals with disseminated candidiasis was determined. Mice were then given by i.v. of 5×10e5 of *C. albicans* 3153A yeast cells, 8 hour later the mice received i.p. 0.5 mg Amp B/kg body weight with each mAb (E2-9, M2-4, 2D5F7 and 2B10C1). Mice without any treatment and mice treated with antifungal drug alone were used as controls. Survival curves were scored and MST were measured.

Example 14

TABLE 17

| SEQ ID | Identifier | Sequence |
| --- | --- | --- |
| 1 | GPV-M1 | FWVNPDCGLKTR |
| 2 | GPV-M2 | TTTIGSFPQTKDIR |
| 3 | GPV-M3 | ADKDSLDLEPISLLPK |
| 4 | GPV-M4 | YNLPLFPTTTIGSFPQTKDIR |
| 5 | GPV-M5 | DDVSGKIQALQLGLALR |
| 6 | GPV-M6 | GWPEVKESLTNMVEAAK |
| 7 | GPV-M7 | YTKFDLAPIDVLFAMGR |
| 8 | GPV-M8 | ASAVVQKAIEK |
| 9 | GPV-M9 | FWVNPRODCGLK |
| 10 | GPV-M10 | FWVNPRODCGLKTR |
| 11 | GPV-M11 | SESSITNDPKVQER |
| 12 | GPV-M12 | KFITDQTSIDLVADGR.T |
| 13 | GPV-M13 | KSTVASSDR |
| 14 | GPV-P1 | AILGGSKVSDKI |
| 15 | GPV-P2 | STGGGASLELLEGK |
| 16 | GPV-P3 | IVIIGGGDTATVAKK |
| 17 | GPV-P4 | ALENPROERPFLAILGGAKVSDK.I |
| 18 | GPV-P5 | KVKADPEAVKK |
| 19 | GPV-P6 | LLGQKVTFLNDCVGPEVTKAVENAK |
| 20 | GPV-P7 | LSVKDLDVAGKR |

TABLE 17-continued

| SEQ ID | Identifier | Sequence |
|---|---|---|
| 21 | GPV-P8 | MPIGDSLFDEAGAKNVEHLVEK |
| 22 | GPV-P9 | SAENGNIVIIGGGDTATVAKK |
| 23 | GPV-P10 | VTFLNDCVGPEVTK |
| 24 | GPV-P11 | NDKYSLAPVATELEK |
| 25 | GPV-P12 | YHIEEEGSSKDKDGK |
| 26 | Fba-C1 | IAEALDIFHTKGQL |
| 27 | Fba-C2 | EGADKPNKKYFDPRV |
| 28 | Fba-C3 | LKTIGGALQISDNSE |
| 29 | Fba | YGKDVKDLFDYAQE |
| 30 | Met6 | PRIGGQRELKKITE |
| 31 | Hwp1 | QGETEEALIQKRSY |
| 32 | Eno1 | DSRGNPTVEVDFTT |
| 33 | Gap1 | NRSPSTGEQKSSGI |
| 34 | Pgk1 | VPLDGKTITNNQRI |
| 35 | Fba 2 | FAIPAINVTSSSTV |
| 36 | Fba3/FbaU1 | FAIPAINVTSSSTVVAALE |
| 37 | Fba4 | SSSTVVAAL |
| 38 | Met6-2 | YDQVLDLSLLFNAIP |
| 39 | Fba Pep2 | Y GKDVKDLFDYAQE |
| 40 | Fba Pep3 | Y G KDVKDLFDYAQE |
| 41 | Fba Pep4 | YG K DVKDLFDYAQE |
| 42 | Fba Pep5 | YGKD V KDLFDYAQE |
| 43 | Fba Pep6 | YGKDV K DLFDYAQE |
| 44 | Fba Pep7 | YGKDVKD L FDYAQE |
| 45 | Fba Pep8 | YGKDVKDL F DYAQE |
| 46 | Fba Pep9 | YGKDVKDLFD Y AQE |
| 47 | Fba Pep10 | Y GKDVKD L FDYAQE |
| 48 | Fba Pep11 | YGKDCVKCDLFDYACIE |
| 49 | linker | KK |
| 50 | linker | GPSL |
| 51 | PADRE | AKFVAAWTLKAAA |
| 52 | ? | RGD |
| 53 | Fba | Accession No. AOW28947 (Protein Accession No. XP_722690) |
| 54 | Met6 | Accession No. AOW30921 (Protein Accession No. XP_718219 |
| 55 | Hwp1 | Accession No. ACN63125 |
| 56 | Eno1 | Accession No. AAA71939 |
| 57 | Gap1 | Accession No. AOW29704 |
| 58 | Pgk1 | Accession No. AAA66523 |

TABLE 17-continued

| SEQ ID | Identifier | Sequence |
|---|---|---|
| 59 | 2810C1 | heavy chain DNA |
| 60 | 2810C1 | heavy chain amino acid |
| 61 | 2810C1 | light chain DNA |
| 62 | 2810C1 | light chain amino acid |
| 63 | 1D4H5 | heavy chain DNA |
| 64 | 1D4H5 | heavy chain amino acid |
| 65 | 1D4H5 | light chain DNA |
| 66 | 1D4H5 | light chain amino acid |
| 67 | 2D5F7 | heavy chain DNA |
| 68 | 2D5F7 | heavy chain amino acid |
| 69 | 2D5F7 | light chain DNA |
| 70 | 2D5F7 | light chain amino acid |
| 71 | 10E7E2 | heavy chain DNA |
| 72 | 10E7E2 | heavy chain amino acid |
| 73 | 10E7E2 | light chain DNA |
| 74 | 10E7E2 | light chain amino acid |
| 75 | TT 830-844 | QYIKANSKFIGITE |
| 76 | linker | EAAAK |
| 77 | linker | GGGGS |
| 78 | TT 946-967 | FNNFTVSFWLRVPKVSASHLE |
| 79 | GPV-MO2 | NPDCGLKTR |
| 80 | FbaU2 | PAINVTSSSTVVAALEAA |
| 81 | GPV-MO1 | PTTTIGSFPQ |
| 82 | GPV-MO1A | NLPLFPTTTIGSFPQTK |
| 83 | | PADRE-GPV-M1-GPSL-GPV-P1 |
| 84 | | TT830-844-GPSL-GPV-M1-GPSL-GPV-P1 |
| 85 | | TT947-967-GPSL-GPV-M1-GPSL-GPV-P1 |
| 86 | | RGD-GPV-P3-KK-GPV-M2 |
| 87 | | RGD-GPV-P3-KK-GPV-M2-KLH |
| 88 | | TT830-844-KK-GPV-P3-KK-GPV-M2 |
| 89 | | TT947-967-KK-GPV-P3-KK-GPV-M1 |
| 90 | | RGD-TT830-844-KK-GPV-P3-KK-GPV-M1 |
| 91 | | RGD-TT947-967-KK-GPV-P3-KK-GPV-M1 |
| 92 | | PADRE-GPV-M2-KK-GPV-P1 |
| 93 | | RGD-PADRE-GPV-M2-KK-GPV-P3 |

Example 15

TABLE 18

Examples of hybridoma clones producing protective mAbs, which are specific for peptides derived from C. albicans cell wall protein and the isotype of each protective mAbs.
Hybridoma clone and related protective peptide-specific mAbs

| Hybridomas | mAb | mAb isotype | peptide vaccine | peptide Sequences |
|---|---|---|---|---|
| 2C9G3 | 2C9 | IgG2a | GPV-M2 universal | cTTTIGSFPQTKDIR |
| 5A9D1 | 5A9 | IgG3 | GPV-M2 universal | cTTTIGSFPQTKDIR |
| 5A11B1 | 5A1 | IgG3 | GPV-M2 universal | cTTTIGSFPQTKDIR |
| 10E7E2 | 10E7 | IgG1 | GPV-P3 universal | cIVIIGGGDTATVAKK |
| 2B10C1 | 2B10 | IgG1 | Met6 peptide | PRIGGQRELKKITEc |
| 7H6A2 | 7H6 | IgG2b | Met6 peptide | PRIGGQRELKKITEc |

TABLE 19

Examples of protective mAbs that have been tested in moust model (A/J strain) of disseminated candidiasis caused by C. auris.

| mAb | mAb isotype | against C. auris |
|---|---|---|
| 2C9 | IgG2a | High (80-100%) |
| 5A9 | IgG3 | High (80-90%) |
| 5A1 | IgG3 | High (60-90%) |
| 10E7 | IgG1 | High (80-100%) |
| 2B10 | IgG1 | High (60-90%) |
| 7H6 | IgG2b | High (80-100%) |

Example 16

As shown herein, a panel of mAbs protect against C. auris invasive infection in newly established A/J mouse model of human disseminated candidiasis, including 6H1G8, 9F2G5, 10E7E2 and 3H7E3.

Also, mAbs in combination (such as, 9F2G5+3H7E3) provided enhanced protection as compared to 9F2G5 or 3H7E3 alone, such as in protection against C. auris invasive infection in mice.

Further, mAb 9F2G5 provides improved immunoprotection against C. auris disseminated candidiasis in mouse model as compared to anti-C. auris drug Micafungin, which is currently used in clinics.

Still further, 9F2G5 combined with Micafungin enhanced therapeutic potential of Micafungain, reducing CFUs in targeted organs as compared to Micafungin alone therapeutic treatment.

Thus, mAb 9F2G5 by itself not only protects against severe C. auris infection more effective than antifungal drug, but also functions to enhance conventional antimicrobial therapy of Micafungin.

Introduction:

Disseminated candidiasis is a life-threatening disease and a leading cause of bloodstream infections afflicting immunocompromised and hospitalized patients in the United States. Despite the availability of antifungal therapy, crude mortality in the last decade has remained unacceptably high (50-80%). The infection is caused by multiple species of the fungal genus Candida with C. albicans being the most common, together with C. tropicalis and C. glabrata, caused >90% disseminated candidiasis in humans. Of particular concern, "superbug" C. auris is a multi-drug resistant, health care-associated fungal pathogen, and has recently emerged as the first fungal pathogen to cause a global public health threat. Since there is no approved antifungal vaccine and current treatments are inadequate, antifungal antibodies could provide long-awaited new therapies for use alone or in combination with other agents, such as antifungal agents.

Shown herein are prophylactic/therapeutic antibodies that protect against disseminated candidiasis caused by C. auris. First, we identify peptide-specific mAbs protect against C. auris invasive infection in mouse model of human disseminated candidiasis. Secondly, different mAb combinations were further tested to identify synergistic efficacy of mAb cocktail. Finally, the mAb that has synergy/enhanced efficacy when combined with conventional antimicrobial drugs against disseminated candidiasis was identified.

Supporting Data:

Evaluation and validation of a panel of peptide-specific monoclonal antibodies (mAbs) as a passive immunization strategy protect against invasive C. auris infection in established A/J mouse model of human disease.

The monoclonal antibodies used in this experiment were:
6H1G8 (IgG2b), α-Hwp1 (Hyphal wall protein)
3E2G2 (IgG2b), α-Fba (Fructose bisphosphate aldolase)
10E7E2 (IgG1), α-GPV-P3 (General peptide vaccine 3 from Phosphoglycerate kinase)
9F2G5 (IgG2a), α-Pgk1 (Phosphoglycerate kinase)
3H7E3 (IgG1), α-Met6 (Methyltetrahydropteroyltriglutamate)

Figure 15:
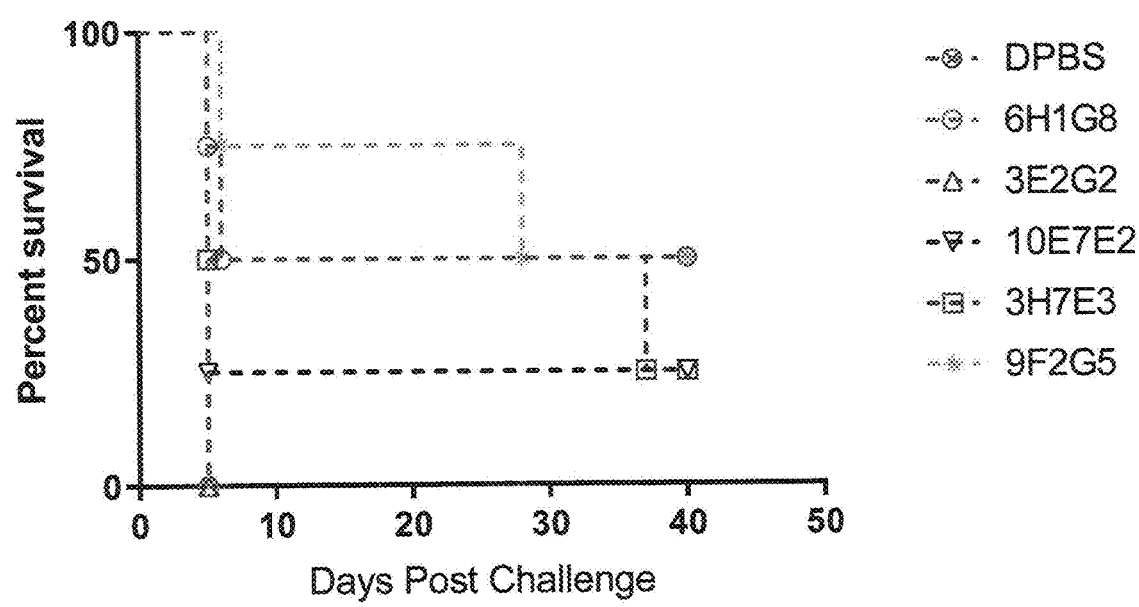
FIG. 15 shows monoclonal antibodies (mAbs) are effective against invasive candidiasis caused by *C. auris*, the multidrug-resistant *Candida* species. A. Complement protein C5-deficent A/J mice were treated with one of the five mAb or with DPBS as a vehicle control. The following day, mice were challenged with $1\times10^8$ *C. auris* cells/100 ul DPBS dose per mouse. Mice treated with mAbs 6H1G8 or 9F2G5 showed 50% survival by the termination of the experiment (40 days post challenge), whereas mice treated with 3H7E3 showed 50% survival up until 37 days post challenge. Groups treated with 10E7E2 or 3H7E3 showed 25% survival. B. Fungal burdens in the kidneys (top), heard (center), and brain (bottom). Non-detectible levels of fungal burden were achieved in the kidneys of one 6H1G8-treated mouse, whereas non-detectible levels of fungal burden were achieved in the heart and brain of several mice treated with 6H1G8, 9F2G5, or 3H7E3.

Referring to FIG. 15, for example, monoclonal antibodies (mAbs) are effective against invasive candidiasis caused by C. auris, the multidrug-resistant Candida species. For example, mAbs 6H1G8 and 9F2G5 provided best protection, evidenced by highest survival and lowest fungal burdens in targeted organs. mAbs 10E7E2 and 3H7E3 also provided some protection with 25% survival, and lower fungal loads in targeted organs.

Evaluation and Validation of Combination Therapy with mAb Cocktails in Established A/J Mouse Model of Disseminated Candidiasis.

Figure 16:
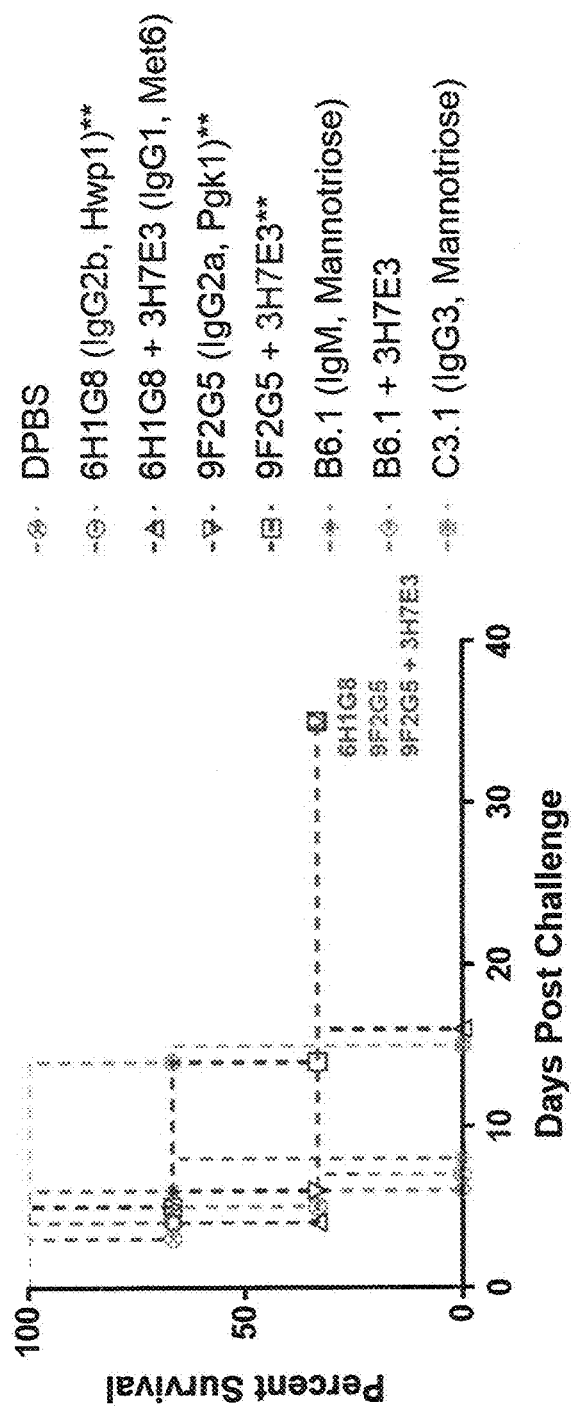
FIG. 16 shows two protective mAbs in combination conferred improved protection against systemic *C. auris* infection in passive transfer experiments. Identified protective mAbs were obtained by use of standard hybridoma technique and purified by use of protein A/G. A/J mice were given an i.p. dose of either single mAb or two mAbs in combination 24 hours before hematogensous challenge with a lethal dose (2×108) of *C. auris* AR-0386 live cells. Mice received either 9G2F5 alone or 6H1G8 alone or 9F2G5 and 3H7E3 in combination had 40% survival rate respectively, with prolonged survival as compared to control animals that received DPBS buffer control.

Referring to FIG. 16, for example, two protective mAbs in combination conferred best protection against systemic C. auris infection in passive transfer experiments. For example, two mAbs, such as 9F2G5+3H7E3 in combination, provided enhanced protection as compared to 9F2G5 or 3H7E3 alone. Mice that survived to Day 35 (6H1G8, 9F2G5, and 9F2G5+

3H7E3) had lowest fungal burdens in all organs. Consistent with previous data, 6H1G8 and 9F2G5 were able to almost clear fungal burden (only one mouse per groups 6H1G8, 9F2G5, and 9F2G5+3H7E3 had fungal burdens lower than DPBS).

Validation of antifungal therapy of mAb in combination with antifungal agents. Herein we validate that mAb 9F2G5 is able to enhance the effectiveness of currently available antifungal drugs against *C. auris*. As an example, we evaluate micafungin, which is an effective drug against different strains of *C. auris*, and fluconazole as negative control, to which most strains of *C. auris* (including our own) is resistant.

Figure 17:
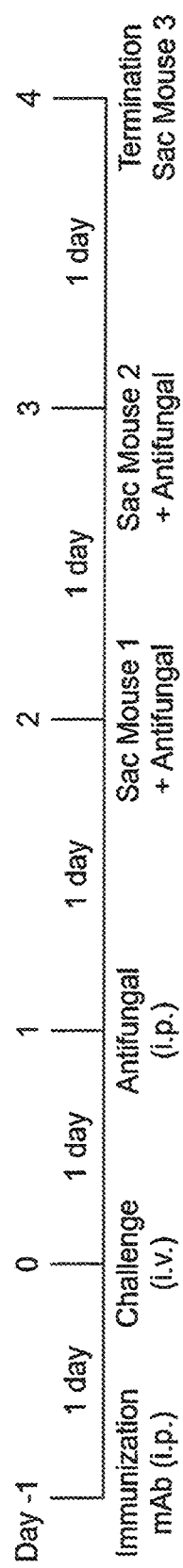
FIG. 17 shows experimental protocol.

Method and Material to determine if mAb 9F2G5 (α-Pgk1, IgG2a) can increase antifungal efficacy in A/J mice. See FIG. 17, for example.

Micafungin (Effective Drug) Fluconazole (Ineffective Drug)

Experimental Groups (Three Mice/Group):
1. DPBS
2. Micafungin (0.25 mg/kg/day)
3. Micafungin (0.5 mg/kg/day)
4. Micafungin (1.0 mg/kg/day)
5. 9F2G5
6. 9F2G5+Micafungin (0.25 mg/kg/day)
7. 9F2G5+Micafungin (0.5 mg/kg/day)
8. 9F2G5+Micafungin (1.0 mg/kg/day)
9. Fluconazole (25 mg/kg/day)
10. 9F2G5+Fluconazole (25 mg/kg/day)

Figure 18:
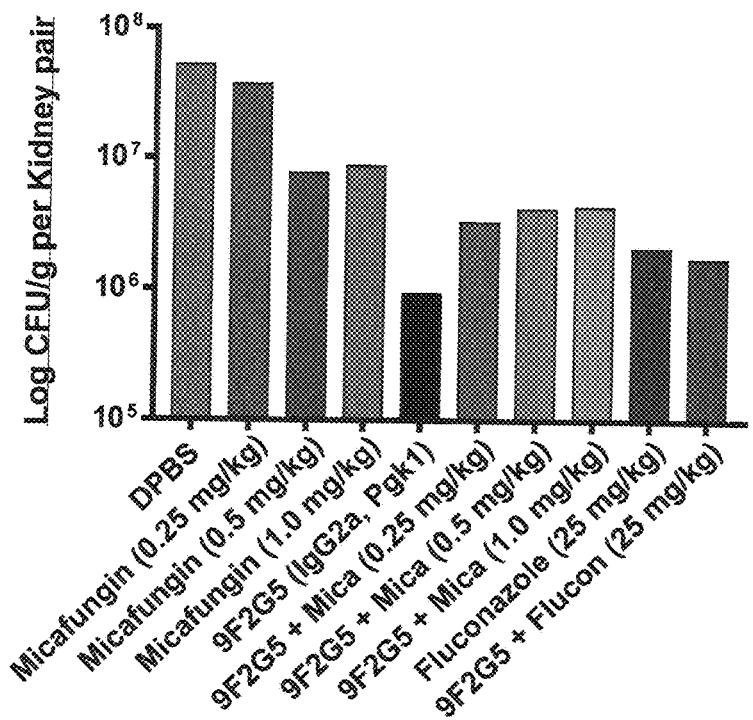
FIG. 18 shows mAb 9F2G5 used alone or with antifungal drug has therapeutic activity against *C. auris* disseminated candidiasis. Administration of 9F2G5 (α-Pgk1 peptide, IgG2a) alone provide better protection as compared to Micafungin alone therapeutic treatment, evidenced by reduced fungal burdens in both kidney (A) and heart (B) at day 4 post-infection. Antibody 9F2G5 given by i.p. 24 hours before challenge, combined with Micafungin given i.p. 24 h post-infection had enhanced therapeutic potential of Micafungin, reducing CFUs in both kidney (A) and heart (B) significantly as compared to Micafungin alone therapeutic treatment.
Figure 18:
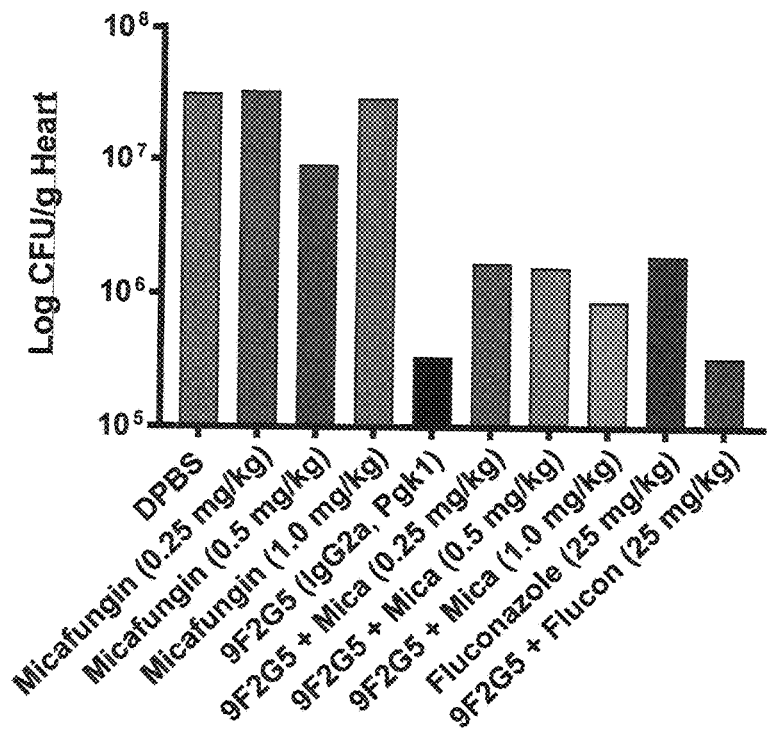

Referring to FIG. 18, mAb 9F2G5 used alone or with antifungal drug has therapeutic activity against *C. auris* disseminated candidiasis. Administration of 9F2G5 (α-Pgk1 peptide, IgG2a) alone provide better protection as compared to Micafungin alone therapeutic treatment, evidenced by reduced fungal burdens in both kidney (A) and heart (B) at day 4 post-infection. Antibody 9F2G5 given by i.p. 24 hours before challenge, combined with Micafungin given i.p. 24 h post-infection had enhanced therapeutic potential of Micafungin, reducing CFUs in both kidney (A) and heart (B) significantly as compared to Micafungin alone therapeutic treatment.

Thus, mAb can function as an adjunct to existing antifungal therapy. In our study, mAb 9F2G5 used alone provided better protection as compared to antifungal agent Micafungin. Furthermore, mAb 9F2G5, combined with Micafungin, also enhanced therapeutic potential of Micafungin, reducing fungal loads in targeted organs as compared to Micafungin alone.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. An immunogen consisting of an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, and SEQ ID NO: 28, wherein the immunogen is conjugated to at least one macromolecule.

2. The immunogen of claim 1, wherein the immunogen elicits an immune response in a mammal.

3. The immunogen of claim 1, wherein the immunogen is resistant to proteolytic cleavage.

4. A vaccine composition comprising the immunogen of claim 1 and a pharmaceutically acceptable carrier.

5. The immunogen of claim 1, wherein the immunogen is covalently linked to at least one additional immunogen by a linker.

6. The immunogen of claim 5, wherein the amino acid sequence of the at least one additional immunogen comprises a peptide that is at least 80% identical in two or more different microorganisms, and wherein the at least one additional immunogen comprises at least nine consecutive amino acid residues.

7. The immunogen of claim 5, wherein the at least one additional immunogen comprises at least one of fructose-bisphosphate aldolase (Fba), methyltetrahydropteroyltriglutamate homocysteine methyltransferase (Met6), hyphal wall protein-1 (Hwp1), enolase (Enol), glyceraldehyde-3-phosphate dehydrogenase (Gap1), and phosphoglycerate kinase (Pgk1).

8. The immunogen of claim 5, wherein the at least one additional immunogen consists of the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, or SEQ ID NO: 28, or any combination thereof.

9. The immunogen of claim 5, wherein the at least one additional immunogen consists of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, or SEQ ID NO: 48, or any combination thereof.

10. The immunogen of claim 5, wherein the linker comprises a peptide linker.

11. The immunogen of claim 10, wherein the peptide linker comprises the amino acid sequence KK (SEQ ID NO: 49), GPSL (SEQ ID NO: 50), PADRE (SEQ ID NO: 51).

12. The immunogen of claim 1, wherein the immunogen is a T-cell epitope.

13. The vaccine composition of claim 4, further comprising an adjuvant, a protein carrier, a T helper epitope, a Multiple Antigen Peptide (MAP), or any combination thereof.

14. The vaccine composition of claim 4, wherein the composition does not comprise an adjuvant.

15. The vaccine composition of claim 4, wherein the immunogen is not linked to a protein carrier.

16. The vaccine composition of claim 13 wherein the T helper epitope comprises the amino acid sequence PADRE (SEQ ID NO: 51) or RGD (SEQ ID NO: 52).

17. A method for active immunization against a microbial infection, the method comprising administering the immunogen of claim 1 to a subject in need thereof.

18. The immunogen of claim 1, wherein the at least one macromolecule is an adjuvant, a protein carrier, or both.

19. An immunogen consisting of an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 79, SEQ ID NO: 26, SEQ ID NO: 27, and SEQ ID NO: 28, wherein the immunogen is conjugated to at least one macromolecule, and wherein the immunogen is methylated, amidated, acetylated, PEGylated, or incorporates a cysteine residue.

20. The immunogen of claim 19, wherein the at least one macromolecule is an adjuvant, a protein carrier, or both.

\* \* \* \* \*

SEQUENCE LISTING

```
<160> NUMBER OF SEQ ID NOS: 97

<210> SEQ ID NO 1
<211> LENGTH: 13
<212> TYPE: PRT
<213> ORGANISM: Unknown
<220> FEATURE:
<223> OTHER INFORMATION: Description of Unknown: GPV-M1
      peptide
<220> FEATURE:
<221> NAME/KEY: MISC_FEATURE
<222> LOCATION: (1)..(1)
<223> OTHER INFORMATION: May or may not be present

<400> SEQUENCE: 1

Cys Phe Trp Val Asn Pro Asp Cys Gly Leu Lys Thr Arg
1               5                   10

<210> SEQ ID NO 2
<211> LENGTH: 15
<212> TYPE: PRT
<213> ORGANISM: Unknown
<220> FEATURE:
<223> OTHER INFORMATION: Description of Unknown: GPV-M2
      peptide
<220> FEATURE:
<221> NAME/KEY: MISC_FEATURE
<222> LOCATION: (1)..(1)
<223> OTHER INFORMATION: May or may not be present

<400> SEQUENCE: 2

Cys Thr Thr Thr Ile Gly Ser Phe Pro Gln Thr Lys Asp Ile Arg
1               5                   10                  15

<210> SEQ ID NO 3
<211> LENGTH: 16
<212> TYPE: PRT
```

```
<213> ORGANISM: Unknown
<220> FEATURE:
<223> OTHER INFORMATION: Description of Unknown: GPV-M3
      peptide

<400> SEQUENCE: 3

Ala Asp Lys Asp Ser Leu Asp Leu Glu Pro Ile Ser Leu Leu Pro Lys
1               5                   10                  15

<210> SEQ ID NO 4
<211> LENGTH: 21
<212> TYPE: PRT
<213> ORGANISM: Unknown
<220> FEATURE:
<223> OTHER INFORMATION: Description of Unknown: GPV-M4
      peptide

<400> SEQUENCE: 4

Tyr Asn Leu Pro Leu Phe Pro Thr Thr Thr Ile Gly Ser Phe Pro Gln
1               5                   10                  15

Thr Lys Asp Ile Arg
            20

<210> SEQ ID NO 5
<211> LENGTH: 17
<212> TYPE: PRT
<213> ORGANISM: Unknown
<220> FEATURE:
<223> OTHER INFORMATION: Description of Unknown: GPV-M5
      peptide

<400> SEQUENCE: 5

Asp Asp Val Ser Gly Lys Ile Gln Ala Leu Gln Leu Gly Leu Ala Leu
1               5                   10                  15

Arg

<210> SEQ ID NO 6
<211> LENGTH: 17
<212> TYPE: PRT
<213> ORGANISM: Unknown
<220> FEATURE:
<223> OTHER INFORMATION: Description of Unknown: GPV-M6
      peptide

<400> SEQUENCE: 6

Gly Trp Pro Glu Val Lys Glu Ser Leu Thr Asn Met Val Glu Ala Ala
1               5                   10                  15

Lys

<210> SEQ ID NO 7
<211> LENGTH: 17
<212> TYPE: PRT
<213> ORGANISM: Unknown
<220> FEATURE:
<223> OTHER INFORMATION: Description of Unknown: GPV-M7
      peptide

<400> SEQUENCE: 7

Tyr Thr Lys Phe Asp Leu Ala Pro Ile Asp Val Leu Phe Ala Met Gly
1               5                   10                  15

Arg

<210> SEQ ID NO 8
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

Ala Ser Ala Val Val Gln Lys Ala Ile Glu Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Trp Val Asn Pro Asp Cys Gly Leu Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Trp Val Asn Pro Asp Cys Gly Leu Lys Thr Arg
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Glu Ser Ser Ile Thr Asn Asp Pro Lys Val Gln Glu Arg
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Phe Ile Thr Asp Gln Thr Ser Ile Asp Leu Val Ala Asp Gly Arg
1               5                   10                  15

Thr

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Lys Ser Thr Val Ala Ser Ser Asp Arg
1               5

<210> SEQ ID NO 14
<211> LENGTH: 13
<212> TYPE: PRT
<213> ORGANISM: Unknown
<220> FEATURE:
<223> OTHER INFORMATION: Description of Unknown: GPV-P1
      peptide

<400> SEQUENCE: 14

Cys Ala Ile Leu Gly Gly Ser Lys Val Ser Asp Lys Ile
1               5                   10

<210> SEQ ID NO 15
<211> LENGTH: 14
<212> TYPE: PRT
<213> ORGANISM: Unknown
<220> FEATURE:
<223> OTHER INFORMATION: Description of Unknown: GPV-P2
      peptide

<400> SEQUENCE: 15

Ser Thr Gly Gly Gly Ala Ser Leu Glu Leu Leu Glu Gly Lys
1               5                   10

<210> SEQ ID NO 16
<211> LENGTH: 16
<212> TYPE: PRT
<213> ORGANISM: Unknown
<220> FEATURE:
<223> OTHER INFORMATION: Description of Unknown: GPV-P3
      peptide
<220> FEATURE:
<221> NAME/KEY: MISC_FEATURE
<222> LOCATION: (1)..(1)
<223> OTHER INFORMATION: May or may not be present

<400> SEQUENCE: 16

Cys Ile Val Ile Ile Gly Gly Gly Asp Thr Ala Thr Val Ala Lys Lys
1               5                   10                  15

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Leu Glu Asn Pro Glu Arg Pro Phe Leu Ala Ile Leu Gly Gly Ala
1               5                   10                  15

Lys Val Ser Asp Lys Ile
            20

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Val Lys Ala Asp Pro Glu Ala Val Lys Lys
1               5                   10
```

```
<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Leu Gly Gln Lys Val Thr Phe Leu Asn Asp Cys Val Gly Pro Glu
1               5                   10                  15

Val Thr Lys Ala Val Glu Asn Ala Lys
            20                  25

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Ser Val Lys Asp Leu Asp Val Ala Gly Lys Arg
1               5                   10

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Pro Ile Gly Asp Ser Leu Phe Asp Glu Ala Gly Ala Lys Asn Val
1               5                   10                  15

Glu His Leu Val Glu Lys
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ala Glu Asn Gly Asn Ile Val Ile Ile Gly Gly Gly Asp Thr Ala
1               5                   10                  15

Thr Val Ala Lys Lys
            20

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Thr Phe Leu Asn Asp Cys Val Gly Pro Glu Val Thr Lys
1               5                   10
```

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Asp Lys Tyr Ser Leu Ala Pro Val Ala Thr Glu Leu Glu Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr His Ile Glu Glu Glu Gly Ser Ser Lys Asp Lys Asp Gly Lys
1               5                   10                  15

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Ala Glu Ala Leu Asp Ile Phe His Thr Lys Gly Gln Leu
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Gly Ala Asp Lys Pro Asn Lys Lys Tyr Phe Asp Pro Arg Val
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Lys Thr Ile Gly Gly Ala Leu Gln Ile Ser Asp Asn Ser Glu
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MISC_FEATURE
<222> LOCATION: (15)..(15)
<223> OTHER INFORMATION: May or may not be present

<400> SEQUENCE: 29

Tyr Gly Lys Asp Val Lys Asp Leu Phe Asp Tyr Ala Gln Glu Cys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (15)..(15)
<223> OTHER INFORMATION: May or may not be present

<400> SEQUENCE: 30

Pro Arg Ile Gly Gly Gln Arg Glu Leu Lys Lys Ile Thr Glu Cys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (15)..(15)
<223> OTHER INFORMATION: May or may not be present

<400> SEQUENCE: 31

Gln Gly Glu Thr Glu Glu Ala Leu Ile Gln Lys Arg Ser Tyr Cys
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Ser Arg Gly Asn Pro Thr Val Glu Val Asp Phe Thr Thr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Arg Ser Pro Ser Thr Gly Glu Gln Lys Ser Ser Gly Ile
1               5                   10

<210> SEQ ID NO 34
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 34

Val Pro Leu Asp Gly Lys Thr Ile Thr Asn Asn Gln Arg Ile
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Ala Ile Pro Ala Ile Asn Val Thr Ser Ser Ser Thr Val
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Ala Ile Pro Ala Ile Asn Val Thr Ser Ser Ser Thr Val Val Ala
1               5                   10                  15

Ala Leu Glu

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ser Ser Thr Val Val Ala Ala Leu
1               5

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Tyr Asp Gln Val Leu Asp Leu Ser Leu Leu Phe Asn Ala Ile Pro
1               5                   10                  15

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Gly Lys Asp Val Lys Asp Leu Phe Asp Tyr Ala Gln Glu
```

```
1               5                   10
```

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Tyr Gly Lys Asp Val Lys Asp Leu Phe Asp Tyr Ala Gln Glu
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Tyr Gly Lys Asp Val Lys Asp Leu Phe Asp Tyr Ala Gln Glu
1               5                   10
```

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Tyr Gly Lys Asp Val Lys Asp Leu Phe Asp Tyr Ala Gln Glu
1               5                   10
```

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Tyr Gly Lys Asp Val Lys Asp Leu Phe Asp Tyr Ala Gln Glu
1               5                   10
```

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Tyr Gly Lys Asp Val Lys Asp Leu Phe Asp Tyr Ala Gln Glu
1               5                   10
```

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Tyr Gly Lys Asp Val Lys Asp Leu Phe Asp Tyr Ala Gln Glu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Gly Lys Asp Val Lys Asp Leu Phe Asp Tyr Ala Gln Glu
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Tyr Gly Lys Asp Val Lys Asp Leu Phe Asp Tyr Ala Gln Glu
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Gly Lys Asp Cys Val Lys Cys Asp Leu Phe Asp Tyr Ala Gln Glu
1               5                   10                  15

<210> SEQ ID NO 49
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Lys
1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Pro Ser Leu
1

<210> SEQ ID NO 51

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Lys Phe Val Ala Ala Trp Thr Leu Lys Ala Ala Ala
1               5                   10

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Gly Asp
1

<210> SEQ ID NO 53
<211> LENGTH: 359
<212> TYPE: PRT
<213> ORGANISM: Candida albicans

<400> SEQUENCE: 53

Met Ala Pro Pro Ala Val Leu Ser Lys Ser Gly Val Ile Tyr Gly Lys
1               5                   10                  15

Asp Val Lys Asp Leu Phe Asp Tyr Ala Gln Glu Lys Gly Phe Ala Ile
                20                  25                  30

Pro Ala Ile Asn Val Thr Ser Ser Thr Val Val Ala Ala Leu Glu
            35                  40                  45

Ala Ala Arg Asp Asn Lys Ala Pro Ile Ile Leu Gln Thr Ser Gln Gly
    50                  55                  60

Gly Ala Ala Tyr Phe Ala Gly Lys Gly Val Asp Asn Lys Asp Gln Ala
65                  70                  75                  80

Ala Ser Ile Ala Gly Ser Ile Ala Ala His Tyr Ile Arg Ala Ile
                85                  90                  95

Ala Pro Thr Tyr Gly Ile Pro Val Val Leu His Thr Asp His Cys Ala
            100                 105                 110

Lys Lys Leu Leu Pro Trp Phe Asp Gly Met Leu Lys Ala Asp Glu Glu
        115                 120                 125

Phe Phe Ala Lys Thr Gly Thr Pro Leu Phe Ser Ser His Met Leu Asp
130                 135                 140

Leu Ser Glu Glu Thr Asp Asp Glu Asn Ile Ala Thr Cys Ala Lys Tyr
145                 150                 155                 160

Phe Glu Arg Met Ala Lys Met Gly Gln Trp Leu Glu Met Glu Ile Gly
                165                 170                 175

Ile Thr Gly Gly Glu Glu Asp Gly Val Asn Asn Glu His Val Glu Lys
            180                 185                 190

Asp Ala Leu Tyr Thr Ser Pro Glu Thr Val Phe Ala Val Tyr Glu Ser
        195                 200                 205

Leu His Lys Ile Ser Pro Asn Phe Ser Ile Ala Ala Phe Gly Asn
    210                 215                 220

Val His Gly Val Tyr Lys Pro Gly Asn Val Gln Leu Arg Pro Glu Ile
225                 230                 235                 240
```

```
Leu Gly Asp His Gln Val Tyr Ala Lys Lys Gln Ile Gly Thr Asp Ala
            245                 250                 255

Lys His Pro Leu Tyr Leu Val Phe His Gly Gly Ser Gly Ser Thr Gln
            260                 265                 270

Glu Glu Phe Asn Thr Ala Ile Lys Asn Gly Val Val Lys Val Asn Leu
            275                 280                 285

Asp Thr Asp Cys Gln Tyr Ala Tyr Leu Thr Gly Ile Arg Asp Tyr Val
            290                 295                 300

Thr Asn Lys Ile Glu Tyr Leu Lys Ala Pro Val Gly Asn Pro Glu Gly
305                 310                 315                 320

Ala Asp Lys Pro Asn Lys Lys Tyr Phe Asp Pro Arg Val Trp Val Arg
            325                 330                 335

Glu Gly Glu Lys Thr Met Ser Lys Arg Ile Ala Glu Ala Leu Asp Ile
            340                 345                 350

Phe His Thr Lys Gly Gln Leu
            355

<210> SEQ ID NO 54
<211> LENGTH: 767
<212> TYPE: PRT
<213> ORGANISM: Candida albicans

<400> SEQUENCE: 54

Met Val Gln Ser Ser Val Leu Gly Phe Pro Arg Ile Gly Gly Gln Arg
1               5                   10                  15

Glu Leu Lys Lys Ile Thr Glu Ala Tyr Trp Ser Gly Lys Ala Thr Val
            20                  25                  30

Glu Glu Leu Leu Ala Lys Gly Lys Glu Leu Arg Glu His Asn Trp Lys
            35                  40                  45

Leu Gln Gln Lys Ala Gly Val Asp Ile Ile Pro Ser Asn Asp Phe Ser
            50                  55                  60

Tyr Tyr Asp Gln Val Leu Asp Leu Ser Leu Leu Phe Asn Ala Ile Pro
65                  70                  75                  80

Glu Arg Tyr Thr Lys Phe Asp Leu Ala Pro Ile Asp Val Leu Phe Ala
            85                  90                  95

Met Gly Arg Gly Leu Gln Lys Lys Ala Thr Glu Thr Gln Ala Ala Val
            100                 105                 110

Asp Val Thr Ala Leu Glu Met Val Lys Trp Phe Asp Ser Asn Tyr His
            115                 120                 125

Tyr Val Arg Pro Thr Phe Ser His Ser Thr Glu Phe Lys Leu Asn Thr
            130                 135                 140

Ala Ala Gly Ile Lys Pro Val Asp Glu Phe Asn Glu Ala Lys Ala Leu
145                 150                 155                 160

Gly Val Gln Thr Arg Pro Val Ile Leu Gly Pro Val Ser Tyr Leu Tyr
            165                 170                 175

Leu Gly Lys Ala Asp Lys Asp Ser Leu Asp Leu Glu Pro Ile Ser Leu
            180                 185                 190

Leu Pro Lys Ile Leu Pro Val Tyr Lys Glu Leu Leu Gln Lys Leu Lys
            195                 200                 205

Glu Ala Gly Ala Glu Gln Val Gln Ile Asp Glu Pro Val Leu Val Leu
            210                 215                 220

Asp Leu Pro Glu Ala Val Gln Ser Lys Phe Lys Glu Ala Tyr Asp Ala
225                 230                 235                 240

Leu Val Gly Ala Asp Val Pro Glu Leu Ile Leu Thr Thr Tyr Phe Gly
            245                 250                 255
```

```
Asp Val Arg Pro Asn Leu Lys Ala Ile Glu Asn Leu Pro Val Ala Gly
            260                 265                 270

Phe His Phe Asp Phe Val Arg Val Pro Glu Gln Leu Asp Glu Val Ala
            275                 280                 285

Ser Ile Leu Lys Asp Gly Gln Thr Leu Ser Ala Gly Val Val Asp Gly
            290                 295                 300

Arg Asn Ile Trp Lys Thr Asp Phe Ala Lys Ala Ser Ala Val Val Gln
305                 310                 315                 320

Lys Ala Ile Glu Lys Val Gly Lys Asp Lys Val Val Ala Thr Ser
                325                 330                 335

Ser Ser Leu Leu His Thr Pro Val Asp Leu Glu Ser Glu Thr Lys Leu
            340                 345                 350

Asp Ala Val Ile Lys Asp Trp Phe Ser Phe Ala Thr Gln Lys Leu Asp
            355                 360                 365

Glu Val Val Val Ile Ala Lys Asn Val Ser Gly Glu Asp Val Ser Lys
            370                 375                 380

Gln Leu Glu Ala Asn Ala Ala Ser Ile Lys Ala Arg Ser Glu Ser Ser
385                 390                 395                 400

Ile Thr Asn Asp Pro Lys Val Gln Glu Arg Leu Thr Thr Ile Asn Glu
                405                 410                 415

Ala Leu Ala Thr Arg Lys Ala Ala Phe Pro Glu Arg Leu Thr Glu Gln
            420                 425                 430

Lys Ala Lys Tyr Asn Leu Pro Leu Phe Pro Thr Thr Thr Ile Gly Ser
            435                 440                 445

Phe Pro Gln Thr Lys Asp Ile Arg Ile Asn Arg Asn Lys Phe Ala Lys
            450                 455                 460

Gly Gln Ile Thr Ala Glu Glu Tyr Glu Ala Phe Ile Asn Lys Glu Ile
465                 470                 475                 480

Glu Thr Val Val Arg Phe Gln Glu Glu Ile Gly Leu Asp Val Leu Val
                485                 490                 495

His Gly Glu Pro Glu Arg Asn Asp Met Val Gln Tyr Phe Gly Glu Gln
            500                 505                 510

Leu Asn Gly Phe Ala Phe Thr Thr Asn Gly Trp Val Gln Ser Tyr Gly
            515                 520                 525

Ser Arg Tyr Val Arg Pro Pro Ile Ile Val Gly Asp Val Ser Arg Pro
530                 535                 540

Lys Ala Met Thr Val Lys Glu Ser Val Tyr Ala Gln Ser Ile Thr Ser
545                 550                 555                 560

Lys Pro Met Lys Gly Met Leu Thr Gly Pro Val Thr Ile Leu Arg Trp
                565                 570                 575

Ser Phe Pro Arg Asp Asp Val Ser Gly Lys Ile Gln Ala Leu Gln Leu
            580                 585                 590

Gly Leu Ala Leu Arg Asp Glu Val Asn Asp Leu Glu Gly Ala Gly Ile
            595                 600                 605

Thr Val Ile Gln Val Asp Glu Pro Ala Ile Arg Glu Gly Leu Pro Leu
            610                 615                 620

Arg Ala Gly Lys Glu Arg Ser Asp Tyr Leu Asn Trp Ala Ala Gln Ser
625                 630                 635                 640

Phe Arg Val Ala Thr Ser Gly Val Glu Asn Ser Thr Gln Ile His Ser
                645                 650                 655

His Phe Cys Tyr Ser Asp Leu Asp Pro Asn His Ile Lys Ala Leu Asp
            660                 665                 670
```

```
Ala Asp Val Val Ser Ile Glu Phe Ser Lys Lys Asp Pro Asn Tyr
            675                 680                 685

Ile Gln Glu Phe Ser Glu Tyr Pro Asn His Ile Gly Leu Gly Leu Phe
    690                 695                 700

Asp Ile His Ser Pro Arg Ile Pro Ser Lys Gln Glu Phe Val Ser Arg
705                 710                 715                 720

Ile Glu Glu Ile Leu Lys Val Tyr Pro Ala Ser Lys Phe Trp Val Asn
                725                 730                 735

Pro Asp Cys Gly Leu Lys Thr Arg Gly Trp Pro Glu Val Lys Glu Ser
                740                 745                 750

Leu Thr Asn Met Val Glu Ala Ala Lys Glu Phe Arg Ala Lys Tyr
            755                 760                 765

<210> SEQ ID NO 55
<211> LENGTH: 264
<212> TYPE: PRT
<213> ORGANISM: Candida albicans

<400> SEQUENCE: 55

Ser Ser Ser Ala Pro Ala Thr Thr Pro Asn Thr Ser Val Pro Thr Thr
1               5                   10                  15

Thr Thr Glu Thr Lys Ser Ser Ser Thr Pro Leu Thr Thr Thr Thr Glu
            20                  25                  30

His Asp Thr Thr Val Val Thr Val Thr Ser Cys Ser Asn Ser Val Cys
        35                  40                  45

Thr Glu Ser Glu Val Thr Thr Gly Val Ile Val Ile Thr Ser Lys Asp
    50                  55                  60

Thr Ile Tyr Thr Thr Tyr Cys Pro Leu Thr Glu Thr Thr Pro Val Ser
65                  70                  75                  80

Thr Ala Pro Ala Thr Glu Thr Pro Thr Gly Thr Val Ser Thr Ser Thr
                85                  90                  95

Glu Gln Ser Thr Thr Val Ile Thr Val Thr Ser Cys Ser Glu Ser Ser
            100                 105                 110

Cys Thr Glu Ser Glu Val Thr Thr Gly Val Val Val Thr Ser Glu
            115                 120                 125

Glu Thr Val Tyr Thr Thr Phe Cys Pro Leu Thr Glu Asn Thr Pro Gly
    130                 135                 140

Thr Asp Ser Thr Pro Glu Ala Ser Ile Pro Pro Met Glu Thr Ile Pro
145                 150                 155                 160

Ala Gly Ser Gln Pro Ser Ile Pro Ala Gly Glu Thr Ser Pro Ala Val
                165                 170                 175

Pro Lys Ser Asp Val Pro Ala Thr Glu Ser Ala Pro Ala Pro Glu Met
            180                 185                 190

Thr Pro Ala Gly Thr Glu Thr Lys Pro Ala Ala Pro Lys Ser Ser Ala
        195                 200                 205

Pro Ala Thr Glu Pro Ser Pro Val Ala Pro Gly Thr Glu Ser Ala Pro
    210                 215                 220

Ala Gly Pro Gly Ala Ser Ser Pro Lys Ser Ser Val Leu Ala Ser
225                 230                 235                 240

Glu Thr Ser Pro Ile Ala Pro Gly Ala Glu Thr Ala Pro Ala Gly Ser
                245                 250                 255

Ser Gly Ala Ile Thr Ile Pro Glu
            260

<210> SEQ ID NO 56
```

```
<211> LENGTH: 440
<212> TYPE: PRT
<213> ORGANISM: Candida albicans

<400> SEQUENCE: 56
```

| | | | | | | | | | | | | | | | |
|---|---|---|---|---|---|---|---|---|---|---|---|---|---|---|---|
| Met | Ser | Tyr | Ala | Thr | Lys | Ile | His | Ala | Arg | Tyr | Val | Tyr | Asp | Ser | Arg |
| 1 | | | | 5 | | | | | 10 | | | | | 15 | |
| Gly | Asn | Pro | Thr | Val | Glu | Val | Asp | Phe | Thr | Thr | Asp | Lys | Gly | Leu | Phe |
| | | | 20 | | | | | 25 | | | | | 30 | | |
| Arg | Ser | Ile | Val | Pro | Ser | Gly | Ala | Ser | Thr | Gly | Val | His | Glu | Ala | Leu |
| | | 35 | | | | | 40 | | | | | 45 | | | |
| Glu | Leu | Arg | Asp | Gly | Asp | Lys | Ser | Lys | Trp | Leu | Gly | Lys | Gly | Val | Leu |
| | 50 | | | | | 55 | | | | | 60 | | | | |
| Lys | Ala | Val | Ala | Asn | Val | Asn | Asp | Ile | Ile | Ala | Pro | Ala | Leu | Ile | Lys |
| 65 | | | | | 70 | | | | | 75 | | | | | 80 |
| Ala | Lys | Ile | Asp | Val | Val | Asp | Gln | Ala | Lys | Ile | Asp | Glu | Phe | Leu | Leu |
| | | | | 85 | | | | | 90 | | | | | 95 | |
| Ser | Leu | Asp | Gly | Thr | Pro | Asn | Lys | Ser | Lys | Leu | Gly | Ala | Asn | Ala | Ile |
| | | | | 100 | | | | | 105 | | | | | 110 | |
| Leu | Gly | Val | Ser | Leu | Ala | Ala | Ala | Asn | Ala | Ala | Ala | Ala | Gln | Gly | |
| | | | 115 | | | | | 120 | | | | | 125 | | |
| Ile | Pro | Leu | Tyr | Lys | His | Ile | Ala | Asn | Ile | Ser | Asn | Ala | Lys | Lys | Gly |
| | | | 130 | | | | | 135 | | | | | 140 | | |
| Lys | Phe | Val | Leu | Pro | Val | Pro | Phe | Gln | Asn | Val | Leu | Asn | Gly | Gly | Ser |
| 145 | | | | | 150 | | | | | 155 | | | | | 160 |
| His | Ala | Gly | Gly | Ala | Leu | Ala | Phe | Gln | Glu | Phe | Met | Ile | Ala | Pro | Thr |
| | | | | 165 | | | | | 170 | | | | | 175 | |
| Gly | Val | Ser | Thr | Phe | Ser | Glu | Ala | Leu | Arg | Ile | Gly | Ser | Glu | Val | Tyr |
| | | | 180 | | | | | 185 | | | | | 190 | | |
| His | Asn | Leu | Lys | Ser | Leu | Thr | Lys | Lys | Tyr | Gly | Gln | Ser | Ala | Gly | |
| | | | 195 | | | | | 200 | | | | | 205 | | |
| Asn | Val | Gly | Asp | Glu | Gly | Gly | Val | Ala | Pro | Asp | Ile | Lys | Thr | Pro | Lys |
| | | 210 | | | | | 215 | | | | | 220 | | | |
| Glu | Ala | Leu | Asp | Leu | Ile | Met | Asp | Ala | Ile | Asp | Lys | Ala | Gly | Tyr | Lys |
| 225 | | | | | 230 | | | | | 235 | | | | | 240 |
| Gly | Lys | Val | Gly | Ile | Ala | Met | Asp | Val | Ala | Ser | Ser | Glu | Phe | Tyr | Lys |
| | | | | 245 | | | | | 250 | | | | | 255 | |
| Asp | Gly | Lys | Tyr | Asp | Leu | Asp | Phe | Lys | Asn | Pro | Glu | Ser | Asp | Pro | Ser |
| | | | 260 | | | | | 265 | | | | | 270 | | |
| Lys | Trp | Leu | Ser | Gly | Pro | Gln | Leu | Ala | Asp | Leu | Tyr | Glu | Gln | Leu | Ile |
| | | 275 | | | | | 280 | | | | | 285 | | | |
| Ser | Glu | Tyr | Pro | Ile | Val | Ser | Ile | Glu | Asp | Pro | Phe | Ala | Glu | Asp | Asp |
| | 290 | | | | | 295 | | | | | 300 | | | | |
| Trp | Asp | Ala | Trp | Val | His | Phe | Phe | Glu | Arg | Val | Gly | Asp | Lys | Ile | Gln |
| 305 | | | | | 310 | | | | | 315 | | | | | 320 |
| Ile | Val | Gly | Asp | Asp | Leu | Thr | Val | Thr | Asn | Pro | Thr | Arg | Ile | Lys | Thr |
| | | | | 325 | | | | | 330 | | | | | 335 | |
| Ala | Ile | Glu | Lys | Lys | Ala | Ala | Asn | Ala | Leu | Leu | Leu | Lys | Val | Asn | Gln |
| | | | 340 | | | | | 345 | | | | | 350 | | |
| Ile | Gly | Thr | Leu | Thr | Glu | Ser | Ile | Gln | Ala | Ala | Asn | Asp | Ser | Tyr | Ala |
| | | | 355 | | | | | 360 | | | | | 365 | | |
| Ala | Gly | Trp | Gly | Val | Met | Val | Ser | His | Arg | Ser | Gly | Glu | Thr | Glu | Asp |
| | | 370 | | | | | 375 | | | | | 380 | | | |
| Thr | Phe | Ile | Ala | Asp | Leu | Ser | Val | Gly | Leu | Arg | Ser | Gly | Gln | Ile | Lys |

```
                385                 390                 395                 400
Thr Gly Ala Pro Ala Arg Ser Glu Arg Leu Ala Lys Leu Asn Gln Ile
                    405                 410                 415

Leu Arg Ile Glu Glu Leu Gly Ser Glu Ala Ile Tyr Ala Gly Lys
            420                 425                 430

Asp Phe Gln Lys Ala Ser Gln Leu
            435                 440

<210> SEQ ID NO 57
<211> LENGTH: 582
<212> TYPE: PRT
<213> ORGANISM: Candida albicans

<400> SEQUENCE: 57

Met Leu His Lys Lys Glu Thr Asn Asp Thr Phe Val Gln Leu Asn Arg
1               5                   10                  15

Ser Pro Ser Thr Gly Glu Gln Lys Ser Gly Ile Trp Ser Ser Ile
            20                  25                  30

Lys Asp Ser Phe Lys Pro Ala Leu Pro Gln Asp Lys Leu Thr Gly Val
            35                  40                  45

Asp Asp Ile Pro Asp Arg Glu Leu Thr Asp Ile Glu Arg Ile Asn Ile
50                  55                  60

Asn Ala Ala Asn Ser Asn Leu Gln Arg Lys Leu Lys Thr Arg His Leu
65                  70                  75                  80

Gln Met Ile Ala Ile Gly Ser Ser Ile Gly Thr Gly Leu Phe Val Gly
                85                  90                  95

Thr Gly Gly Ala Leu Ser Thr Gly Gly Pro Ala Ala Ile Val Leu Ala
                100                 105                 110

Trp Ala Ile Ser Ala Ile Ser Val Phe Met Thr Met Gln Gly Leu Gly
            115                 120                 125

Glu Leu Ala Val Ala Phe Pro Val Ser Gly Gly Phe Asn Leu Tyr Ala
130                 135                 140

Ser Lys Phe Leu Glu Pro Gly Ile Gly Phe Ala Val Gly Trp Asn Tyr
145                 150                 155                 160

Phe Leu Gln Phe Phe Val Leu Leu Pro Leu Glu Leu Val Ala Gly Ala
                165                 170                 175

Ile Thr Ile Lys Tyr Trp Asn Ala Ser Ile Asn Ser Asp Val Phe Val
            180                 185                 190

Ile Ile Phe Trp Phe Val Val Leu Val Ile Thr Met Leu Gly Val Arg
            195                 200                 205

Trp Tyr Gly Glu Ala Glu Leu Val Phe Cys Thr Ile Lys Val Ile Ala
            210                 215                 220

Val Ile Gly Phe Ile Ile Leu Gly Ile Val Leu Ile Cys Gly Gly
225                 230                 235                 240

Pro Asn His Glu Phe Ile Gly Gly Lys Tyr Trp Arg Glu Pro Gly Pro
                245                 250                 255

Phe Ala Asn Ser Phe Lys Gly Phe Ala Ser Ser Leu Ile Thr Ala Ala
            260                 265                 270

Phe Ser Phe Gly Gly Thr Glu Met Ile Ala Leu Thr Ala Ser Glu Ser
            275                 280                 285

Ser Asn Val Arg His Ala Leu Pro Lys Ala Ile Lys Gln Val Phe Trp
            290                 295                 300

Arg Ile Val Ile Phe Tyr Leu Gly Ser Ile Ile Met Ile Ala Thr Leu
305                 310                 315                 320
```

```
Val Pro Tyr Asn Asp Lys Arg Leu Leu Gly Ser Ser Val Asp Val
            325                 330                 335

Thr Ala Ser Pro Phe Thr Ile Ala Ile Val Asn Gly Gly Ile Lys Gly
        340                 345                 350

Leu Pro Ser Val Ile Asn Ala Val Ile Leu Ile Ser Val Leu Ser Val
            355                 360                 365

Gly Asn Ala Ser Val Tyr Ala Thr Ser Arg Thr Leu Asn Ser Leu Ala
        370                 375                 380

Glu Gln Gly Met Ala Pro Lys Trp Thr Gly Tyr Ile Asp Arg Ala Gly
385                 390                 395                 400

Arg Pro Leu Phe Ala Ile Leu Ile Thr Asn Val Phe Gly Leu Phe Ala
                405                 410                 415

Leu Ile Ala Ala Asp Asn Glu Lys Gln Val Val Ala Phe Asn Trp Leu
            420                 425                 430

Leu Ala Leu Ser Gly Leu Ser Ser Ile Phe Thr Trp Met Ser Ile Asn
        435                 440                 445

Leu Ser His Ile Arg Phe Arg Arg Ala Met Lys Val Gln Asn Arg Ser
    450                 455                 460

Leu Thr Glu Leu Pro Phe Val Ala Gln Ser Gly Val Trp Gly Ser Tyr
465                 470                 475                 480

Phe Gly Leu Thr Leu Asn Ile Leu Tyr Leu Ile Ala Gln Phe Tyr Ile
                485                 490                 495

Gly Leu Phe Pro Val Gly Gly Lys Pro Asn Ala Tyr Asp Phe Phe Leu
            500                 505                 510

Ala Tyr Leu Gly Val Pro Val Ile Leu Ala Ser Trp Ile Gly Tyr Lys
        515                 520                 525

Ile Trp Lys Arg Asp Trp Thr Leu Phe Ile Arg Ala Lys Asp Ile Asp
    530                 535                 540

Leu Asp Thr Gly Arg Ile Asn Val Asp Leu Asp Leu Leu Gln Gln Glu
545                 550                 555                 560

Ile Ala Glu Glu Lys Ala Gln Leu Ala Glu Lys Pro Phe Tyr Ile Arg
                565                 570                 575

Ile Tyr Arg Phe Trp Cys
            580

<210> SEQ ID NO 58
<211> LENGTH: 417
<212> TYPE: PRT
<213> ORGANISM: Candida albicans

<400> SEQUENCE: 58

Met Ser Leu Ser Asn Lys Leu Ser Val Lys Asp Leu Asp Val Ala Gly
1               5                   10                  15

Lys Arg Val Phe Ile Arg Val Asp Phe Asn Val Pro Leu Asp Gly Lys
                20                  25                  30

Thr Ile Thr Asn Asn Gln Arg Ile Val Ala Ala Leu Pro Thr Ile Lys
            35                  40                  45

Tyr Val Glu Glu His Lys Pro Lys Tyr Ile Val Leu Ala Ser His Leu
        50                  55                  60

Gly Arg Pro Asn Gly Glu Arg Asn Asp Lys Tyr Ser Leu Ala Pro Val
65                  70                  75                  80

Ala Thr Glu Leu Glu Lys Leu Leu Gly Gln Lys Val Thr Phe Leu Asn
                85                  90                  95

Asp Cys Val Gly Pro Glu Val Thr Lys Ala Val Glu Asn Ala Lys Asp
            100                 105                 110
```

Gly Glu Ile Phe Leu Glu Asn Leu Arg Tyr His Ile Glu Glu Glu
            115                 120                 125

Gly Ser Ser Lys Asp Lys Asp Gly Lys Lys Val Lys Ala Asp Pro Glu
    130                 135                 140

Ala Val Lys Lys Phe Arg Gln Glu Leu Thr Ser Leu Ala Asp Val Tyr
145                 150                 155                 160

Ile Asn Asp Ala Phe Gly Thr Ala His Arg Ala His Ser Ser Met Val
                165                 170                 175

Gly Leu Glu Val Pro Gln Arg Ala Ala Gly Phe Leu Met Ser Lys Glu
            180                 185                 190

Leu Glu Tyr Phe Ala Lys Ala Leu Glu Asn Pro Glu Arg Pro Phe Leu
        195                 200                 205

Ala Ile Leu Gly Gly Ala Lys Val Ser Asp Lys Ile Gln Leu Ile Asp
    210                 215                 220

Asn Leu Leu Asp Lys Val Asp Met Leu Ile Val Gly Gly Gly Met Ala
225                 230                 235                 240

Phe Thr Phe Lys Lys Ile Leu Asn Lys Met Pro Ile Gly Asp Ser Leu
                245                 250                 255

Phe Asp Glu Ala Gly Ala Lys Asn Val Glu His Leu Val Glu Lys Ala
            260                 265                 270

Lys Lys Asn Asn Val Glu Leu Ile Leu Pro Val Asp Phe Val Thr Ala
        275                 280                 285

Asp Lys Phe Asp Lys Asp Ala Lys Thr Ser Ser Ala Thr Asp Ala Glu
    290                 295                 300

Gly Ile Pro Asp Asn Trp Met Gly Leu Asp Cys Gly Pro Lys Ser Val
305                 310                 315                 320

Glu Leu Phe Gln Gln Ala Val Ala Lys Ala Lys Thr Ile Val Trp Asn
                325                 330                 335

Gly Pro Pro Gly Val Phe Glu Phe Glu Lys Phe Ala Asn Gly Thr Lys
            340                 345                 350

Ser Leu Leu Asp Ala Ala Val Lys Ser Ala Glu Asn Gly Asn Ile Val
        355                 360                 365

Ile Ile Gly Gly Gly Asp Thr Ala Thr Val Ala Lys Lys Tyr Gly Val
    370                 375                 380

Val Glu Lys Leu Ser His Val Ser Thr Gly Gly Gly Ala Ser Leu Glu
385                 390                 395                 400

Leu Leu Glu Gly Lys Asp Leu Pro Gly Val Val Ala Leu Ser Asn Lys
                405                 410                 415

Asn

<210> SEQ ID NO 59
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atgggatgga gctatatcat cctcttcttg ttagcaacag ctacacgtgt ccactcccag      60
gtccaactgc agcagcctgg ggctgaggtg gtgaggcctg ggcttcagt gaaggtgtcc      120 tgcaaggctt ctggctacac ggtcagcagc tactggatga ctgggttaa gcagaggccg      180 gagcaaggcc ttgagtggat tggaaggatt gatccttacg atagtgaaac tcactacaat      240

```
caaaagttca aggacaaggc catattgact gtagacaaat cctccagcac agcctacatg    300
caactcagca gcctgacatc tgaggactct gcggtctatt actgtgcaag gacggccgct    360
tcgtttgact attggggcca aggcaccact ctcacagtct cctca                   405
```

<210> SEQ ID NO 60
<211> LENGTH: 135
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 60

```
Met Gly Trp Ser Tyr Ile Ile Leu Phe Leu Leu Ala Thr Ala Thr Arg
1               5                   10                  15

Val His Ser Gln Val Gln Leu Gln Gln Pro Gly Ala Glu Val Val Arg
            20                  25                  30

Pro Gly Ala Ser Val Lys Val Ser Cys Lys Ala Ser Gly Tyr Thr Val
        35                  40                  45

Ser Ser Tyr Trp Met Ser Trp Val Lys Gln Arg Pro Glu Gln Gly Leu
    50                  55                  60

Glu Trp Ile Gly Arg Ile Asp Pro Tyr Asp Ser Glu Thr His Tyr Asn
65                  70                  75                  80

Gln Lys Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Thr Ala Ala Ser Phe Asp Tyr Trp Gly Gln Gly
        115                 120                 125

Thr Thr Leu Thr Val Ser Ser
    130                 135
```

<210> SEQ ID NO 61
<211> LENGTH: 393
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 61

```
atgaagttgc ctgttaggct gttggtgctg atgttctgga ttcctgcttc cagcagtgat    60
gttgtgatga cccaaactcc actctccctg cctgtcagtc ttggagatca agcctccatc   120
tcttgcagat ctagtcagag ccttgtacac agtaatggaa actcctattt acattggtac   180
ctgcagaagc caggccagtc tccaaagctc ctgatctaca agtttccaa ccgattttct    240 ggggtcccag acaggttcag tggcagtgga tcagggacag atttcacact caatatcagc   300
agagtggagg ctgaggatct gggagtttat ttctgctctc aaagtacaca tgttccattc   360
acgttcggct cggggacaaa gttggaaata aaa                                393
```

<210> SEQ ID NO 62
<211> LENGTH: 131
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 62

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Ser Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Asn Ile Ser Arg Val Glu Ala Glu Asp Leu Gly Val Tyr Phe Cys
            100                 105                 110

Ser Gln Ser Thr His Val Pro Phe Thr Phe Gly Ser Gly Thr Lys Leu
        115                 120                 125

Glu Ile Lys
    130

<210> SEQ ID NO 63
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atgtacttgg gactgaactg tgtattcata gttttctct taaaaggtgt ccagagtgaa      60
gtgaagcttg aggagtctgg aggaggcttg gtgcaacctg gaggatccat gaaactctcc   120
tgtgttgcct ctggattcac tttcagtaac tactggatga actgggtccg ccagtctcca   180
gagaaggggc ttgagtgggt tgctgaaatt agattgaaat ctaataatta tgcaacacat   240
tatgcggagt ctgtgaaagg gaggttcacc atctcaagcg atgattccaa aagtagtgtc   300
tacctgcaaa tgaacaactt aagagctgaa gacactggca tttattactg ttcaactggg   360
aactactggg gccaaggcac cactctcaca gtctcctca                          399

<210> SEQ ID NO 64
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Tyr Leu Gly Leu Asn Cys Val Phe Ile Val Phe Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Glu Ile Arg Leu Lys Ser Asn Asn Tyr Ala Thr His
65                  70                  75                  80

Tyr Ala Glu Ser Val Lys Gly Arg Phe Thr Ile Ser Ser Asp Asp Ser
            85                  90                  95

Lys Ser Ser Val Tyr Leu Gln Met Asn Asn Leu Arg Ala Glu Asp Thr
            100                 105                 110

Gly Ile Tyr Tyr Cys Ser Thr Gly Asn Tyr Trp Gly Gln Gly Thr Thr
            115                 120                 125

Leu Thr Val Ser Ser
        130

<210> SEQ ID NO 65
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atggattttc agatgcagat tatcagcttg ctgctaatca gtgtcacagt catagtgtct        60
aatggagaaa ttgtgctcac ccagtctcca accaccatgg ctgcatctcc cggggagaag       120
atcactatca cctgcagtgc cagctcaact ataagttcca attacttgca ttggtatcag       180
cagaagccag gattctcccc taaactcttg atttatagga catccaatct ggcttctgga       240
gtcccagctc gcttcagtgg cagtgggtct gggacctctt actctctcac aattggcacc       300
atggaggctg aagatgttgc cacttactac tgccagcagg gtagtactat atcacgcacg       360
ttcggctcgg ggacaaagtt ggaaataaaa                                        390

<210> SEQ ID NO 66
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Asp Phe Gln Met Gln Ile Ile Ser Leu Leu Leu Ile Ser Val Thr
1               5                   10                  15

Val Ile Val Ser Asn Gly Glu Ile Val Leu Thr Gln Ser Pro Thr Thr
            20                  25                  30

Met Ala Ala Ser Pro Gly Glu Lys Ile Thr Ile Thr Cys Ser Ala Ser
        35                  40                  45

Ser Thr Ile Ser Ser Asn Tyr Leu His Trp Tyr Gln Gln Lys Pro Gly
    50                  55                  60

Phe Ser Pro Lys Leu Leu Ile Tyr Arg Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Gly Thr Met Glu Ala Glu Asp Val Ala Thr Tyr Tyr Cys Gln
            100                 105                 110

Gln Gly Ser Thr Ile Ser Arg Thr Phe Gly Ser Gly Thr Lys Leu Glu
        115                 120                 125

Ile Lys
    130

<210> SEQ ID NO 67
<211> LENGTH: 420
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 67

```
atggaaaggc actggatctt tctcttcctg ttgtcagtaa ctgcaggtgt ccactcccag      60
gtccagctgc agcagtctgc agctgaactg gcaagacctg gggcctcagt gaagatgtcc     120
tgcaaggctt ctggctacac ctttagtagc tacacgatgc actgggtaaa acagaggcct     180
ggacagggtc tggaatggat tggatacatt aatcctagca gtggatatac tgattacaat     240
cagaagttca aggacaagac acattgact gcagacaaat cctccagcac agcctacatg      300
caactgagca gcctgacatc tgaggactct gcggtctatt actgtgcaag actatatgat     360
aactacgatt actatgctat ggactactgg ggtcaaggaa cctcagtcac cgtctcctca     420
```

<210> SEQ ID NO 68
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Ala Arg
            20                  25                  30

Pro Gly Ala Ser Val Lys Met Ser Cys Lys Ala Ser Gly Tyr Thr Phe
        35                  40                  45

Ser Ser Tyr Thr Met His Trp Val Lys Gln Arg Pro Gly Gln Gly Leu
    50                  55                  60

Glu Trp Ile Gly Tyr Ile Asn Pro Ser Ser Gly Tyr Thr Asp Tyr Asn
65                  70                  75                  80

Gln Lys Phe Lys Asp Lys Thr Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Leu Tyr Asp Asn Tyr Asp Tyr Tyr Ala Met Asp
        115                 120                 125

Tyr Trp Gly Gln Gly Thr Ser Val Thr Val Ser Ser
    130                 135                 140
```

<210> SEQ ID NO 69
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
atggattcac aggcccaggt tcttatattg ctgctgctat ggtatctgg tacctgtggg       60 gacattgtga tgtcacagtc tccatcctcc ctggctgtgt cagcaggaga gaaggtcact     120
atgagctgca atccagtca gagtctgctc aatagtagaa tccgaaagaa ctacttggct      180
tggtaccagc agaaaccagg gcagtctcct aaactgctga tctactgggc atccactagg     240
gaatctgggg tccctgatcg cttcacaggc agtggatctg ggacagattt cactctcacc     300
```

```
atcagcagtg tgcaggctga tgacctggca gtttattact gcaagcaatc ttataatctg    360
ctcacgttcg gtgctgggac caagctggag ctgaaa                               396

<210> SEQ ID NO 70
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Asp Ser Gln Ala Gln Val Leu Ile Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Ala Gly Glu Lys Val Thr Met Ser Cys Lys Ser Ser Gln Ser
            35                  40                  45

Leu Leu Asn Ser Arg Ile Arg Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Asp Asp Leu Ala Val Tyr
                100                 105                 110

Tyr Cys Lys Gln Ser Tyr Asn Leu Leu Thr Phe Gly Ala Gly Thr Lys
            115                 120                 125

Leu Glu Leu Lys
    130

<210> SEQ ID NO 71
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atggctgtct tggggctgct cttctgcctg gtgacattcc caagctgtgt cccatcccag    60
gtgcagctga agcagtcagg acctggccta gtgcagccct cacagagcct gtccatcacc   120
tgcacagtct ctggtttctc attaactagc tatggtgtac actgggttcg ccagtctcca   180
ggaaagggtc tggagtggct gggagtgata tggagtggtg gaactacaga ctataatgca   240
gctttcatat ccagactgag catcagcaag gacaattcca agagccaagt tttctttaaa   300
atgaacagtc tgcaagctaa tgacacagcc atatattact gtgccagagg ggggcaccga   360
gggtttgctt actggggcca agggactctg gtcactgtct ctgca                   405

<210> SEQ ID NO 72
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72
```

Met Ala Val Leu Gly Leu Leu Phe Cys Leu Val Thr Phe Pro Ser Cys
1               5                   10                  15

Val Pro Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Gly Lys Gly Leu
    50                  55                  60

Glu Trp Leu Gly Val Ile Trp Ser Gly Gly Thr Thr Asp Tyr Asn Ala
65                  70                  75                  80

Ala Phe Ile Ser Arg Leu Ser Ile Ser Lys Asp Asn Ser Lys Ser Gln
                85                  90                  95

Val Phe Phe Lys Met Asn Ser Leu Gln Ala Asn Asp Thr Ala Ile Tyr
            100                 105                 110

Tyr Cys Ala Arg Gly Gly His Arg Gly Phe Ala Tyr Trp Gly Gln Gly
        115                 120                 125

Thr Leu Val Thr Val Ser Ala
        130                 135

<210> SEQ ID NO 73
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atgggcatca agatggagac acattctcag gtctttgtat acatgttgct gtggttgtct      60
ggtgttgaag agacattgt gatgacccag tctcacaaat tcatgtccac atcagtagga     120
gacagggtca gcatcacctg caaggccagt caagatgtgg gtactgctgt agcctggtat     180
caacagaaac cagggcaatc tcctaaacta ctgatttact gggcatccac ccggcacact     240
ggagtccctg atcgcttcac aggcagtgga tctgggacag atttcactct caccattagc     300
aatgtgcagt ctgaagactt ggcagattat ttctgtcagc aatatagcag ctatcctctc     360
acgttcggtg ctgggaccaa gctggagctg aaa                                  393

<210> SEQ ID NO 74
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Gly Ile Lys Met Glu Thr His Ser Gln Val Phe Val Tyr Met Leu
1               5                   10                  15

Leu Trp Leu Ser Gly Val Glu Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Gly Thr Ala Val Ala Trp Tyr Gln Gln Lys Pro
    50                  55                  60

Gly Gln Ser Pro Lys Leu Leu Ile Tyr Trp Ala Ser Thr Arg His Thr
65                  70                  75                  80

Gly Val Pro Asp Arg Phe Thr Gly Ser Gly Ser Gly Thr Asp Phe Thr

```
                85                  90                  95
Leu Thr Ile Ser Asn Val Gln Ser Glu Asp Leu Ala Asp Tyr Phe Cys
            100                 105                 110

Gln Gln Tyr Ser Ser Tyr Pro Leu Thr Phe Gly Ala Gly Thr Lys Leu
        115                 120                 125

Glu Leu Lys
    130

<210> SEQ ID NO 75
<211> LENGTH: 14
<212> TYPE: PRT
<213> ORGANISM: Unknown
<220> FEATURE:
<223> OTHER INFORMATION: Description of Unknown: universal T-cell
      epitope peptide

<400> SEQUENCE: 75

Gln Tyr Ile Lys Ala Asn Ser Lys Phe Ile Gly Ile Thr Glu
1               5                   10

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Ala Ala Ala Lys
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Gly Gly Gly Ser
1               5

<210> SEQ ID NO 78
<211> LENGTH: 21
<212> TYPE: PRT
<213> ORGANISM: Unknown
<220> FEATURE:
<223> OTHER INFORMATION: Description of Unknown: universal T-cell
      epitope peptide

<400> SEQUENCE: 78

Phe Asn Asn Phe Thr Val Ser Phe Trp Leu Arg Val Pro Lys Val Ser
1               5                   10                  15

Ala Ser His Leu Glu
            20

<210> SEQ ID NO 79
<211> LENGTH: 9
<212> TYPE: PRT
<213> ORGANISM: Unknown
<220> FEATURE:
<223> OTHER INFORMATION: Description of Unknown: GPV-M02
      peptide
```

<400> SEQUENCE: 79

Asn Pro Asp Cys Gly Leu Lys Thr Arg
1               5

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Pro Ala Ile Asn Val Thr Ser Ser Ser Thr Val Val Ala Ala Leu Glu
1               5                   10                  15

Ala Ala

<210> SEQ ID NO 81
<211> LENGTH: 10
<212> TYPE: PRT
<213> ORGANISM: Unknown
<220> FEATURE:
<223> OTHER INFORMATION: Description of Unknown: GPV-M01
      peptide

<400> SEQUENCE: 81

Pro Thr Thr Thr Ile Gly Ser Phe Pro Gln
1               5                   10

<210> SEQ ID NO 82
<211> LENGTH: 17
<212> TYPE: PRT
<213> ORGANISM: Unknown
<220> FEATURE:
<223> OTHER INFORMATION: Description of Unknown: GPV-M01A
      peptide

<400> SEQUENCE: 82

Asn Leu Pro Leu Phe Pro Thr Thr Thr Ile Gly Ser Phe Pro Gln Thr
1               5                   10                  15

Lys

<210> SEQ ID NO 83
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (14)..(14)
<223> OTHER INFORMATION: May or may not be present
<220> FEATURE:
<221> NAME/KEY: MISC_FEATURE
<222> LOCATION: (31)..(31)
<223> OTHER INFORMATION: May or may not be present

<400> SEQUENCE: 83

Ala Lys Phe Val Ala Ala Trp Thr Leu Lys Ala Ala Ala Cys Phe Trp
1               5                   10                  15

Val Asn Pro Asp Cys Gly Leu Lys Thr Arg Gly Pro Ser Leu Cys Ala
                20                  25                  30

Ile Leu Gly Gly Ser Lys Val Ser Asp Lys Ile
            35                  40

<210> SEQ ID NO 84
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (19)..(19)
<223> OTHER INFORMATION: May or may not be present
<220> FEATURE:
<221> NAME/KEY: MISC_FEATURE
<222> LOCATION: (36)..(36)
<223> OTHER INFORMATION: May or may not be present

<400> SEQUENCE: 84

Gln Tyr Ile Lys Ala Asn Ser Lys Phe Ile Gly Ile Thr Glu Gly Pro
1               5                   10                  15

Ser Leu Cys Phe Trp Val Asn Pro Asp Cys Gly Leu Lys Thr Arg Gly
            20                  25                  30

Pro Ser Leu Cys Ala Ile Leu Gly Gly Ser Lys Val Ser Asp Lys Ile
        35                  40                  45

<210> SEQ ID NO 85
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (26)..(26)
<223> OTHER INFORMATION: May or may not be present
<220> FEATURE:
<221> NAME/KEY: MISC_FEATURE
<222> LOCATION: (43)..(43)
<223> OTHER INFORMATION: May or may not be present

<400> SEQUENCE: 85

Phe Asn Asn Phe Thr Val Ser Phe Trp Leu Arg Val Pro Lys Val Ser
1               5                   10                  15

Ala Ser His Leu Glu Gly Pro Ser Leu Cys Phe Trp Val Asn Pro Asp
            20                  25                  30

Cys Gly Leu Lys Thr Arg Gly Pro Ser Leu Cys Ala Ile Leu Gly Gly
        35                  40                  45

Ser Lys Val Ser Asp Lys Ile
    50                  55

<210> SEQ ID NO 86
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (4)..(4)
<223> OTHER INFORMATION: May or may not be present
<220> FEATURE:
<221> NAME/KEY: MISC_FEATURE
<222> LOCATION: (22)..(22)
<223> OTHER INFORMATION: May or may not be present

<400> SEQUENCE: 86

Arg Gly Asp Cys Ile Val Ile Ile Gly Gly Gly Asp Thr Ala Thr Val

```
                1               5                  10                 15
Ala Lys Lys Lys Lys Cys Thr Thr Thr Ile Gly Ser Phe Pro Gln Thr
                20                 25                 30

Lys Asp Ile Arg
        35

<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (4)..(4)
<223> OTHER INFORMATION: May or may not be present
<220> FEATURE:
<221> NAME/KEY: MISC_FEATURE
<222> LOCATION: (22)..(22)
<223> OTHER INFORMATION: May or may not be present

<400> SEQUENCE: 87

Arg Gly Asp Cys Ile Val Ile Ile Gly Gly Asp Thr Ala Thr Val
1               5                  10                 15

Ala Lys Lys Lys Lys Cys Thr Thr Thr Ile Gly Ser Phe Pro Gln Thr
                20                 25                 30

Lys Asp Ile Arg Lys Leu His
        35

<210> SEQ ID NO 88
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (17)..(17)
<223> OTHER INFORMATION: May or may not be present
<220> FEATURE:
<221> NAME/KEY: MISC_FEATURE
<222> LOCATION: (35)..(35)
<223> OTHER INFORMATION: May or may not be present

<400> SEQUENCE: 88

Gln Tyr Ile Lys Ala Asn Ser Lys Phe Ile Gly Ile Thr Glu Lys Lys
1               5                  10                 15

Cys Ile Val Ile Ile Gly Gly Asp Thr Ala Thr Val Ala Lys Lys
                20                 25                 30

Lys Lys Cys Thr Thr Thr Ile Gly Ser Phe Pro Gln Thr Lys Asp Ile
        35                 40                 45

Arg

<210> SEQ ID NO 89
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (24)..(24)
<223> OTHER INFORMATION: May or may not be present
<220> FEATURE:
```

```
<221> NAME/KEY: MISC_FEATURE
<222> LOCATION: (42)..(42)
<223> OTHER INFORMATION: May or may not be present

<400> SEQUENCE: 89

Phe Asn Asn Phe Thr Val Ser Phe Trp Leu Arg Val Pro Lys Val Ser
1               5                   10                  15

Ala Ser His Leu Glu Lys Lys Cys Ile Val Ile Ile Gly Gly Gly Asp
            20                  25                  30

Thr Ala Thr Val Ala Lys Lys Lys Cys Phe Trp Val Asn Pro Asp
        35                  40                  45

Cys Gly Leu Lys Thr Arg
    50

<210> SEQ ID NO 90
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (20)..(20)
<223> OTHER INFORMATION: May or may not be present
<220> FEATURE:
<221> NAME/KEY: MISC_FEATURE
<222> LOCATION: (38)..(38)
<223> OTHER INFORMATION: May or may not be present

<400> SEQUENCE: 90

Arg Gly Asp Gln Tyr Ile Lys Ala Asn Ser Lys Phe Ile Gly Ile Thr
1               5                   10                  15

Glu Lys Lys Cys Ile Val Ile Ile Gly Gly Gly Asp Thr Ala Thr Val
            20                  25                  30

Ala Lys Lys Lys Lys Cys Phe Trp Val Asn Pro Asp Cys Gly Leu Lys
        35                  40                  45

Thr Arg
    50

<210> SEQ ID NO 91
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (27)..(27)
<223> OTHER INFORMATION: May or may not be present
<220> FEATURE:
<221> NAME/KEY: MISC_FEATURE
<222> LOCATION: (45)..(45)
<223> OTHER INFORMATION: May or may not be present

<400> SEQUENCE: 91

Arg Gly Asp Phe Asn Asn Phe Thr Val Ser Phe Trp Leu Arg Val Pro
1               5                   10                  15

Lys Val Ser Ala Ser His Leu Glu Lys Lys Cys Ile Val Ile Ile Gly
            20                  25                  30

Gly Gly Asp Thr Ala Thr Val Ala Lys Lys Lys Cys Phe Trp Val
        35                  40                  45

Asn Pro Asp Cys Gly Leu Lys Thr Arg
    50                  55
```

<210> SEQ ID NO 92
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (14)..(14)
<223> OTHER INFORMATION: May or may not be present
<220> FEATURE:
<221> NAME/KEY: MISC_FEATURE
<222> LOCATION: (31)..(31)
<223> OTHER INFORMATION: May or may not be present

<400> SEQUENCE: 92

Ala Lys Phe Val Ala Ala Trp Thr Leu Lys Ala Ala Ala Cys Thr Thr
1               5                   10                  15

Thr Ile Gly Ser Phe Pro Gln Thr Lys Asp Ile Arg Lys Lys Cys Ala
            20                  25                  30

Ile Leu Gly Gly Ser Lys Val Ser Asp Lys Ile
        35                  40

<210> SEQ ID NO 93
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (17)..(17)
<223> OTHER INFORMATION: May or may not be present
<220> FEATURE:
<221> NAME/KEY: MISC_FEATURE
<222> LOCATION: (34)..(34NO)
<223> OTHER INFORMATION: May or may not be present

<400> SEQUENCE: 93

Arg Gly Asp Ala Lys Phe Val Ala Ala Trp Thr Leu Lys Ala Ala Ala
1               5                   10                  15

Cys Thr Thr Thr Ile Gly Ser Phe Pro Gln Thr Lys Asp Ile Arg Lys
            20                  25                  30

Lys Cys Ile Val Ile Ile Gly Gly Asp Thr Ala Thr Val Ala Lys
        35                  40                  45

Lys

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 94

His His His His His His
1               5

<210> SEQ ID NO 95
<211> LENGTH: 14
<212> TYPE: PRT
<213> ORGANISM: Candida albicans

```
<400> SEQUENCE: 95

Tyr Gly Lys Asp Val Lys Asp Leu Phe Asp Tyr Ala Gln Glu
1               5                   10

<210> SEQ ID NO 96
<211> LENGTH: 14
<212> TYPE: PRT
<213> ORGANISM: Candida albicans

<400> SEQUENCE: 96

Pro Arg Ile Gly Gly Gln Arg Glu Leu Lys Lys Ile Thr Glu
1               5                   10

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: l-cyclohexylalanine
<220> FEATURE:
<221> NAME/KEY: MOD_RES
<222> LOCATION: (14)..(14)
<223> OTHER INFORMATION: Aminocaproic acid

<400> SEQUENCE: 97

Ala Lys Xaa Val Ala Ala Trp Thr Leu Lys Ala Ala Ala Xaa Cys
1               5                   10                  15
```